(12) United States Patent
Ayer et al.

(10) Patent No.: US 12,385,160 B2
(45) Date of Patent: Aug. 12, 2025

(54) ENZYME SCREENING METHODS

(71) Applicants: ROCHE SEQUENCING SOLUTIONS, INC., Pleasanton, CA (US); PRESIDENT AND FELLOWS OF HARVARD COLLEGE, Cambridge, MA (US)

(72) Inventors: Aruna Ayer, Santa Clara, CA (US); George M. Church, Brookline, MA (US); Mirko Palla, Newton, MA (US); Francois Pepin, Mountain View, CA (US); Sukanya Srinivasa Rao Arun Punthambaker, Boston, MA (US); Peter B. Stranges, Somerville, MA (US)

(73) Assignees: ROCHE SEQUENCING SOLUTIONS, INC., Pleasanton, CA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 1184 days.

(21) Appl. No.: 16/798,064

(22) Filed: Feb. 21, 2020

(65) Prior Publication Data
US 2020/0283842 A1 Sep. 10, 2020

Related U.S. Application Data

(63) Continuation of application No. PCT/US2018/047407, filed on Aug. 22, 2018.

(60) Provisional application No. 62/549,246, filed on Aug. 23, 2017.

(51) Int. Cl.
| | | |
|---|---|---|
| C40B 20/04 | (2006.01) | |
| C12Q 1/6869 | (2018.01) | |
| C40B 30/08 | (2006.01) | |
| C40B 50/06 | (2006.01) | |
| G01N 33/487 | (2006.01) | |
| G16B 30/10 | (2019.01) | |

(52) U.S. Cl.
CPC ............. *C40B 20/04* (2013.01); *C40B 30/08* (2013.01); *C40B 50/06* (2013.01); *G16B 30/10* (2019.02); *C12Q 1/6869* (2013.01); *G01N 33/48721* (2013.01)

(58) Field of Classification Search
None
See application file for complete search history.

(56) References Cited

U.S. PATENT DOCUMENTS

| | | |
|---|---|---|
| 8,324,914 B2 | 12/2012 | Chen et al. |
| 8,986,928 B2 | 3/2015 | Turner et al. |
| 9,377,437 B2 | 6/2016 | Chen et al. |
| 9,557,294 B2 | 1/2017 | Chen et al. |
| 2009/0024331 A1 | 1/2009 | Tomaney et al. |
| 2011/0193570 A1 | 8/2011 | Chen et al. |
| 2013/0029853 A1 | 1/2013 | Flusberg et al. |
| 2013/0244340 A1 | 9/2013 | Davis et al. |
| 2014/0034497 A1 | 2/2014 | Genia |
| 2015/0368710 A1 | 12/2015 | Fuller et al. |
| 2016/0201142 A1 | 7/2016 | Lo et al. |
| 2016/0222363 A1 | 8/2016 | Ayer et al. |
| 2016/0304860 A1 | 10/2016 | Hindson et al. |
| 2017/0044606 A1 | 2/2017 | Lo et al. |
| 2017/0088588 A1 | 3/2017 | Dorwart et al. |
| 2017/0268052 A1 | 9/2017 | Ayer et al. |
| 2018/0044725 A1 | 2/2018 | Kokoris et al. |
| 2018/0073071 A1 | 3/2018 | Ju et al. |
| 2018/0201933 A1 | 7/2018 | Cubillios-Ruiz et al. |
| 2018/0201992 A1 | 7/2018 | Wu et al. |
| 2018/0201993 A1 | 7/2018 | Turner et al. |
| 2020/0216887 A1* | 7/2020 | Craig ................... C12N 9/1247 |

FOREIGN PATENT DOCUMENTS

| | | |
|---|---|---|
| CN | 104254771 B | 1/2018 |
| JP | 2015525077 A | 9/2015 |
| WO | 2006028508 A2 | 3/2006 |
| WO | 2012083249 A2 | 6/2012 |
| WO | 2013109970 A1 | 7/2013 |
| WO | 2013188841 A1 | 12/2013 |
| WO | 2014074727 A1 | 5/2014 |
| WO | 2015061511 A1 | 4/2015 |
| WO | 2016069806 A2 | 5/2016 |
| WO | 2016124543 A1 | 8/2016 |
| WO | 2017083828 A1 | 5/2017 |
| WO | 2018034745 A1 | 2/2018 |

OTHER PUBLICATIONS

Derrington, I. et al. (2010), Nanopore DNA Sequencing with MspA. Proc. Natl. Acad. Sci., 107(37), 16060-16065.
Kasianowicz, J. (1996), Characterization of Individual Polynucleotide Molecules using a Membrane Channel. Proc. Natl. Acad. Sci., 93, 13770-3.
Kumar et al., PEG-Labeled Nucleotides and Nanopore Detection for Single Molecule DNA Sequencing by Synthesis, Sci Rep. 2012; 2:684.
Li and Durbin, Bioinformatics 25, 14:1754-1760 (2009).
Li and Durbin, Bioinformatics 26, 5:589-595 (2010).
Matthews, D., Sabina, J., Zuker, M., and Turner, D. (1999).
Needleman & Wunsch, J. Mol. Biol. 48:443 (1970).
Ning, Cox and Mullikin, Genome Research 11, 10:1725-1729 (2001).

(Continued)

*Primary Examiner* — Heather Calamita
*Assistant Examiner* — Jessica D Parisi
(74) *Attorney, Agent, or Firm* — Charney IP Law LLC; Thomas M. Finetti

(57) ABSTRACT

The present disclosure is directed to compositions and methods for deriving a plurality of kinetics parameters (240) for at least two different enzyme variants in a multiplex manner using nanopore-based sequencing. In some embodiments, the systems and methods may be used to screen different nanopore variants, or different combinations of both nanopore variants and enzyme variants.

14 Claims, 24 Drawing Sheets

Specification includes a Sequence Listing.

(56) References Cited

OTHER PUBLICATIONS

Pearson & Lipman, Proc. Nat'l. Acad. Sci. USA 85:2444 (1988).
Smith & Waterman, Adv. Appl. Math. 2:482 (1981).
Smith, T.F. and Waterman, M.S. 1981, Identification of common molecular subsequences, J. Mol. Biol. 147 195197.
Stranges, P. B. et al. Design and characterization of a nanopore-coupled polymerase for single-molecule DNA sequencing by synthesis on an electrode array. Proc. Natl. Acad. Sci. (2016). doi:10.1073/pnas. 1608271113.
Wuchty, S., Fontana, W., Hofacker, I., and Schuster, P. (1999). Complete suboptimal folding of RNA and the stability of secondary structures. Biopolymers 49, 145-165.
International Search Report and Written Opinion for PCT/US2018/047407 dated Jan. 1, 2019.
GenBank locus AC125138 (Nov. 13, 2003) downloaded from the internet Dec. 5, 2018 (https://www.ncbi.nlm.nih.gov/nuccore/AC125138); nt 101315-101362.
GenBank locus FG773419.1 (Jun. 12, 2008) downloaded from the internet Dec. 5, 2015 (https://www.ncbi.nlm.nih.gov/nucest/FG773419); nt 180-227.
GenBank locus CC203877 (Feb. 9, 2014) downloaded from the internet Dec. 5, 2018 (https://www.ncbi.nlm.nih.gov/ucgss/CC293877); nt 1046-1092.

* cited by examiner

ENZYME SCREENING METHODS

CROSS-REFERENCE TO RELATED APPLICATIONS

The present disclosure is a continuation of International Application No. PCT/US18/47407 filed on Aug. 22, 2018, which application claims the benefit of the filing date of U.S. Provisional Patent Application No. 62/549,246 filed on Aug. 23, 2017, the disclosure of which is hereby incorporated by reference herein in its entirety.

STATEMENT AS TO FEDERALLY SPONSORED RESEARCH

This invention was made with Government support under 1445570 awarded by the National Science Foundation. The Government has certain rights in this invention.

PARTIES TO A JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are Roche Sequencing Solutions, Inc. and The President and Fellows of Harvard College.

SEQUENCE LISTING

The nucleic and amino acid sequences provided herein are shown using standard letter abbreviations for nucleotide bases, and three letter code for amino acids, as defined in 37 C.F.R. 1.822. The sequence listing is submitted as an ASCII text file, named "P34416WO_ST25.txt" created on Aug. 21, 2018, 975 bytes, which is incorporated by reference herein.

BACKGROUND OF THE DISCLOSURE

The importance of DNA sequencing has increased dramatically from its inception four decades ago. It is recognized as a crucial technology for most areas of biology and medicine and as the underpinning for the new paradigm of personalized and precision medicine. Information on individuals' genomes and epigenomes can help reveal their propensity for disease, clinical prognosis, and response to therapeutics, but routine application of genome sequencing in medicine will require comprehensive data delivered in a timely and cost-effective manner.

Nanopore-based nucleic acid sequencing is an approach that has been widely studied. In the last two decades, there has been great interest in taking advantage of nanopores for polymer characterization and for distinguishing nucleotides in a low-cost, rapid, single-molecule manner. For example, Kasianowicz et. al. characterized single-stranded polynucleotides as they were electrically translocated through an alpha hemolysin nanopore embedded in a lipid bilayer (see, e.g., Kasianowicz, J. (1996), Characterization of Individual Polynucleotide Molecules using a Membrane Channel. Proc. Natl. Acad. Sci., 93, 13770-3). It was demonstrated that during polynucleotide translocation partial blockage of the nanopore aperture could be measured as a decrease in ionic current. Similarly, Gundlach et. al. demonstrated a method of sequencing DNA that used a low noise nanopore derived from *Mycobacterium smegmatis* ("MspA") in conjunction with a process called duplex interrupted sequencing (see, e.g., Derrington, I. et al. (2010), Nanopore DNA Sequencing with MspA. Proc. Natl. Acad. Sci., 107(37), 16060-16065). Here, a double strand duplex was used to temporarily hold the single-stranded portion of the nucleic acid in the MspA constriction. Akeson et. al. (see, e.g., PCT Publication No. WO/20150344945) disclose methods for characterizing polynucleotides in a nanopore that utilize an adjacently positioned molecular motor to control the translocation rate of the polynucleotide through or adjacent to the nanopore aperture.

In general, three nanopore sequencing approaches have been pursued: strand sequencing in which the bases of DNA are identified as they pass sequentially through a nanopore, exonuclease-based nanopore sequencing in which nucleotides are enzymatically cleaved one-by-one from a DNA molecule and monitored as they are captured by and pass through the nanopore, and a nanopore sequencing by synthesis (SBS) approach in which identifiable polymer tags are attached to nucleotides and registered in nanopores during enzyme-catalyzed DNA synthesis. Common to all these methods is the need for precise control of the reaction rates so that each base is determined in order. Strand sequencing requires a method for slowing down the passage of the DNA through the nanopore and decoding a plurality of bases within the channel; ratcheting approaches, taking advantage of molecular motors, have been developed for this purpose. Exonuclease-based sequencing requires the release of each nucleotide close enough to the pore to guarantee its capture and its transit through the pore at a rate slow enough to obtain a valid ionic current signal. In addition, both of these methods rely on distinctions among the four natural bases, two relatively similar purines and two similar pyrimidines. The nanopore SBS approach utilizes synthetic polymer tags attached to the nucleotides that are designed specifically to produce unique and readily distinguishable ionic current blockade signatures for sequence determination.

DNA polymerases are enzymes that duplicate genetic information by synthesizing a new complementary DNA strand from the parent template, thereby preserving genetic information. To date, polymerases mutants have been generated by directed evolution and methods for large scale screening of DNA polymerase mutants have been mutagenesis, phage display and compartmentalized self-replication methods. This has led to the identification and development of different polymerases for many biotechnological applications.

BRIEF SUMMARY OF THE DISCLOSURE

The present disclosure provides systems, compositions, and methods which facilitate the multiplex screening of a plurality of enzyme variants (e.g. DNA polymerase variants), such as with a nanopore or with nanopore-based sequencing, such that enzyme variants having unique or desirable properties may be elucidated. Rather than screen enzymes one at a time, which could be time consuming and costly, the present disclosure allows for enzyme variants, such as DNA polymerase variants, to be rapidly screened such that different enzyme properties, including efficacy, stability, processivity and fidelity, may be determined quickly and accurately. The present disclosure also enables the engineering of enzymes (e.g. DNA polymerases) with novel functions and/or with tailormade needs, for example, polymerases that can incorporate unnatural substrates or temperature sensitive mutants. In some embodiments, the present disclosure also provides systems, compositions, and methods which facilitate the multiplex screening of a plurality of nanopore variants, such that nanopore variants having unique or desirable properties may be elucidated. Of course, both nanopore variants and enzyme variants may be screened together within the same biochip, e.g. to elucidate a nanopore variant and enzyme variant pair having desirable characteristics.

Accordingly, in one aspect of the present disclosure is a method of screening a plurality of different enzyme variants using nanopore-based sequencing comprising: obtaining a biochip including a plurality of different nanopore sequencing complexes, wherein each different nanopore sequencing complex of the plurality of different nanopore sequencing complexes includes a polynucleotide having a unique molecular barcode, and wherein at least two of the different nanopore sequencing complexes include different enzyme variants; generating a sequencing data set for each different nanopore sequencing complex loaded onto the chip; classifying each of the generated sequencing data sets as associated with one different enzyme variant of the plurality of different enzyme variants based on identifications of the unique molecular barcodes included in the polynucleotides of the different nanopore sequencing complexes; and deriving a plurality of parameters for each one of the enzyme variants of the plurality of different enzyme variants, wherein the plurality of parameters for each one of the different enzyme variants are derived based on the classified sequence data sets associated with the respective one of the different enzyme variants.

In some embodiments, the identifications of the unique molecular barcodes included in the different nanopore sequencing complexes comprises (i) filtering quality reads to meet a minimum threshold base length; (ii) deriving a probability score using an automated alignment-based algorithm; and (iii) evaluating whether a computed probability score at least meets a pre-determined threshold probability score value. In some embodiments, the pre-determined threshold probability score value is 0.80. In some embodiments, the automated alignment-based classification algorithm derives the probability score by (i) identifying all barcode iteration boundaries in a raw read; (ii) splitting the iteration boundaries into individual barcode reads; (iii) aligning the individual barcode reads using an automated multiple sequence alignment algorithm to generate a consensus barcode from the alignment; (iv) locally aligning the generated consensus barcode to all possible barcodes utilized; and (v) identifying a most likely barcode candidate based on the sequence identify.

In some embodiments, a single sequence data set classified as associated with the one different enzyme variant of the plurality of different enzyme variants is utilized to derive the plurality of parameters for that one different enzyme variant. In some embodiments, at least two sequence data sets classified as associated with the one different enzyme variant of the plurality of different enzyme variants are utilized to derive the plurality of parameters for that one different enzyme variant.

In some embodiments, the plurality of parameters for each one of the different enzyme variants are selected from the group consisting of dwell time, a rate of a full catalytic cycle of tagged nucleotide incorporation, a tag release relate after nucleotide incorporation, a tag capture rate, and a tag capture dwell time. In some embodiments, the plurality of parameters are derived for each different nucleotide type. In some embodiments, the method further comprises performing a principal component analysis on the derived plurality of parameters for the each one of the different enzyme variants of the plurality of different enzyme variants. In some embodiments, the method further comprises evaluating whether a processivity rate for at least one nucleotide is altered (e.g. improved) for a first different enzyme variant of the plurality of different enzyme variants as compared with a second different enzyme variant of the plurality of different enzyme variants. In some embodiments, the evaluation comprises comparing at least one parameter of the plurality of parameters of the first different enzyme variant with the same at least one parameter of the second different enzyme variant.

In some embodiments, the enzymes are polymerases or reverse transcriptases. In some embodiments, at least three of the different nanopore sequencing complexes comprise three different polymerase variants. In some embodiments, one of the different polymerase variants is a control and wherein the other different polymerase variants each include at least one different mutation in comparison to the control.

In some embodiments, the unique molecular barcode comprises a nucleic acid sequence having between 10 and 200 bases. In some embodiments, the unique molecular barcode comprises a nucleic acid sequence having between 10 and 150 bases. In some embodiments, the unique molecular barcode comprises a nucleic acid sequence having between 10 and 100 bases. In some embodiments, the unique molecular barcode comprises a nucleic acid sequence having between 10 and 50 bases. In some embodiments, the unique molecular barcode comprises a nucleic acid sequence having between 10 and 25 bases. In some embodiments, each of the unique molecular barcodes have less than 85% sequence identity to each other. In some embodiments, the unique molecular barcode comprises a nucleic acid sequence having any of SEQ ID NOS: 1 to 3. In some embodiments, the polynucleotide comprises a unique molecular bar code and a Common Reading Region. In some embodiments, the polynucleotide is a circularized barcoded nucleic acid template which is annealed to a primer.

In another aspect of the present disclosure is a method of screening at least two enzyme variants using nanopore-base sequencing comprising: obtaining a biochip including a plurality of individually addressable nanopores, and wherein the obtained biochip comprises at least first and second different nanopore sequencing complexes, the first nanopore sequencing complex comprising a first enzyme variant and a first polynucleotide, and the second nanopore sequencing complex comprising a second enzyme variant and a second polynucleotide, wherein the first and second polynucleotides each include a different molecular barcode, and wherein the first and second enzyme variants are different; generating sequencing data sets for at least each of the first and second nanopore sequencing complexes; classifying each of the generated sequencing data sets as associated with at least either the first enzyme variant or the second enzyme variant, wherein the sequence data sets are each classified as associated with the at least either the first enzyme variant or the second enzyme variant based on identifications of at least the unique molecular barcodes included with the first and second polynucleotides; and deriving a plurality of kinetics parameters for each of the first and second enzyme variants based on the classified data sets associated with the first enzyme variant or the second enzyme variant.

In some embodiments, the method further comprises loading a third nanopore sequencing complex on the biochip, the third nanopore sequencing complex comprising a third enzyme variant and a third polynucleotide, wherein the third enzyme variant differs from the first and second enzyme variants, and wherein the third polynucleotide comprises a different molecular barcode than the first and second polynucleotide variants.

In some embodiments, the first and second enzyme variants are polymerase variants. In some embodiments, the nanopore-based sequencing comprises detecting byproducts of nucleotide incorporation events. In some embodiments, the byproducts are detected with an electrode disposed adjacent to each individually addressable nanopore.

In some embodiments, the first and second different polynucleotides have the structure -[Primer]-[Common Reading Region]-[Unique Barcode], wherein the "Common Reading Region" is the same for both the first and second polynucleotides and may be a polynucleotide sequence having between 10 and 100 bases; and wherein the "unique barcode" is a oligonucleotide sequence having between 5 and 50 bases, and wherein each "unique barcode" is different. In some embodiments, the first and second different polynucleotides have the structure -[Primer]-[Common Reading Region]-[Unique Barcode], wherein the "Common Reading Region" is the same for both the first and second polynucleotides and may be a polynucleotide sequence having between 10 and 50 bases; and wherein the "unique barcode" is a oligonucleotide sequence having between 8 and 25 bases, and wherein each "unique barcode" is different. In some embodiments, the "unique barcode" has a nucleic acid sequence having any of SEQ ID NOS: 1 to 3. In some embodiments, the first and second different polynucleotides have the structure -[Primer]-[Pre-determined Sequence]) wherein each of the first and second polynucleotides include a different "pre-determined sequence."

In another aspect of the present disclosure is a method of screening at least two nanopore variants using nanopore-base sequencing comprising: obtaining a biochip including a plurality of individually addressable nanopores, and wherein the obtained biochip comprises at least first and second different nanopore sequencing complexes, the first nanopore sequencing complex comprising a first nanopore variant and a first polynucleotide, and the second nanopore sequencing complex comprising a second nanopore variant and a second polynucleotide, wherein the first and second polynucleotides each include a different molecular barcode, and wherein the first and second nanopore variants are different; generating sequencing data sets for at least each of the first and second nanopore sequencing complexes; classifying each of the generated sequencing data sets as associated with at least either the first nanopore variant or the second nanopore variant, wherein the sequence data sets are each classified as associated with the at least either the first nanopore variant or the second nanopore variant based on identifications of at least the unique molecular barcodes included with the first and second polynucleotides; and deriving a plurality of kinetics parameters for each of the first and second nanopore variants based on the classified data sets associated with the first nanopore variant or the second nanopore variant. In some embodiments, an enzyme included within the first and second different nanopore sequencing complexes is the same (e.g. they both comprise the same polymerase variant). In some embodiments, an enzyme included within the first and second different nanopore sequencing complexes are different e.g. they both comprise different polymerase variants).

In some embodiments, the biochip comprises at least third and fourth different nanopore sequencing complexes, the third nanopore sequencing complex comprising a third nanopore variant and a third polynucleotide, and the fourth nanopore sequencing complex comprising a fourth nanopore variant and a fourth polynucleotide, wherein the first, second, third and fourth polynucleotides each include a different (i.e. unique) molecular barcode. In some embodiments, the first, second, third, and fourth nanopore sequencing complexes include combinations of two different nanopores and two different enzymes. In some embodiments, the third nanopore is the same as the first nanopore, but the enzyme variant within the first nanopore complex differs from the enzyme within the third nanopore complex; and likewise, the fourth nanopore is the same as the second nanopore, but the enzyme variant within the second nanopore complex differs from the enzyme within the second nanopore complex.

In some embodiments, the first and second different polynucleotides have the structure -[Primer]-[Common Reading Region]-[Unique Barcode], wherein the "Common Reading Region" is the same for both the first and second polynucleotides and may be a polynucleotide sequence having between 10 and 100 bases; and wherein the "unique barcode" is a oligonucleotide sequence having between 5 and 50 bases, and wherein each "unique barcode" is different. In some embodiments, the first and second different polynucleotides have the structure -[Primer]-[Common Reading Region]-[Unique Barcode], wherein the "Common Reading Region" is the same for both the first and second polynucleotides and may be a polynucleotide sequence having between 10 and 50 bases; and wherein the "unique barcode" is a oligonucleotide sequence having between 8 and 25 bases, and wherein each "unique barcode" is different. In some embodiments, the "unique barcode" has a nucleic acid sequence having any of SEQ ID NOS: 1 to 3. In some embodiments, the first and second different polynucleotides have the structure -[Primer]-[Pre-determined Sequence]) wherein each of the first and second polynucleotides include a different "pre-determined sequence."

In another aspect of the present disclosure is a biochip comprising a plurality of different nanopore sequencing complexes, each different nanopore sequencing complex comprising a different polynucleotide template, wherein the different polynucleotide templates each include a unique molecular barcode, and wherein at least two of the different nanopore sequencing complexes of the plurality of different nanopore sequencing complexes comprise different polynucleotide binding proteins, and wherein the different polynucleotide binding proteins are variants of each other.

In some embodiments, the first and second different polynucleotides have the structure -[Primer]-[Common Reading Region]-[Unique Barcode], wherein the "Common Reading Region" is the same for both the first and second polynucleotides and may be a polynucleotide sequence having between 10 and 100 bases; and wherein the "unique barcode" is a oligonucleotide sequence having between 5 and 50 bases, and wherein each "unique barcode" is different. In some embodiments, the polynucleotide templates each include a Common Reading Region. In some embodiments, at least a portion of each different polynucleotide template comprises a portion having a uniquely identifiable nucleic acid sequence. In some embodiments, the different polynucleotide templates have the structure -[Primer]-[Common Reading Region]-[Unique Barcode], wherein the "Common Reading Region" is the same for all of the different templates; and wherein the "unique barcode" is a oligonucleotide sequence having between 8 and 25 bases, and wherein each "unique barcode" differs for each different template. In some embodiments, the different polynucleotide templates have the structure -[Primer]-[Pre-determined Sequence]) wherein each of the different templates include a unique "pre-determined sequence."

In some embodiments, the biochip is loaded with at least three different nanopore sequencing complexes including at least three different polynucleotide binding protein variants. In some embodiments, the polynucleotide binding protein variants are polymerase variants. In some embodiments, the polynucleotide binding protein variants are DNA polymerase variants. In some embodiments, the polynucleotide binding protein variants are RNA polymerase variants. In some embodiments, the polynucleotide binding protein variants are reverse transcriptase variants. In some embodiments, the polynucleotide binding protein variants are helicase variants. In some embodiments, the polynucleotide binding protein variants are exonuclease variants.

In some embodiments, each of the plurality of nanopores within the biochip are individually addressable. In some embodiments, each individually addressable nanopore is adapted to detect a tag that is released from a tagged nucleotide upon polymerization of the tagged nucleotide by a polymerase variant. In some embodiments, each nanopore is individually coupled to sensing circuitry. In some embodiments, each nanopore sequencing complex is inserted in a membrane (e.g. a lipid bilayer).

In another aspect of the present disclosure is a biochip comprising a plurality of different nanopore sequencing complexes, each different nanopore sequencing complex comprising a different polynucleotide template, wherein the different polynucleotide templates each include a unique molecular barcode, and wherein at least two of the different nanopore sequencing complexes of the plurality of different nanopore sequencing complexes comprise different nanopores, and wherein the different nanopores are variants of each other. In some embodiments, at least four different nanopore sequencing complexes wherein at least two of the differ nanopore sequencing complexes include two different nanopores, and wherein at least two of the different nanopore sequencing complexes comprises two different polynucleotide binding templates. In some embodiments, the polynucleotide templates each include a Common Reading Region. In some embodiments, at least a portion of each different polynucleotide template comprises a portion having a uniquely identifiable nucleic acid sequence. In some embodiments, the different polynucleotide templates have the structure -[Primer]-[Common Reading Region]-[Unique Barcode], wherein the "Common Reading Region" is the same for all of the different templates; and wherein the "unique barcode" is a oligonucleotide sequence having between 8 and 25 bases, and wherein each "unique barcode" differs for each different template. In some embodiments, the different polynucleotide templates have the structure -[Primer]-[Pre-determined Sequence]) wherein each of the different templates include a unique "pre-determined sequence."

In another aspect of the present disclosure is a system including a biochip (such as any of the biochips identified above or disclosed herein) and one or more processors coupled to the biochip, wherein the one or more processors are programmed to aid in classifying detected nucleic acid sequences as associated with a particular polynucleotide binding protein variant based on molecular barcodes included within the nucleic acid sequences. In some embodiments, the one or more processors are further programmed to derive one or more parameters (e.g. kinetic parameters) for each different polynucleotide binding protein variant.

In another aspect of the present disclosure is a kit comprising: (a) a device comprising (i) a nanopore array having a membrane that comprises membrane-embedded nanopores, and (ii) a reference electrode on a cis side of the membrane and an individually addressable electrode array on a trans side of the membrane; and (b) a set of different enzymes (e.g. polymerases), each loaded or complexed with a different barcoded nucleic acid template, such as a circularized barcoded nucleic acid template.

BRIEF DESCRIPTION OF THE FIGURES

For a general understanding of the features of the disclosure, reference is made to the drawings. In the drawings, like reference numerals have been used throughout to identify identical elements.

FIG. 7A illustrates that all of the 96 possible barcodes were uniquely identified by the alignment-based classification algorithm (see Examples herein). FIG. 7B illustrates that the distribution of identified barcodes in individual sequencing experiments for RPol1:CBT1-32, RPol2:CBT33-64, and RPol3:CBT65-96. Counts are scaled by the width of the bin for clarity. The expected barcodes are uniquely identified with low false positive rates. FIG. 7B further illustrates the uneven distribution of barcode counts in a reflecting the different polymerase processivity.

DETAILED DESCRIPTION

Definitions

Figure 1A:
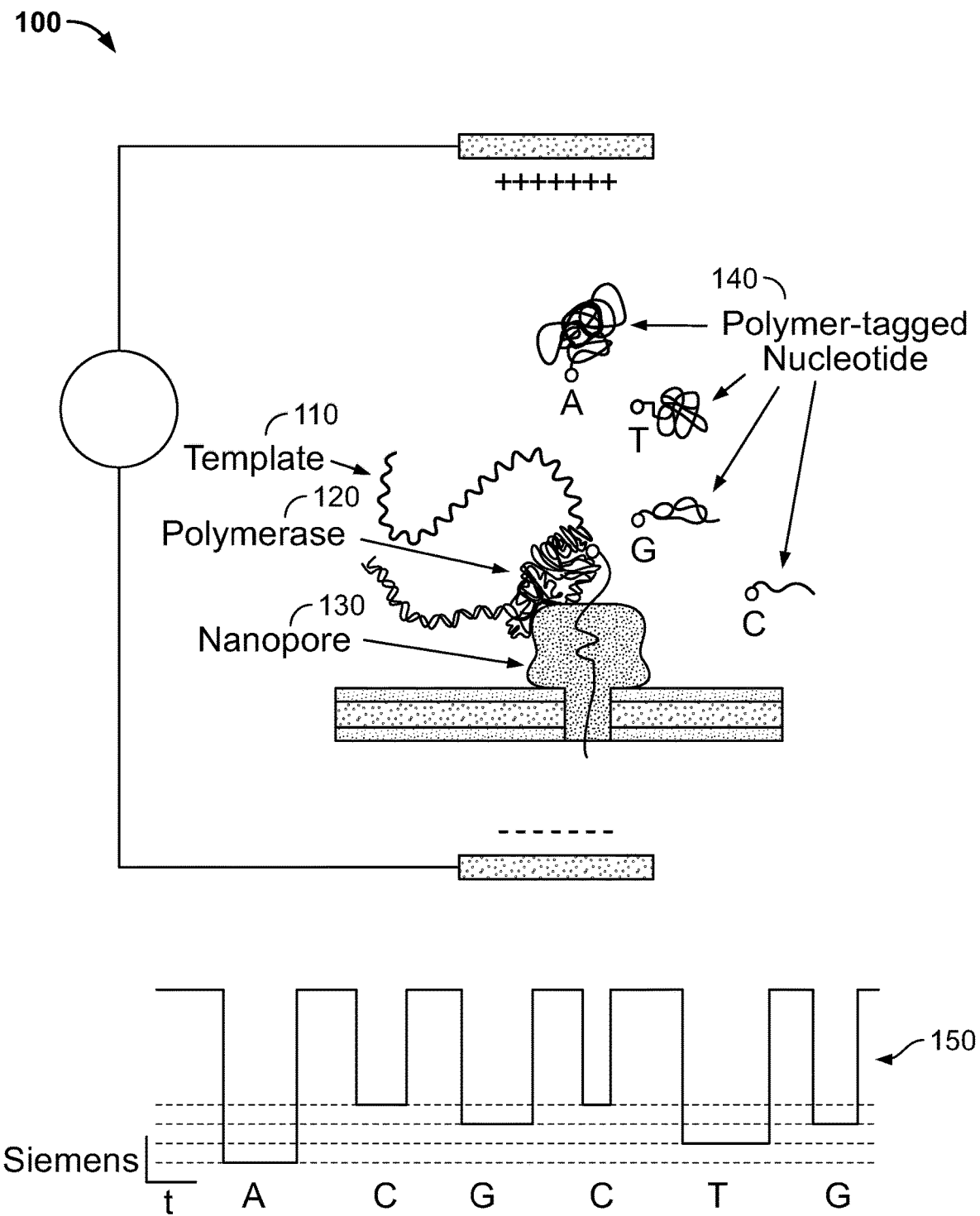
FIG. 1A illustrates single molecule DNA sequencing by a nanopore with polymer-tagged nucleotides (140). Each of the four nucleotides carry a different tag. During nanopore segueing, these tags, attached via the 5'-phosphate of the nucleotide, are released into the nanopore (130) one at a time where they produce unique current blockade signatures (150).

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

As used herein, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one" in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "alignment" refers to the identification of regions of similarity in a pair of nucleic acid sequences. For example, barcode sequences can be aligned, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), among others. The fraction or percentage of components in common is related to the homology or identity between the nucleic acid sequences. Alignments may be used to identify conserved domains and relatedness within these domains.

As used herein, the term "addressable" in the context of an array refers to members of the array located in discrete and defined regions. In the context of the present disclosure, each nanopore, such as each nanopore on a chip or biochip, is individually addressable, such that sequencing data may be independently generated for each nanopore, as described herein.

As used herein, the term "barcode" means an oligonucleotide present in a nucleic acid sequence in order to identify it. As used herein, the term "dwell time" refers to a length of time an enzyme (e.g. a polymerase) remains bound to a nucleotide during a binding reaction. In some embodiments, the dwell time of an enzyme is a function of whether the nucleotide in the active site of the enzyme correctly bases with a template nucleotide. For example, enzymes carrying an incorrect nucleotide bind to a polynucleotide and rapidly dissociate, producing a short dwell time due to the lack of stabilization conferred by correct nucleotide binding. In contrast, enzymes carrying the correct nucleotide bind to a polynucleotide and result in longer dwell times that include the kinetic steps nucleotide binding and catalysis.

Figure 4A:
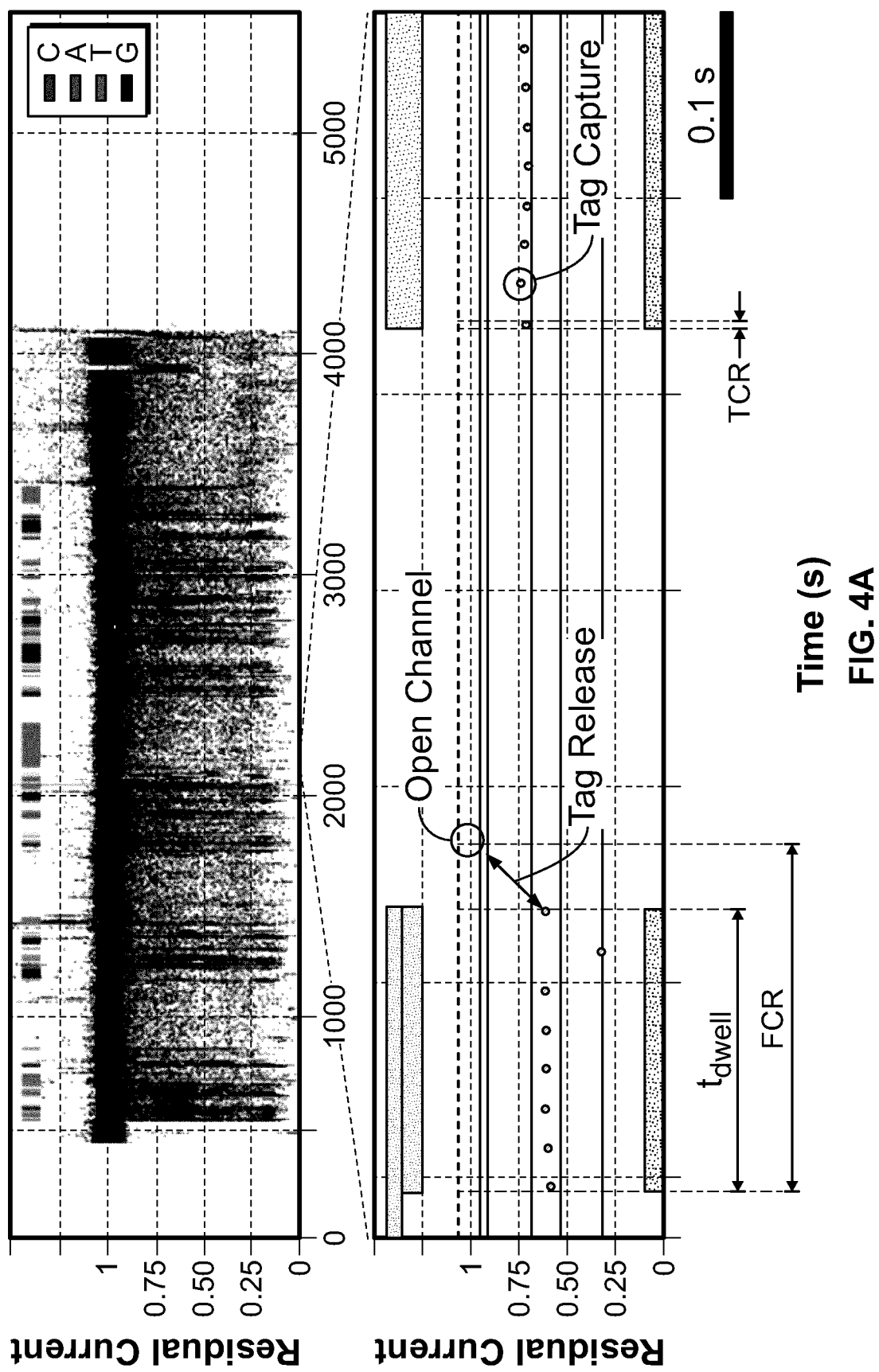
FIG. 4A illustrates the derivation of certain kinetics parameters derived from single-molecule tagged nucleotide capture signal.

As used herein, the terms "base call," "base calls," or "base calling" refers to the process of assigning bases (nucleobases) to the information obtained during sequencing e.g. by assigning nucleotides to chromatogram peaks (see, for example, FIGS. 1A and 4A herein).

As used herein, the term "enzyme-template complex" herein refers to an enzyme that is associated/coupled with a polymer, e.g., polynucleotide template.

As used herein, the term "nanopore" as refers to a pore, channel or passage formed or otherwise provided in a membrane. A nanopore can be defined by a molecule (e.g., protein) in a membrane. A membrane can be an organic membrane, such as a lipid bilayer, or a synthetic membrane, such as a membrane formed of a polymeric material. The nanopore may be disposed adjacent or in proximity to a sensing circuit, such as, for example, a complementary metal-oxide semiconductor (CMOS) or field effect transistor (FET) circuit. A nanopore may have a characteristic width or diameter on the order of 0.1 nanometers (nm) to about 1000 nm. Some nanopores are proteins. Alpha hemolysin is an example of a protein nanopore.

As used herein, the term "nanopore sequencing complex" refers to a nanopore linked or coupled to an enzyme, e.g., a polymerase, which in turn is associated with a polymer, e.g., a polynucleotide template. The nanopore sequencing complex is positioned in a membrane, e.g., a lipid bilayer, where it functions to identify polymer components, e.g., nucleotides or amino acids.

As used herein, the term "nanopore sequencing" or "nanopore-based sequencing" refers to a method that determines the sequence of a polynucleotide with the aid of a nanopore. In some embodiments, the sequence of the polynucleotide is determined in a template-dependent manner. The methods disclosed herein are not limited to any nanopore sequencing method, system, or device.

As used herein, the term "nucleic acid" refers to a molecule comprising one or more nucleic acid subunits. A nucleic acid can include one or more subunits (bases) selected from adenosine (A), cytosine (C), guanine (G), thymine (T) and uracil (U). Derivatives of these bases are exemplified in PCR Systems, Reagents and Consumables (Perkin Elmer Catalogue 1996-1997, Roche Molecular Systems, Inc., Branchburg, N.J., USA), which is entirely incorporated herein by reference. In some examples, a nucleic acid is deoxyribonucleic acid (DNA) or ribonucleic acid (RNA), or derivatives thereof. A nucleic acid may be single-stranded or double stranded. A nucleic acid can include any nucleic acid molecule, including, without limitation, DNA, RNA and hybrids or variants thereof.

As used herein, term "parameter" refers to a numerical value that characterizes a physical property or a representation of that property (e.g. kinetic properties of an enzyme under evaluation). In some situations, a parameter numerically characterizes a quantitative data set and/or a numerical relationship between quantitative data sets As used herein, the term "polymerase" refers to any enzyme capable of catalyzing a polymerization reaction. Examples of polymerases include, without limitation, a nucleic acid polymerase, a transcriptase or a ligase. A polymerase can be a polymerization enzyme. A "DNA polymerase" catalyzes the polymerization of deoxynucleotides. An "RNA polymerase" catalyzes the polymerization of ribonucleotides.

As used herein, a "polynucleotide" is a polymer or oligomer comprising one or more nucleotide as defined herein. A polynucleotide or oligonucleotide can comprise a DNA polynucleotide or oligonucleotide, a RNA polynucleotide or oligonucleotide, or one or more sections of DNA polynucleotide or oligonucleotide and/or RNA polynucleotide or oligonucleotide.

As used herein, the term "probability score" refers to a statistical value pertaining to an alignment between two nucleic acid sequences, wherein the value ranges from 0 to 1, wherein a value of 0 indicates a total mismatch between two aligned nucleic acid sequences, and wherein a value of 1 indicates a perfect match between two aligned nucleic acid sequences. As such, values closer to 1 would indicate a better match between two aligned nucleic acid sequences than those values that are closer to zero. In the context of the present disclosure, a probability score may be derived based on an alignment between generated sequencing data and a known (or control) nucleic acid sequence.

As used herein, the term "processivity" refers to the ability of an enzyme (e.g. a polymerase) to remain attached to the template and perform multiple modification reactions. "Modification reactions" include but are not limited to polymerization, and exonucleolytic cleavage. In some embodiments, "processivity" refers to the ability of an enzyme (e.g. DNA polymerase) to perform a sequence of polymerization steps without intervening dissociation of the enzyme from the growing DNA chains. Typically, "processivity" of a DNA polymerase is measured by the number of nucleotides (for example 20 nts, 300 nts, 0.5-1 kb, or more) that are incorporated i.e. polymerized by a polymerase into a growing DNA strand prior to the dissociation of the DNA polymerase from the growing DNA strand. The processivity of DNA synthesis by a DNA polymerase is defined as the number of nucleotides that a polymerase can incorporate into DNA during a single template binding event, before dissociating from a DNA template. The overall efficiency of DNA synthesis increases when the processivity of a polymerase increases. Processivity can be measured according the methods defined herein and in WO 01/92501 A1, the disclosure of which is incorporated by reference herein in its entirety. Processivity encompasses static processivity and replicative processivity.

As used herein, the terms "read" or "sequence read" refer to a string of nucleotides sequenced from any part or all of a nucleic acid molecule. In some embodiments, the term "read" refers to a sequence read from a portion of a nucleic acid sample. Typically, though not necessarily, a read represents a short sequence of contiguous bases in the sample. The read may be represented symbolically by the base sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bases) that can be used to identify a larger sequence or region, e.g., that can be aligned and specifically assigned to a polynucleotide template. In some embodiments, a read can comprise a small number of base calls, such as about eight nucleotides (base calls) but can contain larger numbers of base calls as well, such as 16 or more base calls, 25 or more base calls, 50 or more base calls, 100 or more base calls, or 120 or more nucleotides or base calls. The length of a read also can be expressed as a number of bases for one or more sample templates.

As used herein, the term "sequencing" refers to the determination of the order and position of bases in a nucleic acid.

As used herein, the term "tag" refers to a detectable moiety that may be atoms or molecules, or a collection of atoms or molecules. A tag may provide an optical, electrochemical, magnetic, or electrostatic (e.g., inductive, capacitive) signature, which may be detected with the aid of a nanopore.

As used herein, the term "tagged nucleotide" refers to a nucleotide having a tag attached at its terminal phosphate.

As used herein, the term "threshold" refers to any number that is used as a cutoff to characterize a sample, a nucleic acid, or portion thereof (e.g., a read). The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. Sometimes they are chosen for a particular purpose (e.g., to balance sensitivity and selectivity).

As used herein, the term "variant" refers to a modified protein e.g. a variant Pol6 polymerase, which displays altered characteristics when compared to the parental protein, e.g., altered processivity.

Multiplex Screening of Enzyme Variants

Described herein are systems and methods for the multiplex screening of at least two different enzyme variants using a nanopore or nanopore-based sequencing. In some embodiments, the systems and methods described herein enable the monitoring of enzyme kinetics during single-molecule DNA sequencing. It is believed, in some embodiments, that nanopore-based sequencing facilitates the accurate detection of individual nucleotide incorporation events and this technique may be utilized to rapidly screen enzyme variants in a multiplexed and high-throughput manner, e.g. a variety of metrics related to tagged nucleotide incorporation and tag capture during a base call may be determined using nanopore SBS.

In some embodiments, the systems and methods described herein may also be used to screen different nanopore variants. In other embodiments, the systems and methods described herein may also be used to screen different combinations of nanopore variants and enzyme variants. For example, four different nanopore sequencing complexes (N1E1, N1E2, N2E1, N2E2) may be screened having two different nanopore variants (N1 and N2) and two different enzyme variants (E1 and E2). By way of further example, for a particular polymerase variant (POL*), a barcode, and a given set of tagged nucleotides, a plurality of nanopore variants (POREn) may be conjugated to form POREn-POL* nanopore sequencing complexes for multiplex sequencing experiments. In some embodiments, tag capture characteristics, base-calling accuracy, read length and any other sequencing parameters could be compared to find the most optimal pore variant (with a given POL* and tagged nucleotides).

While certain embodiments disclosed herein describe the use of nanopore-based sequencing utilizing an indirect detection technique, i.e. measuring released tags as byproducts of a nucleotide incorporation event, such embodiments are for illustrative purposes only and the multiplex screening of any two enzyme variants may be performed using any type of nanopore or nanopore-based sequencing method, e.g. different enzyme variants may be evaluated where each of the enzyme variants are used as a molecular motor to drive a single polynucleotide strand through a nanopore, or where different enzyme variants may be evaluated where the enzyme variants are used to control translocation of a polynucleotide in proximity to a nanopore. Moreover, while certain embodiments may describe the formation of nanopore sequencing complexes including a polymerase mutant and the generation of sequencing data such that kinetic parameters may be derived pertaining to the various polymerase mutants, the methods described herein may be adapted to derive kinetic parameters for any enzyme or polynucleotide binding protein, e.g. endonucleases, reverse transcriptases, etc.

Nanopore Sequencing

Nanopore sequencing of a polynucleotide, e.g. DNA or RNA, may be achieved by strand sequencing and/or exosequencing of the polynucleotide sequence. In some embodiments, strand sequencing comprises methods whereby nucleotide bases of a sample polynucleotide strand are determined directly as the nucleotides of the polynucleotide template are threaded through the nanopore. In some embodiments, a polynucleotide can be sequenced by threading it through a microscopic pore in a membrane. Bases can be identified by the way they affect ions flowing through the pore from one side of the membrane to the other. In some embodiments, one protein molecule can "unzip" a DNA helix into two strands. A second protein can create a pore in the membrane and hold an "adapter" molecule. A flow of ions through the pore can create a current, whereby each base can block the flow of ions to a different degree, altering the current. The adapter molecule can keep bases in place long enough for them to be identified electronically (see PCT Publication No. WO/2018/034745, and United States Patent Application Publication Nos. 2018/0044725 and 2018/0201992, the disclosures of which are hereby incorporated by reference herein in their entireties). In some embodiments, sequencing may be performed according to the helicase and exonuclease-based methods of Oxford Nanopore (Oxford, UK), Illumina (San Diego, Calif.), or the nanopore sequencing-by-expansion methods of Stratos Genomics (Seattle, Wash.).

In some embodiments, nanopores may be used to sequence nucleic acid molecules indirectly, i.e. indirect sequencing may include any method where a polymerized nucleic acid molecule does not pass through the nanopore during sequencing. In these embodiments, the nucleic acid molecule may be at least partially located in the vestibule of the nanopore, but not in the pore (i.e., narrowest portion) of the nanopore. The nucleic acid molecule may pass within any suitable distance from and/or proximity to the nanopore, and optionally within a distance such that byproducts released from nucleotide incorporation events (e.g. tags cleaved from tagged nucleotides as described below) are detected in the nanopore.

In some embodiments, nanopore-based sequencing utilizes an enzyme, such as one located in proximity to a nanopore, which incorporate nucleotides into a growing polynucleotide chain, wherein the growing polynucleotide chain is complimentary to a corresponding template nucleic acid strand. Nucleotide incorporation events are catalyzed by the enzyme, such as DNA polymerase or any mutant or variant thereof and use base pair interactions with a template molecule to choose amongst the available nucleotides for incorporation at each location. "Nucleotide incorporation events" are the incorporation of a nucleotide into a growing polynucleotide chain. Byproducts of nucleotide incorporation events may be detected by the nanopore. In some embodiments, a byproduct may be correlated with the incorporation of a given type of nucleotide. In some embodiments, the byproduct passes through the nanopore and/or generates a signal detectable in the nanopore. Released tag molecules (described below) are examples of byproducts of nucleotide incorporation events. By way of example, FIG. 1A depicts a DNA polymerase (120) bound in close proximity to a nanopore (130). A polynucleotide template (110) to be sequenced is added along with a primer (the template is associated with the enzyme). To this nanopore sequencing complex (including the primer), four differently tagged nucleotides (140) are added to the bulk aqueous phase. After polymerase catalyzed incorporation of the correct nucleotide, the tag will be released and pass through the nanopore (130) to generate a unique ionic current blockade signal (150), thereby identifying the added base electronically because each of the tags have distinct chemical structures. Additional details pertaining to such nanopore-based sequencing systems and methods are described in U.S. Pat. Nos. 9,605,309 and 9,557,294, the disclosures of which are hereby incorporated by reference herein in their entireties.

In some embodiments, a method for sequencing a nucleic acid molecule comprises (a) polymerizing tagged nucleotides (e.g. using an enzyme which incorporates one tagged nucleotide at a time using a first nucleic acid molecule as a template) wherein a tag associated with an individual nucleotide is released upon polymerization, and (b) detecting the released tag with the aid of a nanopore. In some embodiments, the enzyme draws from a pool of tagged nucleotides. As noted herein, each type of nucleotide is coupled to a different tag molecule so that when the tags are released and pass near or through the nanopore, they may be differentiated from each other based on a signal that is generated (see, e.g., FIG. 1A). In some embodiments, each tag may have a different detectable signal, e.g. different signal intensities, different signal amplitudes, etc. which may be interpreted such as by base calling algorithms.

In some embodiments, the incorporated nucleotides are tagged nucleotides. Examples of tagged nucleotides are described in United States Patent Application Publication Nos. 2015/0368710 and 2018/0073071, the disclosures of which are hereby incorporated by reference herein in their entireties (see also Kumar et. al., PEG-Labeled Nucleotides and Nanopore Detection for Single Molecule DNA Sequencing by Synthesis, Sci Rep. 2012; 2:684). In some embodiments, nucleotide incorporation events release the tags from the tagged nucleotides, wherein the released tags are detected (see FIG. 1A). In this way, the incorporated base may be identified (i.e., A, C, G, T or U) since a unique tag is released from each type of nucleotide (i.e., A, C, G, T or U).

In some embodiments, a released tag flows through the nanopore or in close proximity to the nanopore such that a sensing circuit detects an electrical signal associated with the tag as it passes through or near the nanopore (see FIGS. 1A and 1). A detected signal (i.e. sequencing data) may be collected and stored in a memory location, and later used to construct a sequence of the nucleic acid. The collected signal may be processed to account for any abnormalities in the detected signal, such as errors. Suitable nanopore detectors are described in United States Patent Application Publication Nos. 2011/0193570 and 2018/0073071, the disclosures of which are hereby incorporated by reference herein in their entireties. Likewise, U.S. Pat. Nos. 9,377,437 and 8,324,914 describe the collection and analysis of electrical signals from nanopore-based sequencing systems, the disclosures of which are hereby also incorporated by reference herein in their entireties.

The nanopore may be formed or otherwise embedded in a membrane disposed adjacent to a sensing electrode of a sensing circuit, such as an integrated circuit. The integrated circuit may be an application specific integrated circuit (ASIC). In some examples, the integrated circuit is a field effect transistor or a complementary metal-oxide semiconductor (CMOS). The sensing circuit may be situated in a chip or other device having the nanopore, or off of the chip or device, such as in an off-chip configuration. The semiconductor can be any semiconductor, including, without limitation, Group IV (e.g., silicon) and Group III-V semiconductors (e.g., gallium arsenide).

A chip for sequencing a nucleic acid sample can comprise a plurality of individually addressable nanopores. An individually addressable nanopore of the plurality can contain at least one nanopore formed in a membrane disposed adjacent to an integrated circuit. Each individually addressable nanopore can be capable of detecting a tag associated with an individual nucleotide.

Enzymes

The enzymes coupled or otherwise conjugated to nanopores include polynucleotide processing enzymes, e.g. DNA and RNA polymerases, reverse transcriptases, exonucleases, and unfoldases. In some embodiments, the enzyme can be a wild-type enzyme, or it can be a variant form of the wild-type enzyme.

Variant enzymes can be engineered to possess characteristics that are altered relative to those of the parent enzyme. In some embodiments, the enzyme that is altered is a polymerase, e.g. a modified polymerase. As used herein, the term "modified DNA polymerase" refers to a DNA polymerase originated from another (i.e., parental) DNA polymerase and contains one or more amino acid alterations (e.g., amino acid substitution, deletion, or insertion) compared to the parental DNA polymerase. In some embodiments, a modified DNA polymerases of the disclosure is originated or modified from a naturally-occurring or wild-type DNA polymerase. In some embodiments, a modified DNA polymerase of the disclosure is originated or modified from a recombinant or engineered DNA polymerase including, but not limited to, chimeric DNA polymerase, fusion DNA polymerase or another modified DNA polymerase. Typically, a modified DNA polymerase has at least one changed phenotype compared to the parental polymerase. Examples of modified polymerases are described in United States Patent Application Publication No. 2016/0222363, the disclosure of which is incorporated by reference herein in its entirety.

In some embodiments, the altered characteristics of the polymerase enzyme could include changes in enzyme activity, fidelity, processivity (described herein), elongation rate, stability, or solubility. "Fidelity" generally refers to the accuracy with which a polymerase incorporates correct nucleotides into a copy of a nucleic acid template. DNA polymerase fidelity can be measured as the ratio of correct to incorrect nucleotide incorporations when the nucleotides are present at equal concentrations to compete for primer extension at the same site in the polymerase-primer-template DNA binary complex. In some embodiments, the polymerase can be mutated to reduce the rate at which the polymerase incorporates a nucleotide into a nucleic acid strand (e.g., a growing nucleic acid strand). In some embodiments, the reduced velocities (and improved sensitivities) can be achieved by a combination of site-specific mutagenesis of the nanopore protein and the incorporation of DNA processing enzymes, e.g., DNA polymerase, into the nanopore.

Uniquely Identifiable Polynucleotide Templates

Figure 2:
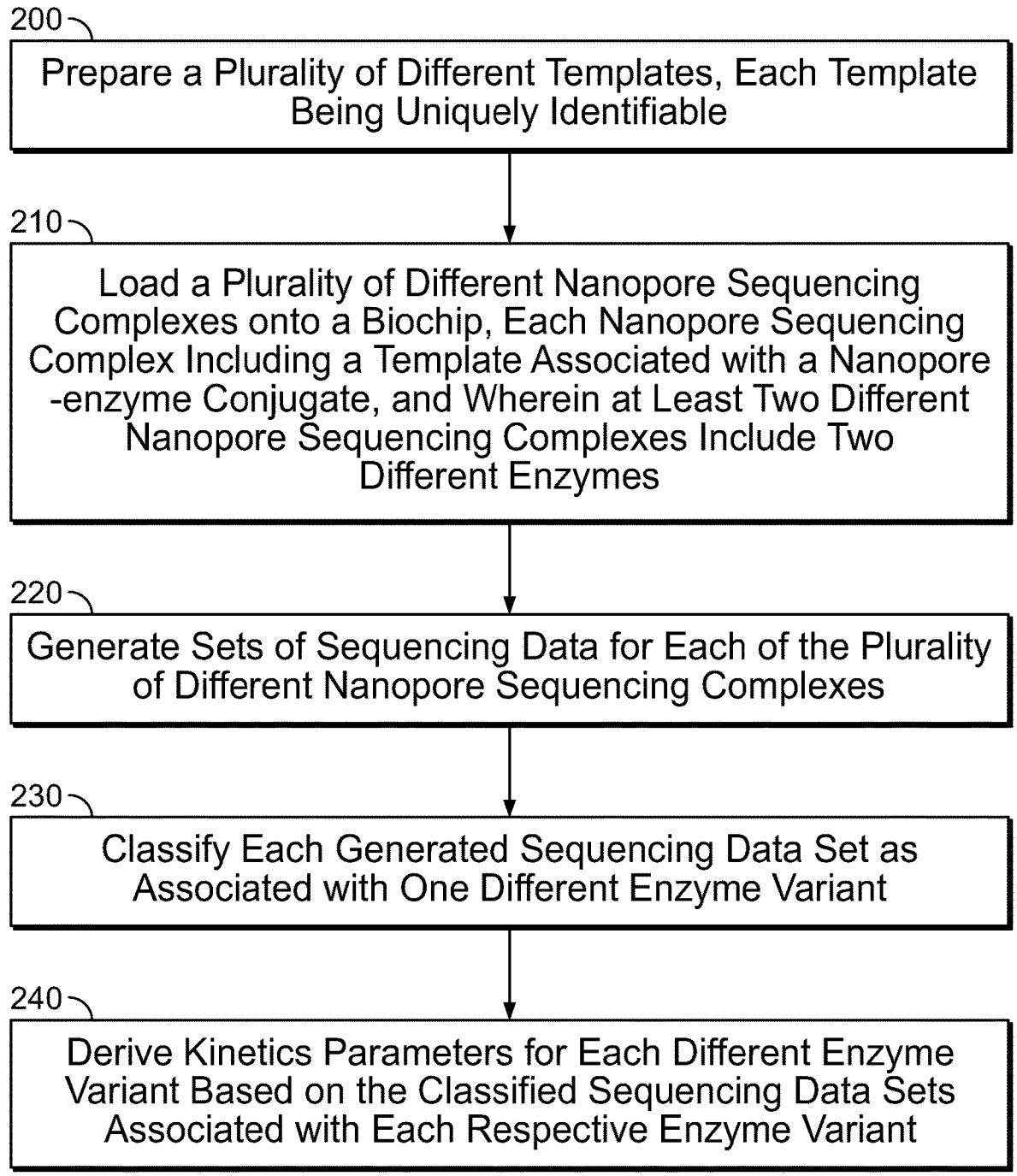
FIG. 2 sets forth a flowchart providing an overview of the steps of the multiplex screening of at least two enzyme variants according to some embodiments of the present disclosure.

With reference to FIG. 2, a first step (200) in screening for enzyme variants is to form a plurality of different templates, the templates designed to be associated with an enzyme of a nanopore sequencing complex. When enzymes are screened in a multiplex manner on the same biochip, there exists a vast amount of heterogenous sequencing data that is generated, and the templates ultimately serve to tie sequencing data acquired from each individual nanopore sequencing complex back to a particular enzyme variant based on an identification of the template (or portion of a template) associated with the particular enzyme of the nanopore sequencing complex.

For example, if a first nanopore sequencing complex includes a first template including a first identifiable molecular barcode, and a second nanopore sequencing complex includes a second template including a second identifiable molecular barcode, and further assuming that each nanopore sequencing complex includes a different enzyme variant, when the templates included within the different nanopore sequencing complexes are sequenced using nanopore-based sequencing, sequencing data may be generated such that the first and second identifiable molecular barcodes may be detected within the generated data sets, and by tracing the identifiable molecular barcodes back to a particular enzyme (e.g. through the use of classification algorithms as described herein), kinetics data derived from the sequence data sets may also be attributed to a particular enzyme or enzyme variant.

In some embodiments, at least a portion of a template includes a unique molecular barcode. In some embodiments, the template includes a unique molecular barcode and a common reading region. In some embodiments, the common reading region is the same for all templates, while the unique molecular barcode is different for all templates. In some embodiments, a unique molecular barcode is appended to the common reading region to form a plurality of different templates. In some embodiments, the unique molecular barcode may be detected within generated sequencing data and used to identify a particular enzyme associated with the template having the unique molecular barcode as described herein.

In some embodiments, a template may have the general structure:

-[Primer]-[Common Reading Region]-[Unique Barcode], wherein the "Common Reading Region" is the same for all templates and may be a polynucleotide sequence having between 10 and 500 bases; and wherein the "unique barcode" is a oligonucleotide sequence having between 5 and 100 bases, and wherein each "unique barcode" is different. For example, a first template may comprise -[Primer 1]-[Common Reading Region 1]-[Unique Barcode 1]; while a second different template may comprise -[Primer 1]-[Common Reading Region 1]-[Unique Barcode 2]. In other embodiments, the "unique barcode" is a oligonucleotide sequence having between 5 and 50 bases, and wherein each "unique barcode" is different. In yet other embodiments, the "unique barcode" is a oligonucleotide sequence having between 8 and 25 bases, and wherein each "unique barcode" is different. In some embodiments, the Common Reading Region may be used to characterize an enzyme, i.e. as sequence data is generated for the Common Reading Region portion of the template, metrics (such as tag incorporate rates, etc. as described herein) may be derived that could be analyzed and ultimately used to characterize an enzyme.

In some embodiments, each of the "unique barcodes" are designed such that each barcode has less than 85% sequence identity with any other barcode. In some embodiments, the "unique barcode" has at least 90% identity to any of SEQ ID NOS: 1 to 3. In other embodiments, the "unique barcode" has at least 95% identity to any of SEQ ID NOS: 1 to 3. In yet other embodiments, the "unique barcode" has a sequence of any of SEQ ID NOS: 1 to 3.

In other embodiments, the entire template (except for a primer region) may serve as an unique identifier. In some embodiments, a template may have the general structure -[Primer]-[Pre-determined Sequence]) (see also Examples 1 and 8, herein). In some embodiments, a first template may include a "pre-determined sequence" having 500 bases, and a second template may also comprise a "pre-determined sequence" having 500 bases, but where the pre-determined sequences of the first and second templates share less than 85% sequence identity. In some embodiments, a first template may include a "pre-determined sequence" having 200 bases, and a second template may also comprise a "pre-determined sequence" having 200 bases, but where the pre-determined sequences of the first and second templates share less than 85% sequence identity. In some embodiments, a first template may include a "pre-determined sequence" having 100 bases, and a second template may also comprise a "pre-determined sequence" having 100 bases, but where the pre-determined sequences of the first and second templates share less than 85% sequence identity. In some embodiments, a first template may include a "pre-determined sequence" having 50 bases, and a second template may also comprise a "pre-determined sequence" having 50 bases, but where the pre-determined sequences of the first and second templates share less than 85% sequence identity. In some embodiments, sequence data generated pertaining to the "pre-determined sequence" may be used for unique identification and for the derivation of kinetic parameters for an enzyme associated with the template.

Figure 1B:
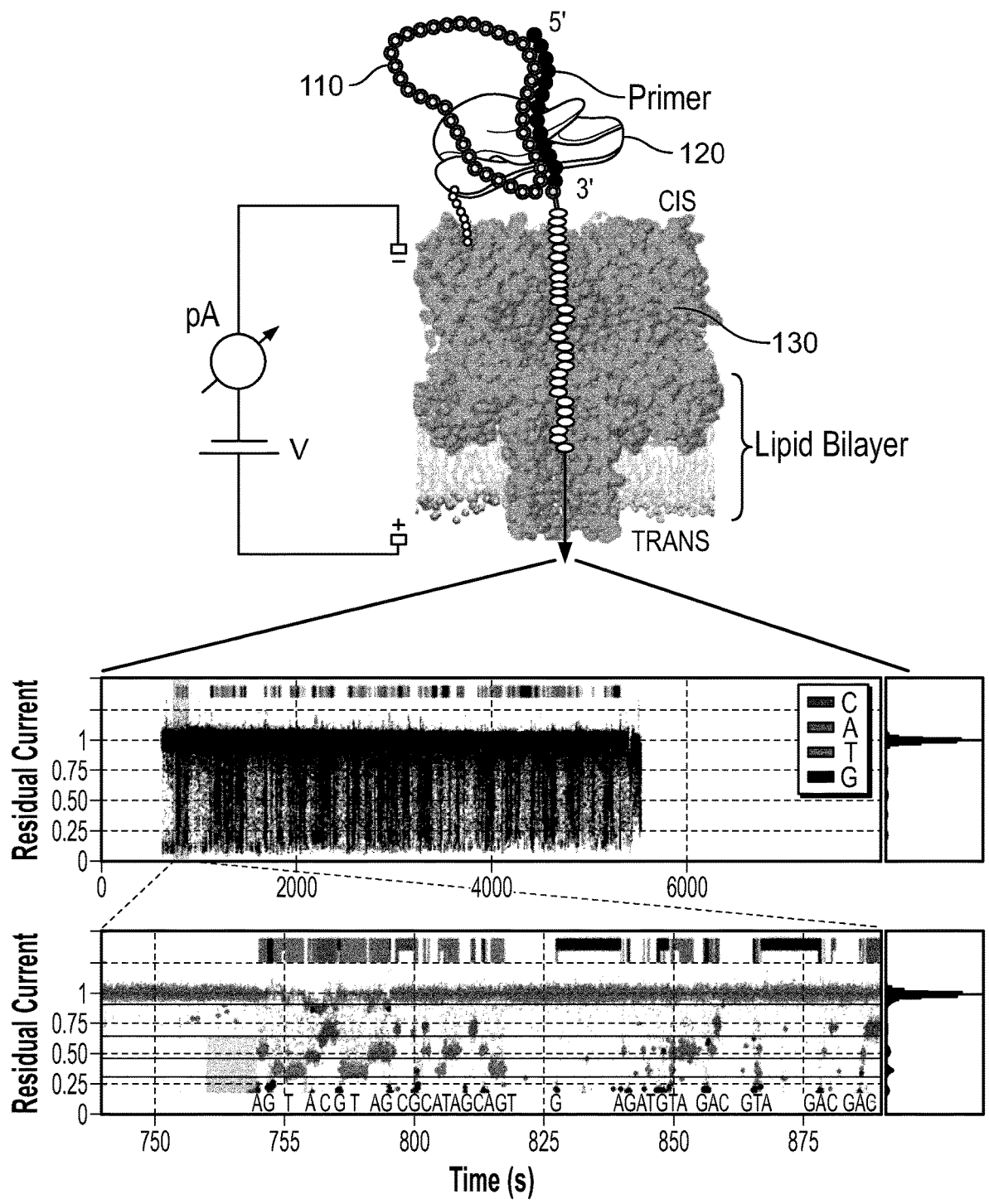
FIG. 1B illustrates a DNA polymerase (120) coupled to a nanopore (130) and loaded with a primed circular template (110) is inserted into a lipid bilayer on a nanopore array. Sequencing is started by adding tagged nucleotides that provide a characteristic ionic current blockade signature during incorporation. A representative plot of barcoded DNA template sequencing of the nanopore-polymerase-template complex on a complementary metal-oxide-semiconductor (CMOS) chip is illustrated (e.g. showing a normalized current versus time trace of tagged nucleotide captures for a single pore during a typical DNA sequencing experiment. The identified base calls are highlighted in standard Sanger colors in a zoomed-in region).

In some embodiments, the template polynucleotide may be circular, or dumbbell shaped. Examples of circular templates are shown in FIG. 1B and described further in Example 1 herein. In some embodiments, the circular and dumbbell-shaped templates may each be sequenced multiple times, e.g. 5 times, 10 times, 20 times, 50 times, etc.

In some embodiments, barcoded nucleic acid templates are produced by a method comprising: (a) providing a population of single-stranded nucleic acid templates, wherein each single-stranded nucleic acid template comprises a unique barcode sequence flanked by primer sequences; (b) eliminating one or more regions of the single-stranded nucleic acid templates that have a high-base-pairing probability; and (c) selecting a subpopulation of the single-stranded nucleic acid templates, wherein each unique barcode sequence of the subpopulation is not identical to any other unique barcode sequence of the subpopulation In some embodiments, single-stranded DNA molecules were computationally designed, such that it included a unique 32-base barcode region in a middle portion flanked by a common 19-base primer region at the ends, with a final length of 51-base. In some embodiments, the 32-base region is a unique identifier, while the 19-base region was used for circularization (i.e. it was believed to no other function other than helping the alignment). In some embodiments, the unique identifier comprises between 20 and 100 bases. In other embodiments, the unique identifier comprises between 30 and 80 bases. In some embodiments, a minimum free energy (MFE) associated with a barcode was calculated, a threshold was chosen to eliminate regions with a high-base pairing probability, which could form secondary structures believed to be difficult for a polymerase to read. In some embodiments, all barcodes had less than 85% sequence identity with each other.

Loading of the Polynucleotide Templates onto a Chip for Nanopore Sequencing

Following the formation of the plurality of different templates (step 200), each of the different templates are complexed with a nanopore-enzyme conjugate (i.e. a nanopore linked to an enzyme) and loaded onto a chip (210) for nanopore-based sequencing, with the proviso that the chip is loaded with at least two different nanopore sequencing complexes having two different enzyme variants.

In some embodiments, each different nanopore sequencing complex may include either (i) the same enzyme variant and a different polynucleotide template; or (ii) a different enzyme and a different polynucleotide template, again with the proviso that at least two of the different nanopore sequencing complexes loaded onto any biochip include two different enzyme variants. By way of example, assume that three polymerase variants (P1, P2, and P3) are to be screened according to the methods described herein. Also assume that six different templates (T1, T2, T3, T4, T5, and T6) are available to be complexed with any of the three different polymerase variants. One set of different nanopore sequencing complexes could include P1T1, P1T2, P2T3, P2T4, P3T5, and P3T6. Notably, three of the six different nanopore sequencing complexes include the three different enzyme variants, allowing for the multiplex analysis of the kinetics of the three different enzyme variants. One alternative set of nanopore sequencing complexes could include P1T1, P1T2, P1T3, P2T4, P2T5, P3T6. Once again, three of the six different nanopore sequencing complexes include the three different enzyme variants, again facilitating the multiplex analysis of the kinetics of the three different enzyme variants. Yet another alternative set of enzyme-template complexes could include P1T1, P1T2, P1T3, P12T4, P2T5, P2T6. In this example, only two different enzyme variants are included within the set of different nanopore sequencing complexes, but the two different enzyme variants could still be screened in a multiplex manner according to the methods described herein.

While the above example illustrates multiplex detection with up to three different enzyme variants, it is believed that there is no upper limit as to the number of different enzyme variants that may be tested on any single chip, i.e. there is no upper limit to the number of different nanopore sequencing complexes having different enzyme variants. In some embodiments, the number of enzyme variants that may be screened on a single biochip according to the present disclosure ranges from between 2 and about 1000. In other embodiments, the number of enzyme variants that may be screened n a single biochip according to the present disclosure ranges from between 2 and about 500. In other embodiments, the number of enzyme variants that may be screened n a single biochip according to the present disclosure ranges from between 2 and about 250. In other embodiments, the number of enzyme variants that may be screened n a single biochip according to the present disclosure ranges from between 2 and about 150. In other embodiments, the number of enzyme variants that may be screened n a single biochip according to the present disclosure ranges from between 2 and about 100. In yet other embodiments, the number of enzyme variants that may be screened according to the present disclosure ranges from between 2 and about 50. In further embodiments, the number of enzyme variants that may be screened according to the present disclosure ranges from between 2 and about 10. In yet further embodiments, the number of enzyme variants that may be screened according to the present disclosure ranges from between 3 and about 8. In even further embodiments, the number of enzyme variants that may be screened according to the present disclosure ranges from between 4 and about 8.

In some embodiments, each different nanopore sequencing complex may include either (i) the same nanopore variant and a different polynucleotide template; or (ii) a different nanopore and a different polynucleotide template, again with the proviso that at least two of the different nanopore sequencing complexes loaded onto any biochip include two different nanopore variants. By way of example, assume that three nanopore variants (N1, N2, and N3) are to be screened according to the methods described herein. Also assume that six different templates (T1, T2, T3, T4, T5, and T6) are available to be complexed with any of the three different nanopore variants. One set of different nanopore sequencing complexes could include N1T1, N1T2, N2T3, N2T4, N3T5, and N3T6. Notably, three of the six different nanopore sequencing complexes include the three different nanopore variants, allowing for the multiplex analysis of the kinetics of the three different nanopore variants. One alternative set of nanopore sequencing complexes could include N1T1, N1T2, N1T3, N2T4, N2T5, N3T6. Once again, three of the six different nanopore sequencing complexes include the three different nanopore variants, again facilitating the multiplex analysis of the kinetics of the three different enzyme variants.

Each of the different nanopore sequencing complexes (e.g. those including different enzyme variants, different nanopore variants, or any combination thereof) may then be inserted in a membrane, e.g. a lipid bilayer, and disposed adjacent or in proximity to a sensing electrode of a sensing circuit, such as an integrated circuit of a nanopore based sensor, e.g., a biochip (see FIG. 1A). Methods for assembling nanopore sequencing complexes are described in U.S. Patent Application Publication No. 2017/0268052, the disclosure of which is hereby incorporated by reference herein in its entirety. Other suitable methods for complexing each of the different templates to nanopore-enzyme conjugates include those described in PCT Publication Nos. WO2014/074727, WO2006/028508, and WO2012/083249, the disclosures of each are hereby incorporated by reference herein in their entireties.

Multiple nanopore sensors may be provided as arrays, such as arrays present on a chip or biochip. The array of nanopores may have any suitable number of nanopores. In some instances, the array comprises about 200, about 400, about 600, about 800, about 1000, about 1500, about 2000, about 3000, about 4000, about 5000, about 10000, about 15000, about 20000, about 40000, about 60000, about 80000, about 100000, about 200000, about 400000, about 600000, about 800000, about 1000000, and the like nanopores. Biochips and methods for making biochips are described in PCT Publication No. WO2015/061511, the disclosure of which is hereby incorporated by reference herein in its entirety. Further suitable biochips comprising a plurality of nanopores are described in United States Patent Application Publication No. 2017/0268052, the disclosure of which is hereby incorporated by reference herein in its entirety. Yet further suitable nanopore arrays are described in U.S. Pat. No. 8,986,928, the disclosure of which is hereby incorporated by reference herein in its entirety.

The nanopores of the nanopore sequencing complex include, without limitation, biological nanopores, solid state nanopores, and hybrid biological-solid state nanopores. Biological nanopores of the nanopore sequencing complexes include OmpG from *E. coli*, sp., *Salmonella* sp., *Shigella* sp., and *Pseudomonas* sp., and alpha hemolysin from *S. aureus* sp., MspA from *M. smegmatis* sp. The nanopores may be wild-type nanopores, variant nanopores, or modified variant nanopores. See, for example, United States Patent Application Publication No. 2017/0088588, the disclosure of which is hereby incorporated by reference herein in its entirety. In some embodiments, the variant nanopore of the nanopore sequencing complex is engineered to reduce the ionic current noise of the parental nanopore from which it is derived. Yet other nanopores are described in United States Patent Application Publication Nos. 2017/0268052 and 2018/0201993, the disclosures of which are hereby incorporated by reference herein in their entireties. Any nanopore variant now known or later discovered may be screened according to the methods described herein, such as contemporaneously with the screening of one or more enzyme variants (e.g. to identify a nanopore variant and enzyme variant pair that provides desirable properties).

Generating Sequence Data Sets for Each Different Template

Following the loading of the different nanopore sequencing complexes onto a chip (step 210), nanopore-based sequencing is conducted, and data is generated (step 220), i.e. sequencing data is independently generated for each nanopore sequencing complex. Said another way, sequencing data is acquired for each polynucleotide template associated with each nanopore as each is sequenced. Such sequencing data (i.e. the generated sequencing data sets), not only includes data pertaining to the template's nucleotide sequence, but also a variety of metrics, such as metrics relating to nucleotide incorporation rates. In some embodiments, the metrics derives are accuracy, percentage insertion, percentage deletion, incorporation rate, procession rate, dwell time (e.g. a time a tag is associated with a nanopore sequencing complex), waiting time (i.e. the time between dwell times), catalysis rate, tag-nucleotide "on rate," tag nucleotide "off rate," tag threading rate, sequencing lifetime, and pore lifetime. For example, for a template having a unique molecular barcode and a Common Reading Region, sequencing data within the data set for the unique molecular barcode portion may be used for identification and classification purposes (described herein) and the sequencing data within the data set for the Common Reading Region may be used to derive enzyme kinetics based on, for example, the rates of tag incorporation events during the sequencing of the Common Reading Region.

In some embodiments, sequencing of nucleic acids comprises preparing nanopore sequencing complexes as described herein, and determining polynucleotide sequences, such as by using tagged nucleotides as is described in PCT Publication No. WO/2014/074727, the disclosure of which is hereby incorporated by reference herein in its entirety. For example, a nanopore sequencing complex that is situated in a membrane adjacent to or in sensing proximity to one or more sensing electrodes, can detect the incorporation of a tagged nucleotide by an enzyme, e.g. a polymerase, as the nucleotide base is incorporated into a strand that is complementary to that of the template associated with the enzyme (e.g. the polymerase), and the tag of the nucleotide is detected by the nanopore. Each tag generates a characteristic and well-separated signal, thus uniquely identifying the added base. The incorporation event ends when the tag is cleaved by the polymerase before moving to the next base in the polynucleotide template. Valuable sequencing data may be collected, including a plurality of metrics related to tagged nucleotide incorporation and tag capture during a base call (see FIGS. 1B and 4A). The metrics may be collected and/or monitored in real-time, which adds information about single-molecule enzyme (e.g. polymerase) kinetics.

In some embodiments, a data file is generated including a variety of sequencing parameters for each nanopore. In some embodiments, a subset of the variety of sequencing parameters for the multiplex enzymatic screen are utilized, namely the rate of a full catalytic cycle of nucleotide incorporation, rate of tag release after nucleotide incorporation, time duration for a distinct nucleotide incorporation (tdwell), time duration between two distinct nucleotide incorporations (twait), rate of nucleotide incorporation transitions (N→N where the incorporating nucleotide is the same as the one that preceded it, or N→M where the incorporating nucleotide is different than the previous one, and where N is one of A, C, T, or G), time duration for a distinct tag capture, and number of observed current blockade events during a nucleotide incorporation per unit time, or any other kinetic parameter which can be derived from the single-molecule nanopore signal associated with the enzyme activity.

In some embodiments, the nanopore can be part of an electrical circuit that includes two electrodes. The current between the two electrodes can vary based on which nucleotide (base) or corresponding tag is in the nanopore. The first electrical signals can be detected using any suitable technique for measuring voltage or current in a circuit. In some embodiments, a voltage may be applied across a nanopore by coupling the nanopore to a voltage source (see FIG. 1A), and subsequently the voltage source may be decoupled from the nanopore such that a rate of decay of the voltage across the nanopore may be determined. According to this method, one molecule within the nanopore (e.g. a tag, or a nucleotide on a nascent strand that is passing through or near the nanopore) may be distinguished from another by virtue of measuring the voltage and/or decay rates. In some embodiments, the rate of the voltage decay is determined by measuring a voltage decay that occurs during a fixed time interval. Such methods are further described in U.S. Pat. No. 9,557,294 and in United States Patent Application Publication No. 2018/0201933, the disclosures of which are hereby incorporated by reference herein in their entireties.

Analysis of the data generated by sequencing is generally performed using software and/or statistical algorithms that perform various data conversions, e.g., conversion of signal emissions into base calls (see FIG. 4A), conversion of base calls into consensus sequences for a nucleic acid template, etc. Such software, statistical algorithms, and the use of such are described in detail, in U.S. Patent Application Publication Nos. 2009/0024331 2017/0044606 and in PCT Publication No. WO/2018/034745, the disclosures of which are hereby incorporated by reference herein in their entireties. In some embodiments, voltage signal events are converted to raw reads using probabilistic base-calling algorithms.

Classifying Each Generated Sequencing Data Set as Associated with a Particular Enzyme Variant Following the independent generation of sequencing data for each of the nanopore sequencing complexes (step 220), the generated sequencing data sets acquired are classified as being associated with a particular enzyme variant (step 230) (or if nanopore variants are utilized, to be associated with a particular nanopore variant). Simply put, this step enables sequencing data acquired for each nanopore (a sequencing data set) to be attributed to a particular enzyme or enzyme variant. In some embodiments, each of the generated sequencing data sets are classified as associated with a particular enzyme or enzyme variant based on an identification of the templates (see Examples 4 and 8 herein) or the unique, identifiable barcodes associated with each different template that was sequenced, i.e. the template that was included or associated with each different nanopore sequencing complex.

By way of example, for multiplexing with two different enzyme variants using two different unique barcodes, assume that the templates T1 and T2 included within the nanopore sequencing complexes P1T1 and P2T2 are sequenced and two sets of sequencing data are generated, one set of sequencing data for each of P1T1 and P2T2. Assume further that each of templates T1 and T2 include a unique molecular barcode. Given the uniquely identifiable molecular barcodes associated with each nanopore sequencing complex, namely the unique molecular barcodes included within T1 and T2, the generated sequencing data sets for P1T1 and P2T2 may each be associated with either the enzyme variant P1 or P2 by identifying the template T1 and T2 (or molecular barcode of the template) in the raw sequencing data using an automated classification algorithm. For instance, filtered read data (read data meeting certain sequence length criteria) may be provided and the reads for each sequencing data set may be compared against known template sequences for T1 and T2 (or known molecular barcodes sequences, respectively) such that probability scores may be generated and compared against a threshold value. Those alignments meeting or exceeding a predetermined cutoff or threshold probability score value are used to identify the template (or molecular barcode portion of a template) and enzyme. By extension, N polymerase variants may also be screened, which are loaded with N unique barcodes. The same classification algorithm may be applied as for the example set forth above where N=2. It is believed that the only limiting factor for N here is the number of available active nanopores on the electrode array during a sequencing run and the number of observations needed for a unique barcode for statistical significance. For example, for a 128K chip and requiring at least 10 observations for each barcode, i.e., polymerase variant, N=10000 variants could be screened assuming 100% pore active pore yield or N=1000 variant assuming 10% pore yield.

Figure 10:
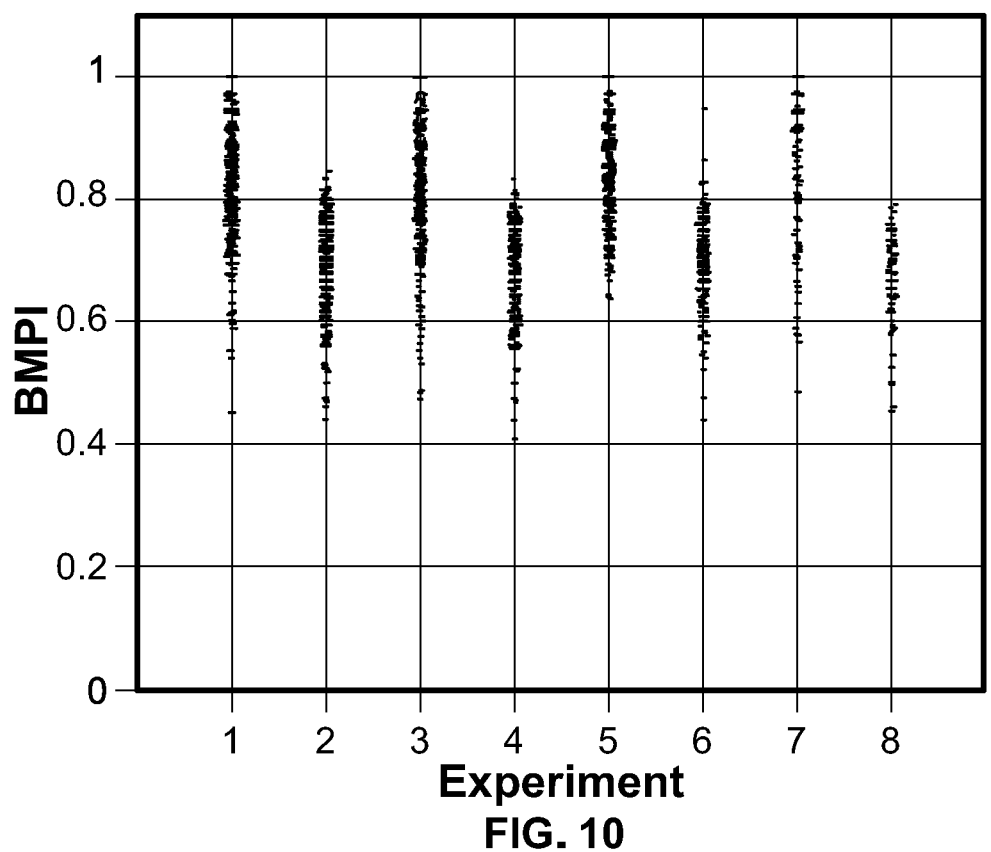
FIG. 10 illustrates barcoded DNA template switching. (Experiment 1) Barcode match probability index (BMPI) values of porin-polymerase-template complex RPol2-CBT2 when comparing to the expected barcode, CBT2. Number of quality raw reads (N)=612. (Experiment 2) When comparing to the incorrect barcode, the sequencing accuracy dramatically dropped. (Experiment 3) The presence of a non-complexed barcode (CBT1), immediately spiked in after the nanopore-polymerase-barcode complexing, did not indicate barcode replacement. (Experiment 4) When reads in 3 were compared to the incorrect barcode, a similar result was observed as for our control case in 2. (Experiment 5) Even, after an overnight incubation with a second barcode (CBT1), no barcode replacement was observed. (Experiment 6) On-chip barcode replacement was also tested, when second barcode was spiked in along with the tagged nucleotides after pore insertion. (Experiments 7 and 8) Again, the results indicated that the polymerase variants were uniquely labeled with their respective barcodes and are not replaced in an experiment.
Figure 11:
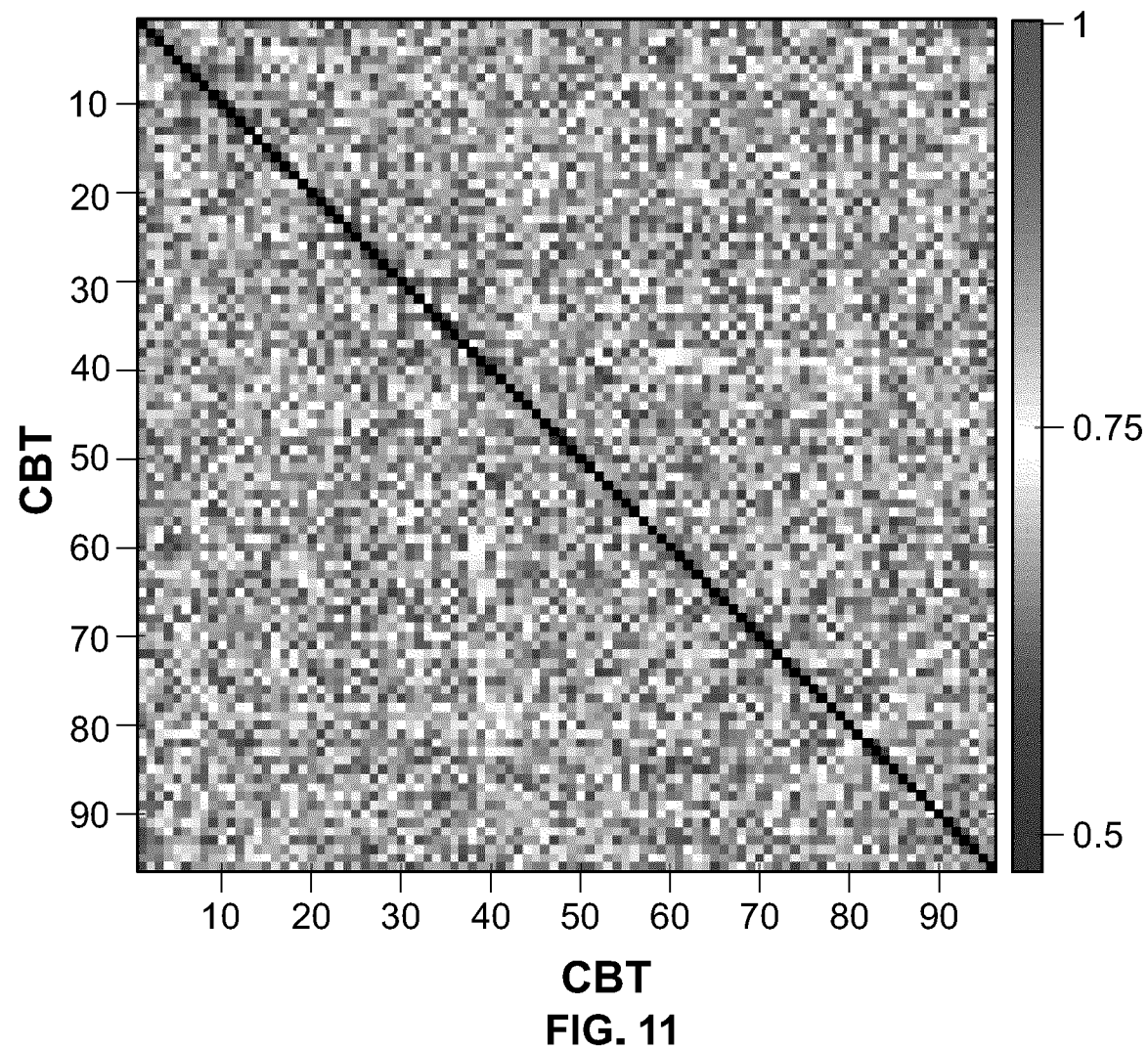
FIG. 11 provides an illustration of the barcode design for unique identification. Heatmap of sequence identity values of the 96 circular barcoded templates (CBT) were calculated using a Smith-Waterman local alignment algorithm. Each barcode sequence (x-axis) was compared to all of the other 96 CBTs in the same barcode set (y-axis) and the sequence identity value was recorded. The probability scale for local alignment is shown on the right, where 0 means total mismatch and 1 denotes total match. The diagonal line represents perfect identity, when the barcodes are aligned to themselves. For all off-diagonal CBTs, the sequence identities were <85% when the templates were locally aligned to each other.
Figure 12:
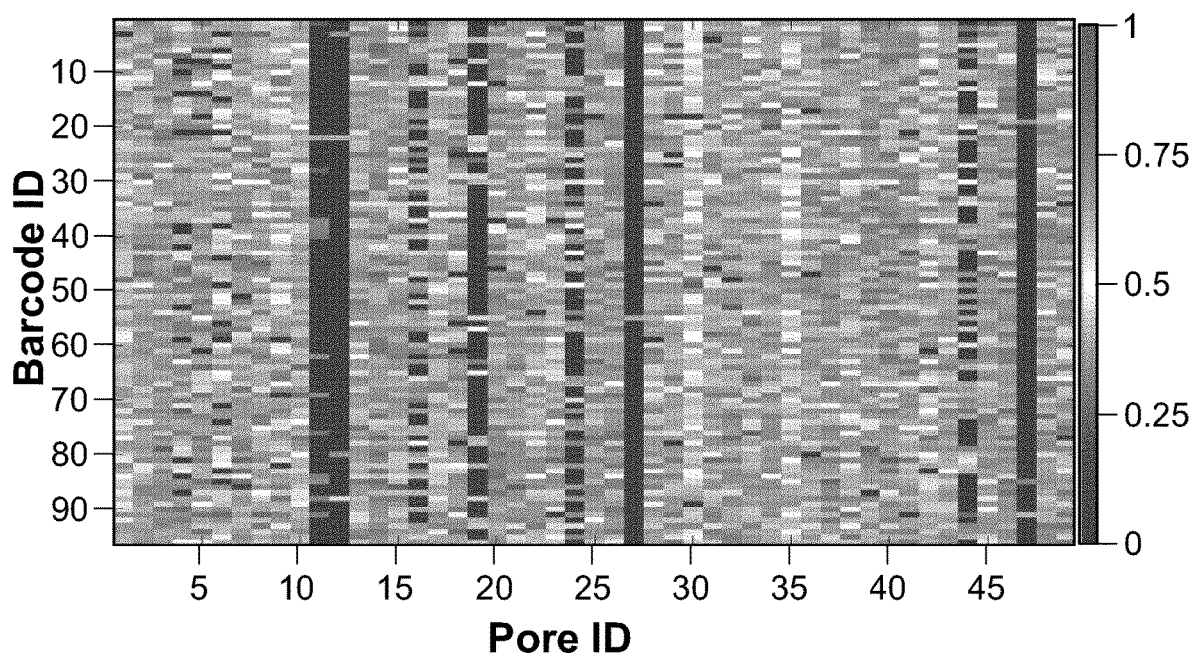
FIG. 12 sets forth a representative heatmap of raw read to circular barcoded template (CBT) comparison used by the classifier. Each raw read (x-axis) was compared to all of the 96 CBTs (y-axis) and the barcode match probability index (BMPI) value was recorded (Methods). BMPI is a probabilistic measure of barcode identification with a possible range of [0,1], as shown in the scale bar, where 0 means total mismatch and 1 denotes a total match. The maximum scoring BMPI value, above the 0.80 threshold, identified the most likely barcode candidate in each column. A BMPI value of 0 (blue) means that, at the initial classification step, the raw read did not meet the quality read criterion (Methods). Reads with maximum BMPI value <0.80 and BMPI values of 0 were discarded from the downstream analysis. Only 50 raw read evaluations are shown here for clarity.
Figure 13:
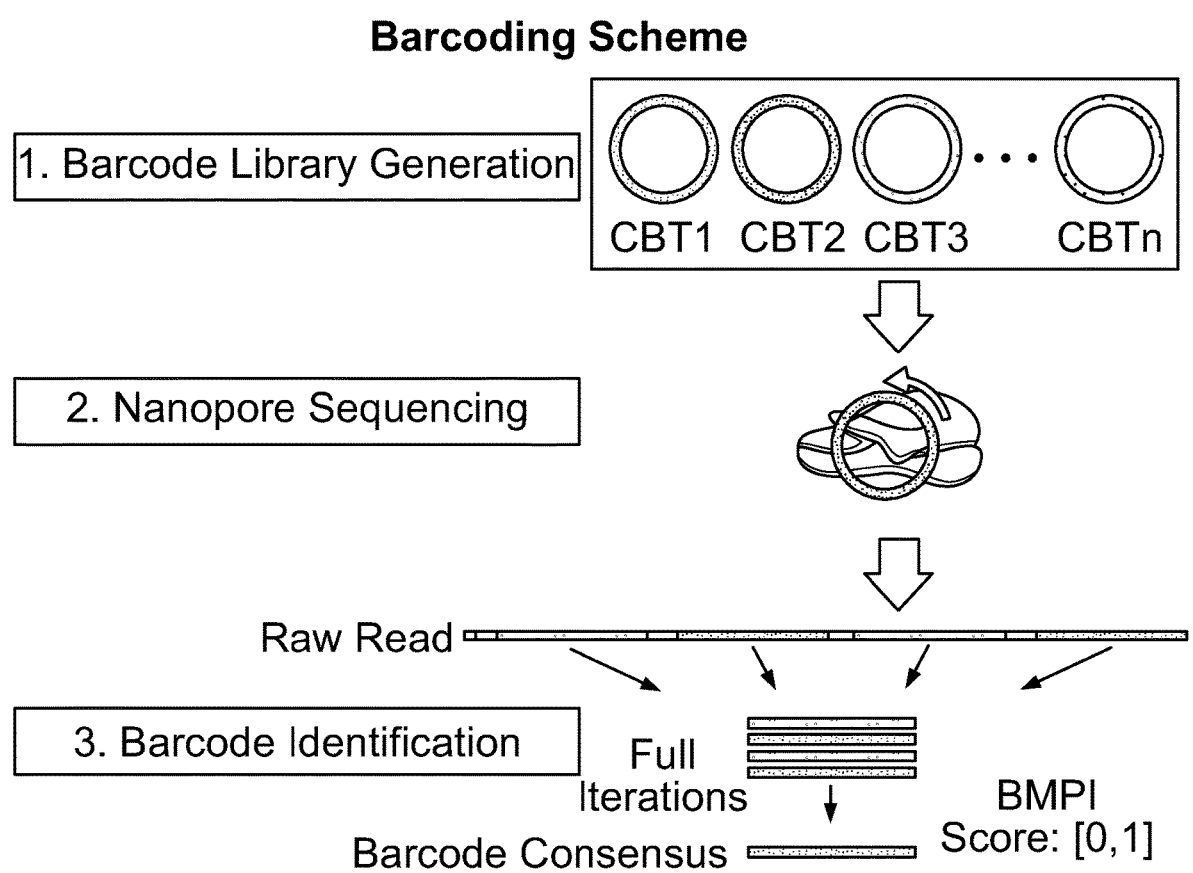
FIG. 13 sets forth a barcoding schematic illustrating the steps of generating a barcode library, nanopore sequencing, and barcode identification.

In some embodiments, the identification of the unique molecular barcode sequenced comprises (i) filtering quality reads to meet a minimum threshold base length (see Example 2C); (ii) deriving a probability score using an automated alignment-based algorithm (see Example 2D); and (iii) evaluating whether a computed probability score at least meets a pre-determined threshold probability score value (see, e.g., Example 4 herein). In some embodiments, quality reads were filtered out by requiring their read length to be greater than one (51 base) and less than ten full barcode iterations and their consensus sequence length to be greater than 10 base. In some embodiments, to filter out quality raw reads for barcode identification, the cumulative barcode match probability index ("BMPI") of all screened polymerase variants may be generated as a function of full barcode iterations. In general, it was observed that as the read length increases, the BMPI of the barcodes asymptotically increases up until about 10, about 14 and about 20 iterations for RPol1, RPol2, and RPol3 respectively (see Examples herein). In some embodiments, as described further in the Examples herein, a conservative approach may be taken, where raw reads with at most 10 full iterations are considered for barcode identification, while the rest of the other sequences are discarded in the downstream analysis. (see FIG. 10).

In some embodiments, the pre-determined threshold probability score value is 0.80. In some embodiments, the automated alignment-based algorithm aligns the filtered quality reads (i.e. the acquired nucleic acid sequences retained after processing which meet threshold read length criteria) to known molecular barcodes, where the known molecular barcodes are each of those unique molecular barcodes included within each polynucleotide template (and included within or associated with each of the different nanopore sequencing complexes). The skilled artisan will appreciate that higher probability scores will be returned when any given sequence is aligned with its correct known molecular barcode as opposed to an incorrect molecular barcode (see Example 4 herein).

Algorithms that can be used in connection with the present disclosure include, but are not limited to, Burrows-Wheeler Aligner ("BWA")-short (Li and Durbin, Bioinformatics 25, 14:1754-1760 (2009)), BWA-long (Li and Durbin, Bioinformatics 26, 5:589-595 (2010)), and Sequence Search and Alignment by Hashing Algorithm ("SSAHA") (Ning, Cox and Mullikin, Genome Research 11, 10:1725-1729 (2001)). In some embodiments, the alignment-based algorithm is a Smith-Waterman alignment-based classification algorithm (see Smith, T. F. and Waterman, M. S. 1981, Identification of common molecular subsequences, J. Mol. Biol. 147 195-197, the disclosure of which is hereby incorporated by reference herein in its entirety). In the Smith-Waterman algorithm, generated sequence data may be compared to a query sequence for example, a known template sequence or molecular tag sequence. As is familiar with a Smith-Waterman algorithm, probability scores may be attributed to different occurrences and overlaps of the nucleobases being compared. Examples of classifying sequencing data for each of the different templates included within the different nanopore sequencing complexes are set forth in Examples 4 and 8 herein.

In general, an algorithm receives a raw sequencing read of a barcode (from a nanopore experiment) and outputs a probability score, i.e. a barcode match probability index (BMPI). In some embodiments, this score describes the relative measure of how uniquely a barcode can be identified compared to the other possible barcodes in the measurement set. Since the barcodes utilized were circular, a sequencing read contains multiple barcode reads concatenated after each other, typically up until about 500 base. This design helped identify the barcodes from the raw reads, which are inherently error-prone.

In some embodiments, quality reads are filtered out by requiring their read length to be greater than one (51 base) barcode iteration. Next, all barcode iteration boundaries in the raw read are identified and split into individual barcode reads (of the same type, since they are generated from the same circular barcode) (e.g. from 1 to about 10 barcode reads). Subsequently a standard multiple sequence alignment algorithm may be used to align these barcode reads and obtain the consensus barcode from this alignment. Then, consensus barcode are locally aligned to all possible barcodes used in the screening experiment (e.g. 96 barcodes) if the consensus sequence are at least 10 base (see FIG. 10). Finally, the maximum scoring alignment (e.g. from all 96 comparisons) identifies the most likely barcode candidate based on sequence identity (matching bases/total bases in barcode). Since it is believed that nanopore sequencing is not 100% accurate, the circular nature of the barcodes may be leveraged to read the barcode multiple times to build up the confidence to uniquely identifying it in the pool of barcodes.

In embodiments where multiple different nanopore sequencing complexes share the same enzyme variant, any generated sequence data classified as associated with the same enzyme variant may be pooled together and the kinetics parameters may be derived from those pooled sequencing data sets. Using the example described above, assume again that three polymerase variants (P1, P2, and P3) are to be screened, and also assume that six different templates (T1, T2, T3, T4, T5, and T6) are available to be complexed with any of the three different polymerase variants. One set of different nanopore sequencing complexes could again include P1T1, P1T2, P2T3, P2T4, P3T5, and P3T6. After the generation of the sequencing data sets for each different nanopore sequencing complex (i.e. for each of P1T1, P1T2, P2T3, P2T4, P3T5, and P3T6) and the subsequent classification of each data set as belonging to a particular enzyme (i.e. either P1, P2, or P3 as based on an identification of the template sequences or barcodes within the template sequences), in this example all of the data sets associated with enzyme P1 may be pooled together (i.e. data sets for P1T1 and P2T2 may be pooled together). Likewise, all of the data sets associated with enzyme P2 or enzyme P3 may be pooled together, respectively. Kinetics parameters may then be derived from the pooled data sets (see Example 9 herein).

Derivation of Kinetics Parameters for Each Different Enzyme Variant

Following the classification of the generated data sets as belonging to a particular enzyme variant (step 230), the classified data sets (or pooled classified data sets as described above) are used such that kinetics parameters may be derived for each different enzyme variant (step 240).

In some embodiments, the kinetics parameters which may be derived include, but are not limited to: (i) dwell time (time duration for a distinct base call, which is a function of all kinetic steps after tagged nucleotide binding to the nanopore sequencing complex and up to tag release); (ii) FCR (the rate of a full catalytic cycle of tagged nucleotide incorporation); (iii) tagged release rate after nucleotide incorporation (TRR); (iv) tag capture rate (the number of observed current blockade events during a base call per unit time); and (v) tag capture dwell time (TCD) (the mean time duration for a distinct tag capture). The derivation of each of these kinetics parameters, as compared with received signals and current plots, are illustrated in FIG. 4A. See also Example 7, herein.

By way of example, one might be interested in screening for a particular DNA polymerase mutant having a defined set of kinetic properties characterized by enzyme fidelity, processivity, elongation rate, or on-chip lifetime. In this example, a variety of kinetic parameters, related to tagged nucleotide incorporation and tag capture during a base call may be derived from the voltage signal produced by single-molecule events. Here, dwell time may be defined as the time duration for a distinct base call, which is a function of all kinetic steps after tagged nucleotide binding to the ternary complex and up to tag release. Additionally, full catalytic rate (FCR) may be defined as the rate of two successive catalytic events, the catalytic cycle of tagged nucleotide incorporation and the tag cleavage by the polymerase (see, for example, FIG. 3A).

In some embodiments, kinetics parameters are derived for each nucleotide, i.e. for each of A, T, C, and G. For example, a total of 20 kinetics parameters may be derived when each of the five aforementioned types of kinetics parameters are derived for each of the types of nucleotides.

In some embodiments, comparisons may be made between the individual kinetics parameters and, by virtue of the comparisons, the processivity of each different enzyme variant tested may be evaluated. In some embodiments, the duration of a sequencing operation using a particular enzyme variant, e.g. a polymerase variant, can be measured based on the derived metrics. For example, if a specific polymerase variant improved processivity, it would be expected that the use of such a polymerase variant would cause an increase in sequencing lifetime. the metrics we calculate, we can measure on average how long sequencing lasted.

Biochips Loaded with Polynucleotide Binding Protein-Template Complexes

In another aspect of the present disclosure is a biochip loaded with a plurality of different nanopore sequencing complexes, where each of the different nanopore sequencing complexes comprise a different polynucleotide template (e.g. each having at least a portion having a uniquely identifiable barcode) where at least two different nanopore sequencing complexes of the plurality of nanopore sequencing complexes include two different polynucleotide binding proteins. Said another way, of all of the nanopore sequencing complexes provided on a biochip, at least two of the different nanopore sequencing complexes comprise two different polynucleotide binding proteins or variants thereof. In some embodiments, the at least two different polynucleotide binding proteins are two different mutants, e.g. mutants comprising a single amino acid alternation of substitution. In some embodiments, one of the at least two different polynucleotide binding proteins is a control and another of the at least two different polynucleotide binding proteins comprises at least one modification as compared with the control, where such modification may be introduced to alter the activity of the polynucleotide binding protein relative to the control.

The term "polynucleotide binding protein," as used herein refers to any protein that is capable of binding to a polynucleotide (e.g. a template polynucleotide) and controlling its movement with respect to a nanopore, such as through the nanopore. In some embodiments, the template is bound by the polynucleotide binding protein. In some embodiments, polynucleotide binding proteins include those derived from a polynucleotide handling, or processing, enzyme. A polynucleotide processing enzyme is a polypeptide that is capable of interacting with and modifying, or processing, at least one property of a polynucleotide. The protein may process the polynucleotide by unwinding the strands of a double helix to form regions of single-stranded DNA. In other embodiments, the protein may process the polynucleotide by cleaving it to form individual nucleotides. The protein can be, for example, a helicase, an exonuclease, a polymerase, a transcription factor or other nucleic acid handling protein.

In another aspect of the present disclosure is a biochip for screening at least two polynucleotide binding proteins, the biochip including an array including a plurality of different nanopore sequencing complexes disposed in a membrane, each nanopore sequencing complex having a nanopore coupled to a polynucleotide binding protein associated with a particular polynucleotide template, and wherein each different nanopore sequencing complex of the plurality of different nanopore sequencing complexes comprises a different template, and wherein at least two of the different nanopore sequencing complexes of the plurality of different nanopore sequencing complexes included within the array have two different polynucleotide-binding proteins. In some embodiments, the nanopore of each of the nanopore sequencing complexes is disposed adjacent or in proximity to an electrode or other sensing circuit. In some embodiments, each nanopore is individually addressable. In some embodiments, each nanopore includes a single polynucleotide-binding protein-template complex. In some embodiments, each individual nanopore is configured to detect a nucleotide passing through a nanopore or, in the alternative, to detect a tag associated with a tagged nucleotide during incorporation of the nucleotide into a growing polynucleotide chain by the polynucleotide-binding protein.

In some embodiments, the polynucleotide binding protein is a helicase and wherein the helicase controls the movement of a target polynucleotide through a nanopore. In some embodiments, the present disclosure provides a biochip loaded with at least two different nanopore sequencing helicases-template complexes (i.e. helicase enzymes associated with or bound to a template, the helicase coupled to the nanopore), wherein each different complex comprises a different template enabling the unique identification of each complex; and wherein at least two of the different complexes loaded onto the chip include a different helicase (e.g. two different helicase variants). In this way, the helicase variants may be screened in a multiplex manner according to the methods described herein. In some embodiments, the helicase variants may be screened to determine how differences between the variants change the helicase variant's ability to control the movement of a template polynucleotide.

In some embodiments, the polynucleotide binding protein is an exonuclease and wherein the exonuclease controls the cleavage of individual nucleotides from the template polynucleotide. In some embodiments, the present disclosure provides a biochip loaded with at least two different nanopore sequencing exonuclease-template complexes (i.e. exonuclease enzymes associated with or bound to a template, the exonuclease coupled to the nanopore), wherein each different complex comprises a different template enabling the unique identification of each complex; and wherein at least two of the different complexes loaded onto the chip include a different exonuclease (e.g. two different exonuclease variants). In this way, the exonuclease variants may be screened in a multiplex manner according to the methods described herein. In some embodiments, the exonuclease variants may be screened to determine how differences between the variants change the exonuclease variant's ability to cleave nucleotides.

In some embodiments, the polynucleotide binding protein is an polymerase. In some embodiments, the present disclosure provides a biochip loaded with at least two different nanopore sequencing complexes (i.e. polymerase enzymes associated with or bound to a template, where the polymerase is coupled to a nanopore), wherein each different polymerase-template complex comprises a different template enabling the unique identification of each complex; and wherein at least two of the different complexes loaded onto the chip include a different polymerase (e.g. two different polymerase variants). In this way, the polymerase variants may be screened in a multiplex manner according to the methods described herein.

EXAMPLES

Example 1—Circular DNA Template Preparation, Polymerase Preparation, and Porin-Polymerase-Template Complex Formation In the 3-plex experiments described herein (see, Example 3), 51-base single-stranded DNA (ssDNA) oligonucleotides were computationally designed with a random 32-base barcode region flanked by a universal 19-base primer region to uniquely identify each polymerase. The synthetic template DNA (IDT, Coralville, IA) was circularized using CircLigase II (EpiCentre, Madison, WI), treated with Exonuclease I (NEB, Ipswich, MA) to remove any linear template that was not covalently closed and subsequently column-purified. As an alternate strategy for circularization, the same sequencing primer was used as a splint to join the ends of the template. Since the primer spanned about ten bases on each end of the template, T4 ligase was then used for ligation and circularization. Unligated linear ssDNA template, excess primer and double-stranded DNA (formed hairpins) were digested with Exonuclease I and III treatment. The resulting primer-annealed circular DNA template was concentrated, desalted and recovered by isopropanol precipitation or by column purification (Zymo Oligo Clean and Concentrator, D4060). The pellet was re-suspended in water and column purified to remove any residual ATP from the previous ligation step. This method yielded high concentrations (>10-fold as compared to the CircLigase method) of the starting template/primer complex and hence the template:polymerase:pore ratio in the final reaction could be scaled up accordingly. The primer (5'-ATTT-TAGCCAGAGTGGGGA-3') was then annealed to the circularized barcoded template by heating to 95° C. for 3 min followed by cooling to 20° C. at a rate of 0.1° C./s.

For the high throughput multiplex experiments described herein (see Examples 8 and 9) a set of 96 unique barcoded ssDNA templates were computationally designed and ordered (IDT, Coralville, IA). The 32-base barcoded regions were constructed such that when any one of the templates was locally aligned to all other templates in the full set, the calculated sequence identity was always <85% to make them act as unique identifiers. They were then either divided into three individual sets (set 1=CBT 1 through 32; set 2=CBT 33 through 65 and set 3=CBT 66 through 96), wherein each set consisted of 32 templates or all 96 templates were pooled together. Each of these sets of 32 or the 96 pooled templates were circularized, primer-annealed and then complexed with a unique polymerase. Each set complexed with a unique polymerase was then incubated with the 1:6 pore overnight, diluted to 2 nM final concentration and loaded onto the chip.

*Clostridium* phage φCPV4 DNA polymerase (GenBank: AFH27113.1) was used as wild-type. Proprietary site-specific mutations were introduced to the DNA polymerase gene by site-directed mutagenesis (Roche Sequencing Solutions, Santa Clara, CA) to enhance the kinetic properties of the polymerase utilizing polynucleotide tagged nucleotides to approach native nucleotide incorporation characteristics.

Purified polymerase and the desired template were bound to the pore by incubating 0.1 M polymerase and 0.1 M of primer-annealed circularized DNA template per 0.1 M of 1:6 pore overnight at 4° C. For the spike-in experiments to test template replacement (see Example 5 herein), 2-fold molar excess of the desired template was incubated with the polymerase and then incubated with 1:6 pore overnight before loading onto the chip.

Example 2A—Nanopore Experiments Data Acquisition

Synthetic lipid 1,2-di-O-phytanyl-sn-glycero-3-phosphocholine (Avanti Polar Lipids, Alabaster, AL) was diluted in tridecane (Sigma-Aldrich, St. Louis, MO) to a final concentration of 15 mg/mL. A planar lipid bilayer was formed on the CMOS chip surface as described herein (see also Stranges, P. B. et al. Design and characterization of a nanopore-coupled polymerase for single-molecule DNA sequencing by synthesis on an electrode array. Proc. Natl. Acad. Sci. (2016). doi:10.1073/pnas.1608271113). Sequencing experiments were performed in asymmetric conditions. The cis compartment was filled with a buffer containing 300 mM KGlu, 3 mM MgCl2, 10 mM LiCl, 5 mM TCEP and 20 mM HEPES pH 8.0 and the trans compartment with 380 mM KGlu, 3 mM $MgCl_2$ and 20 mM HEPES pH 8.0, in which MnCl2 is a catalytic cation source during the polymerase extension reaction to initiate and sustain sequential nucleotide additions along the template DNA. Purified porin-polymerase-template conjugates were diluted in buffer to a final concentration of 2 nM. After pumping a 10 µL aliquot to the cis compartment, single pores were embedded in the planar lipid bilayer that separates the two compartments each containing ~5 µL of buffer solution. Experiments were conducted at 27° C. with 10 µM tagged nucleotides added to the cis well.

Example 2B—Data Acquisition

The ionic current though the nanopore was measured between individually addressable platinum electrodes coupled to a silicon substrate integrated electrical circuit. This consisted of an integrating patch clamp amplifier (Roche Sequencing Solutions, Santa Clara, CA), which provided a non-faradaic AC modulation with a rectangular wave (Vmax=+220 mV, Vmin=−10 mV) with a 40% duty cycle at 50 Hz applied across the lipid bilayer in voltage clamp mode. Data were recorded at a 2 kHz bandwidth in an asynchronous configuration at each cell using circuit-based analog-to-digital conversion and noise filtering (Roche Sequencing Solutions, Santa Clara, CA), which allows independent sequence reads at each pore complex. During the various experimental steps, a precision syringe pump (Tecan, Mannedorf, Switzerland) was utilized in an automated fashion to deliver reagents into the microfluidic chamber of the CMOS chip at a flow rate of 1 µL/s. Software control was implemented in Python, which interfaced with the pump via an RS 232 communication protocol.

Example 2C—Raw Read Quality

To filter out quality raw reads for barcode identification, the cumulative BMPI of all three polymerase variants were generated as function full barcode iterations. It was observed that, in general, as the read length increases the BMPI of the barcodes asymptotically increases up until 10, 14 and 20 iterations for RPol1, 2, and 3 respectively. As a conservative approach, raw reads were considered with at most 10 full iterations for barcode identification, while the rest of the other sequences where discarded in the downstream analysis pipeline.

Example 2D—Classification of Barcodes

Ionic current events were converted to raw reads using a commercial probabilistic base-calling algorithm (version 2.9.2, Roche Sequencing Solutions, Santa Clara, CA). Quality raw reads then were fed as input to a Smith-Waterman (SW) alignment-based barcode classification algorithm, which outputs a probability score, barcode match probability index (BMPI), describing the relative measure of how uniquely a barcode can be identified compared to the other possible barcodes in the measurement set. More specifically, the first step was to classify the different regions in the raw circular reads into barcode reads. This was achieved by locally aligning the raw read sequence to the known concatenated barcode sequence. Once all barcode iteration boundaries were identified, we utilized the multi-align function from the Bioinformatics Toolbox of MATLAB (2017a, MathWorks, Natick, MA) to perform a progressive multiple alignment of the repeated barcode sequences. Next, we generated the consensus sequence of these multiple aligned reads using "seqconsensus," which is subsequently locally aligned to all potential barcodes in the experimental set. Finally, the maximum scoring (SW) alignment identified the most likely barcode candidate, which was evaluated based on the particular input sequence. This score is defined as the BMPI and is used to measure the barcode identification probability with possible range of [0,1], where 0 means total mismatch and 1 denotes a total match. For all alignments, homopolymer sequences in the template, and repeated base calls of the same nucleotide in the raw sequencing reads were considered a single base.

In some embodiments, the use of circular barcodes (such as where the entire barcode is unique) helps to correct for any nanopore sequencing inaccuracies by reading the barcode multiple times in a row, which is utilized to generate a consensus barcode. This consensus barcode may be considered a "template" to compare to all other possible barcodes present in the sequencing run. For those embodiments employing circular templates composed of a Common Reading Region (CRR) and a molecular barcode, the derivation of a probability score will be the same. In this case, the user will have a choice to use the entire template (CRR+barcode) or only the "true" barcode region for consensus generation. In general, the CRR will assist in determining the barcode iteration boundaries.

Example 3—Sequencing of Unique Templates

To test if circular templates could be identified using a polymerase-nanopore system, three synthetic single-stranded DNA (ssDNA) molecules consisting of a unique 32-base barcode region flanked by a common 19-base primer region were constructed (see Example 1). All circular barcoded templates (CBTs) met two design specifications, (1) all sequence identities were <85% when the templates were locally aligned to each other to make them act as unique identifiers, and (2) the structures were optimized to eliminate regions of high-base pairing probability after circularization. Three different φCPV4 DNA polymerase variants engineered by Roche Sequencing Solutions (henceforth referred to as RPol) were utilized, as set forth in Example 1. Porin-polymerase conjugates were complexed with each of the three unique circularized DNA templates (RPol:CBT), which were finally loaded onto the chip for nine separate sequencing runs. By way of example, the secondary structures of the barcodes had high base-pairing probability if their minimum free energy ("MFE") value was above −10 kcal/mol (e.g. as calculated by MATLAB script 'rnafold' with default settings). See also Wuchty, S., Fontana, W., Hofacker, I., and Schuster, P. (1999). Complete suboptimal folding of RNA and the stability of secondary structures. Biopolymers 49, 145-165; and Matthews, D., Sabina, J., Zuker, M., and Turner, D. (1999). Expanded sequence dependence of thermodynamic parameters improves prediction of RNA secondary structure. J. Mol. Biol. 288, 911-940, the disclosures of which are hereby incorporated by reference herein in their entireties.

Figure 9A:
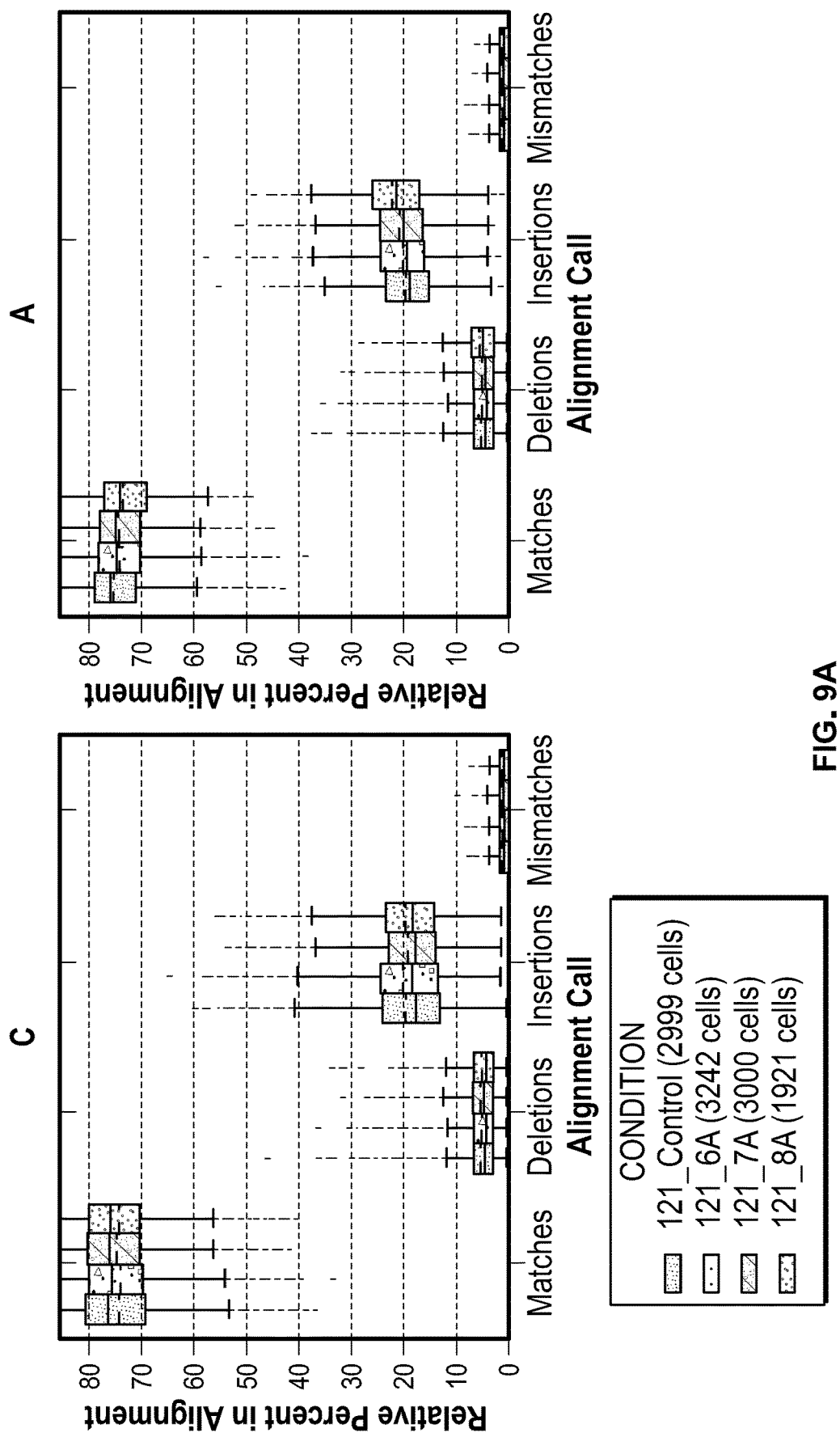
FIGS. 9A and 9B illustrate the sequencing results of three templates with the same nanopore complex. The data shows that when sequenced with the same nanopore complex (including a polymerase enzyme), the sequencing profile of the different barcoded templates is the same.
Figure 9B:
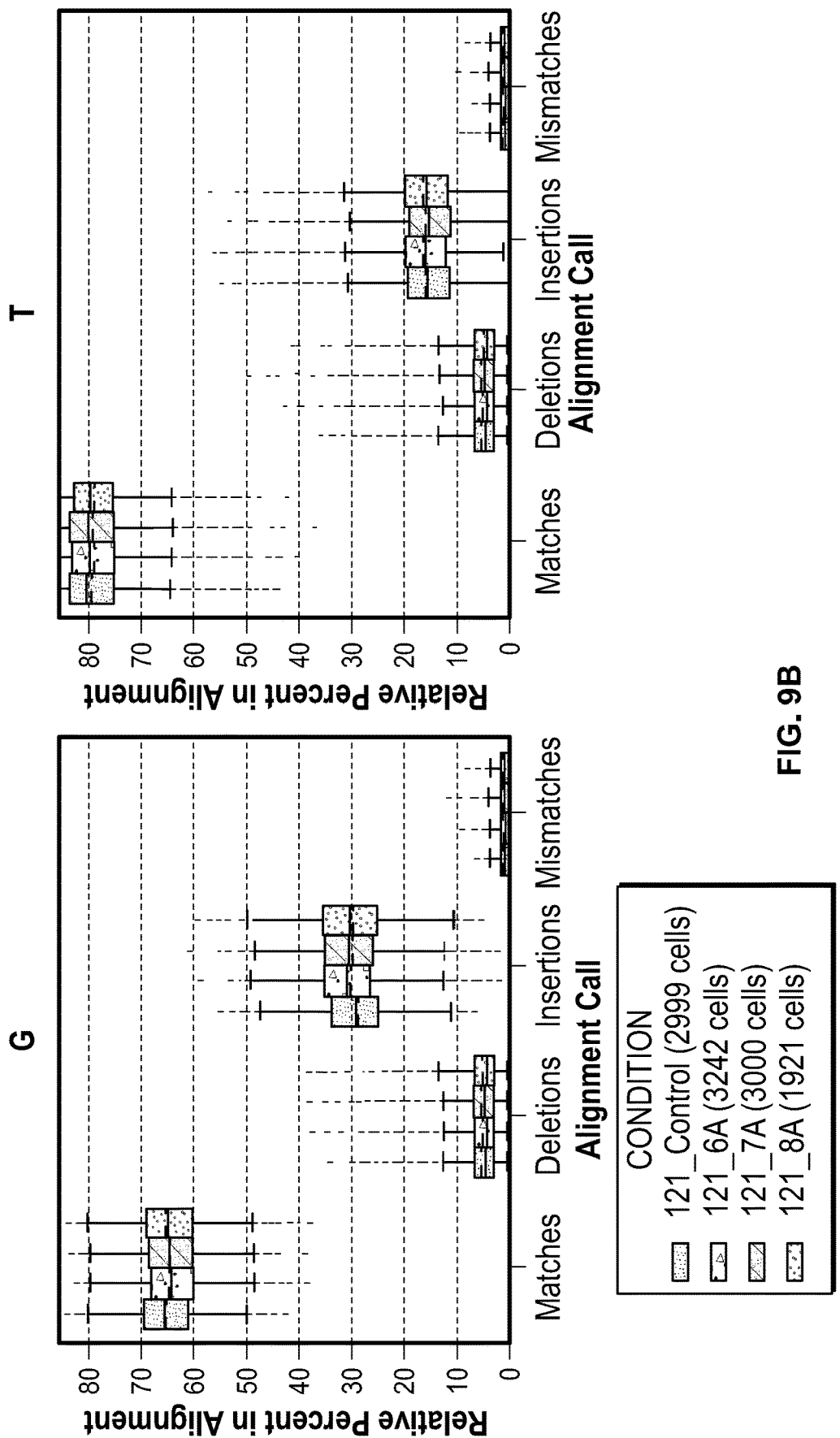

To measure current through the nanopore, a complementary metal-oxide-semiconductor (CMOS) chip containing thousands of individually addressable electrodes, which was developed by Roche Sequencing Solutions, was utilized. In this second-generation prototype, measurements were sampled at a frequency of 50 Hz with a 40% duty cycle by applying an AC waveform (+220 mV/−10 mV) across the channel, which enabled the repeated interrogation of the same, tagged nucleotide during incorporation (see Example 2). Sequential nucleotide additions were detected as continuous tag capture events associated with all four tagged nucleotides at characteristic current levels through the pore. Each tag generated a distinct and well-separated signal, uniquely identifying the added base. The recorded ionic current signal was converted to raw reads using a probabilistic base caller software developed by Roche Sequencing Solutions after data acquisition in offline mode. Over 1,000 quality raw reads for each RPol:CBT combinations were collected, and multiple full-iterations were observed around the circular templates. These results confirmed that polymerases could be loaded with circular templates and that the templates could be sequenced. Accordingly, template identification on the CMOS chip was shown to be feasible. FIGS. 9A and 9B illustrate that even though different nanopore sequencing complexes have different templates associated with an enzyme (here a polymerase), that each template may be distinguished and identified. These figures show the results of a nanopore sequencing assay (for each base C, A, G, T) using a control and three different polymerases, each polymerase associated with a different molecular barcode, respectively. The accuracy and kinetic profiles of the barcode templates were observed to be comparable when tested separately.

Example 4—Barcode Identification

Figure 3A:
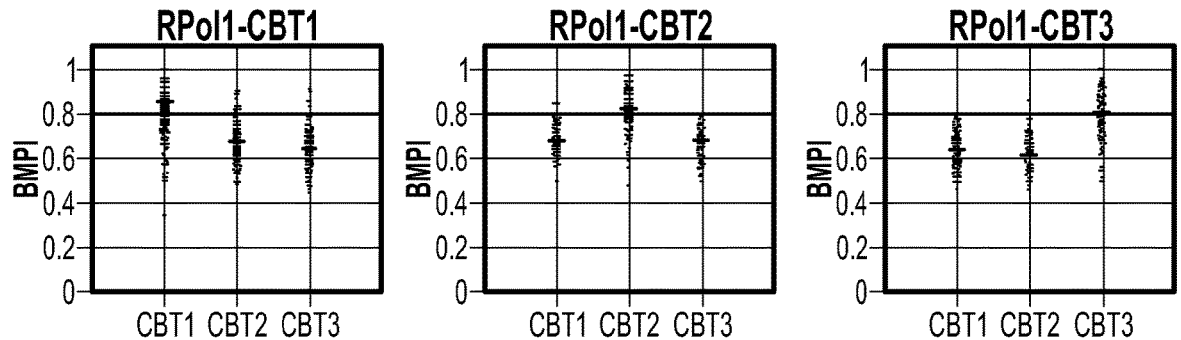
FIGS. 3A, 3B, and 3C illustrate barcode identification on a nanopore array. Barcode match probability index (BMPI) values of the three polymerase variants (FIG. 3A RPol1, FIG. 3B RPol2 and FIG. 3C RPol3) loaded with the three unique DNA templates (CBT1, CBT2 and CBT3) calculated by the alignment-based barcode classifier. In each of FIGS. 3A, 3B, and 3C, barcode classification is shown when the quality raw reads are aligned to the correct and incorrect barcodes. For every RPol:CBT combination, the mean barcode match probability index ("BMPI") value was >0.80 when the raw reads were compared to the correct template and <0.80 when compared to the incorrect ones. A line denotes the 0.8 BMPI cutoff. On each boxplot, the central mark indicates the mean, and the bottom and top edges of the box indicate the 25th and 75th percentiles, respectively.
Figure 3B:
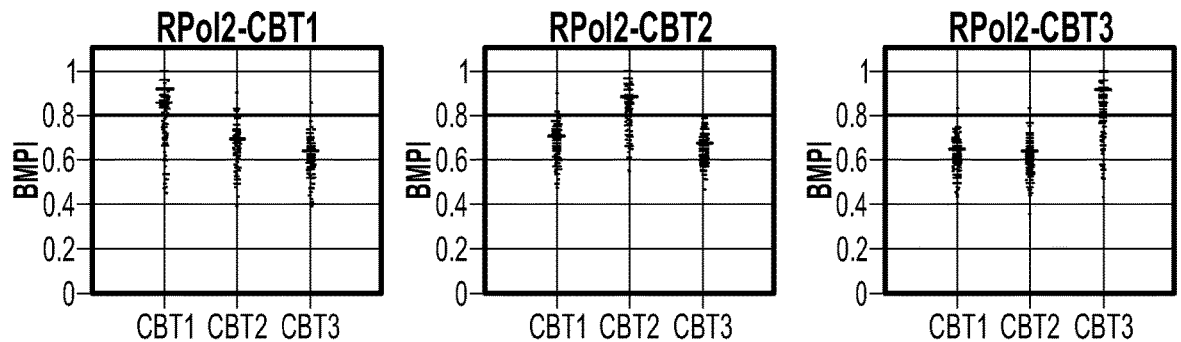
Figure 3C:
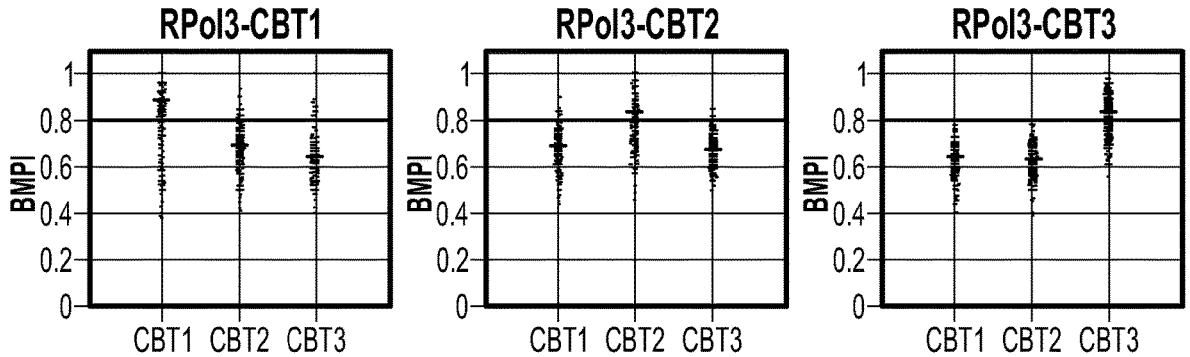

To demonstrate the suitability of barcode identification, a Smith-Waterman alignment-based barcode classification algorithm was utilized which computed a probability score, defined as barcode match probability index (BMPI), that described the relative measure of how uniquely a barcode could be identified compared to the other possible barcodes in the measurement set. First, quality reads were filtered out by requiring their read length to be greater than one full barcode iteration (51 base) and their consensus sequence length to be greater than 10 base. Then, we used this classifier to analyze the RPol1:CBT1 sequencing data for estimating the accuracy with which one could identify the loaded barcoded DNA template. When the filtered raw reads were compared to the correct template (CBT1), the mean of the calculated BMPI values was 0.85 (see FIG. 3A, left panel). In contrast, when the same reads were aligned to the incorrect templates (CBT2 and CBT3), there average BMPI values decreased to ~0.65 (FIG. 3A, left panel) Using this barcode identification strategy, a similar classification was performed with the same polymerase variant bound to two other circular templates, analyzing the RPol1:CBT2 and RPol1:CBT3 sequencing data sets, respectively. For both cases, the mean BMPI value was >0.80 when the raw reads were compared to the correct template and <0.80 when compared to the incorrect ones (FIG. 3A, middle and right panels). Similarly, as shown for CBT1, both CBT2 and CBT3 uniquely identified the polymerase variant based on the sequencing alignment metrics established above. Next, sequencing datasets for the other two porin-polymerase variants (RPol2, RPol3), each loaded with the three unique circular DNA templates, were similarly classified as for RPol1 described above. For all cases, the barcoded templates loaded on the polymerase variants (FIGS. 3B and 3C) were successfully identified. To further test the viability of the classifier, it was determined that when the BMPI value was >0.80 for a particular raw read, there was only ~2% probability of misidentifying the barcode by computing a confusion matrix. For this reason, 0.8 BMPI was selected as the threshold value to identify barcodes with high confidence. This evidence demonstrates that when reads >50 bases were obtained, the template bound to the polymerase could be identified based on the BMPI value.

Example 5—Barcode Replacement

After confirming that DNA templates loaded on each polymerase could be identified on a CMOS chip, it was determined whether a template could be replaced with a different template once the porin-polymerase-template complex was formed. To test this hypothesis, the RPol2:CBT2 complex was assembled, which was subsequently loaded onto the chip for four different sequencing runs. First, a control run was carried out, in which only the tagged nucleotides were added after pore insertion. By employing the barcode classifier described herein, it was determined that when the raw sequencing reads were compared to the correct template (CBT2), the mean BMPI value was 0.85. In contrast, when the same reads were aligned to the incorrect template (CBT1), this value decreased to ~0.70. As shown before, this confirms that 0.8 BMPI could be used as a threshold value for barcode identification. Next, in the second set of experiments, a 5-fold molar excess of a secondary barcode (CBT1) was spiked in immediately after the porin-polymerase-template assembly, which mimicked a multiplex scenario with a set of barcodes present in the same reaction volume during assembly. In two separate experiments, this complex was inserted into the membrane after a brief (<5 min) and after an overnight (~12 hr) incubation period, which provided two different time durations for the added secondary template to replace the primary template already bound to the porin-polymerase. Then, tagged nucleotides were added for the subsequent sequencing reaction. For both cases, the mean BMPI value was >0.80 when the raw reads were compared to the correct template and <0.80 when compared to the incorrect ones. The results demonstrate that, even, after an overnight incubation with a second barcode, no barcode replacement took place. Additionally, the possibility of on-chip barcode replacement was tested, which mimics a high-throughput scenario with multiple barcodes present in the same reaction volume in the cis chamber of the CMOS chip. In this last experiment, when a second barcode (CBT1) was spiked in along with the tagged nucleotides after pore insertion, the barcode classification results indicated that the polymerase variants were uniquely labeled with their respective barcodes. Again, the mean BMPI score was above and below the threshold value of 0.80 for the correct template (CBT2) and incorrect template (CBT1), respectively. This confirmed that once a polymerase is loaded with a barcode it was not replaced by another template. The large number of quality raw reads in a single run coupled with the ability to assign a unique barcode to a particular polymerase variant provided the confidence that multiple polymerases could be screened and that the different templates loaded on each polymerase could be distinguished. FIGS. 8A-8D illustrates that for three different polymerases tested, that the templates associated with the polymerases did not exchange even after the complexes were mixed together. These figures show the results of a nanopore sequencing assay demonstrating that the barcoded templates can be used to distinguish different polymerase kinetics on the same sequencing chip. Two different enrichment strategies (intra- and post-) were used for each set of three polymerases but no difference was observed.

Example 6—Kinetic Properties of Polymerases

Figure 4B:
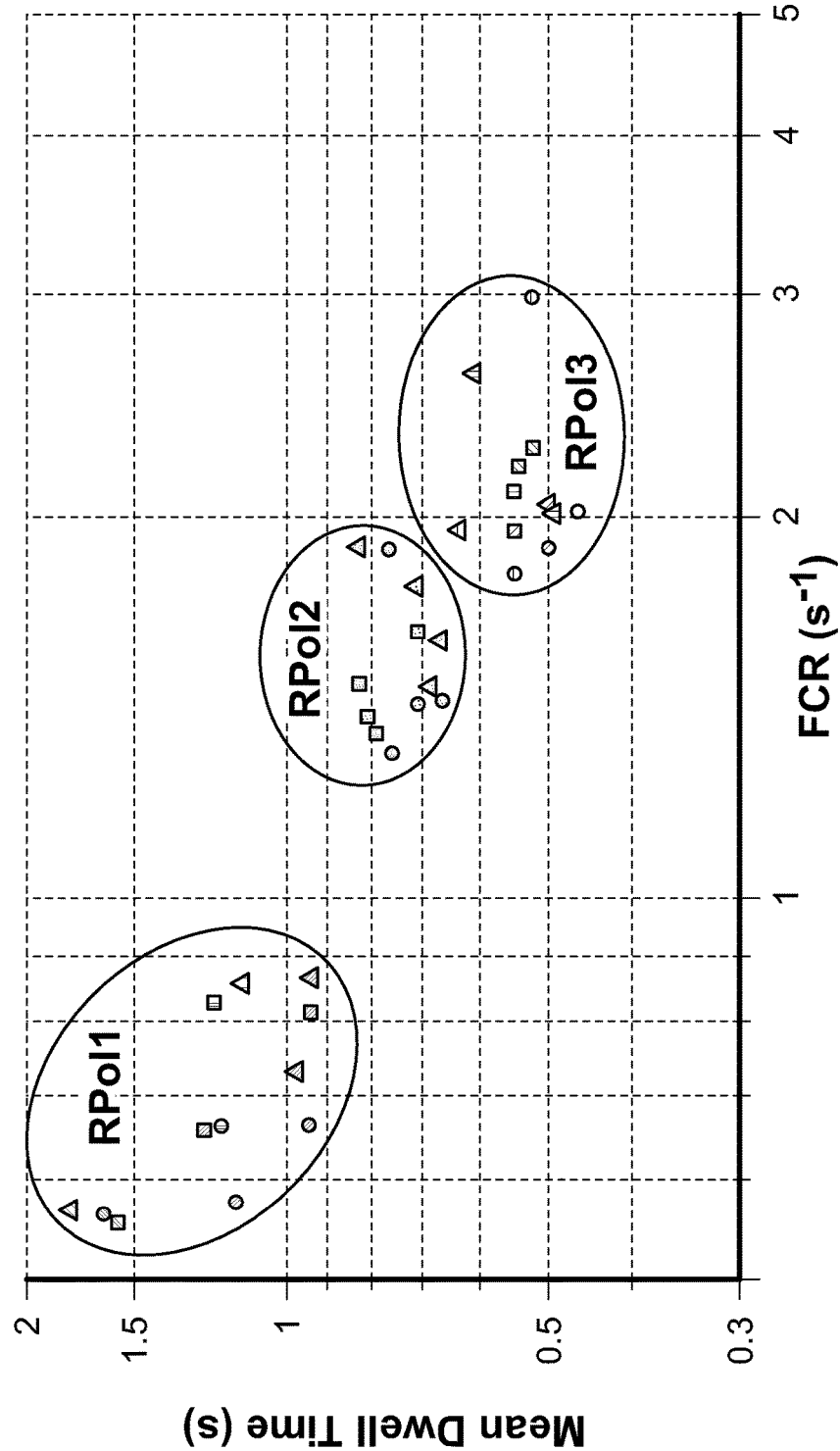
FIG. 4B illustrates polymerase variant kinetics, where each dot represents the mean catalytic rate of tagged nucleotide incorporation (FCR) and mean dwell time (tdwell) value pair corresponding to each of the RPol:CBT combinations set forth in FIGS. 3A, 3B, and 3C for each of the four (A, C, T, and G) nucleotides (3×3×4=36 total dots). The different shaped markers correspond to CBT1 (■), CBT2 (●) and CBT3 (▲) barcodes, respectively. Each of the kinetics properties are independent of template context, and unbiased for the four tagged nucleotides.
Figure 5A:
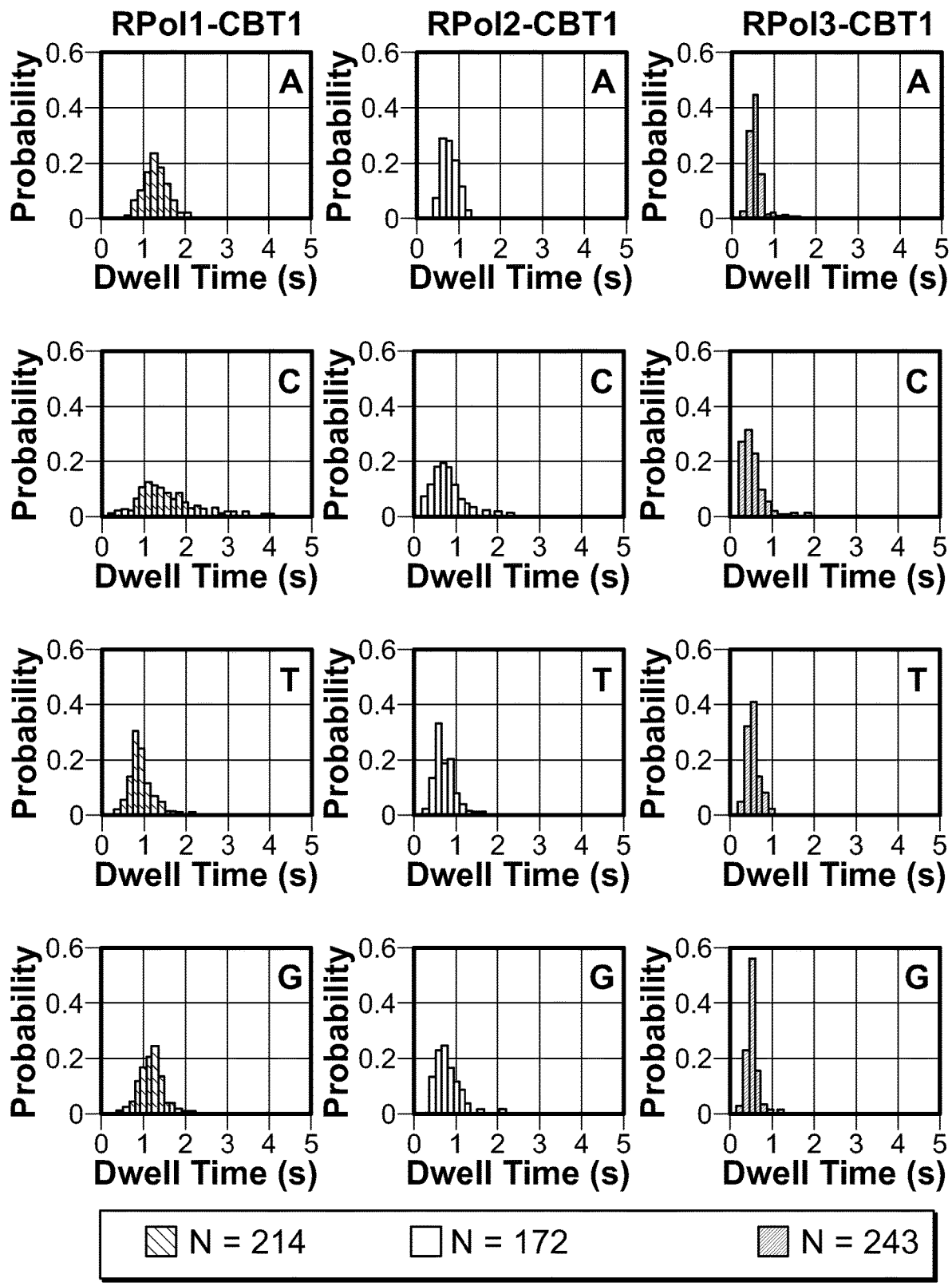
FIGS. 5A, 5B, and 5C illustrate the mean dwell time distribution of each of the four tagged nucleotides for each of the three polymerases (RPol1-3) loaded with circular barcoded template (CBT) 1 (FIG. 5A), CBT2 (FIG. 5B), and CBT3 (FIG. 5C). The figures illustrate that the distributions do not differ from barcode to barcode. This demonstrates that dwell time, a polymerase-associated kinetic property, is independent of barcode choice. On the other hand, for each polymerase variant, the mean dwell time is different: centers around 1.3, 0.7 and 0.5 s, respectively. Thus, dwell time is a kinetic property that could be used to distinguish polymerase variants.
Figure 5B:
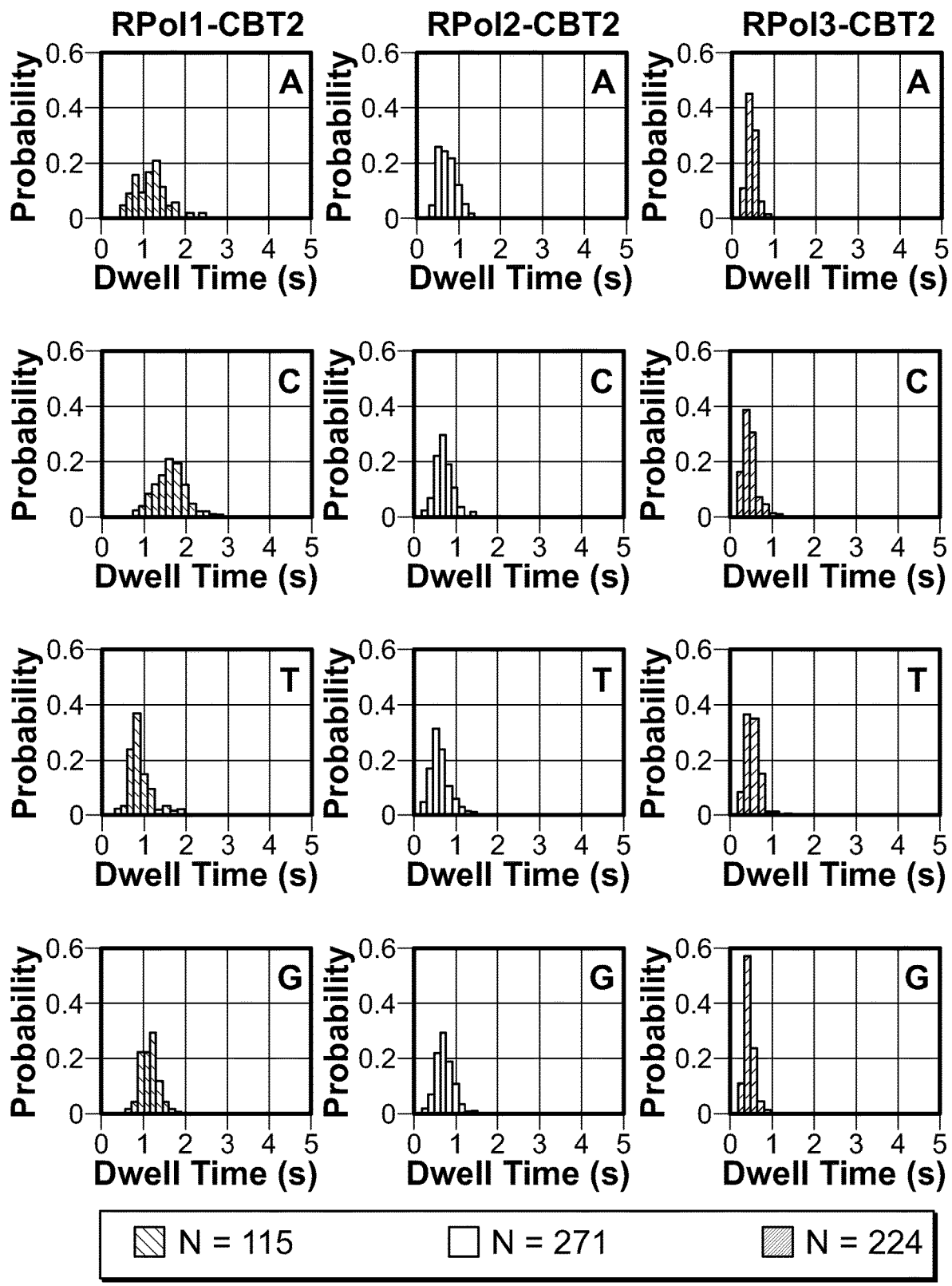
Figure 5C:
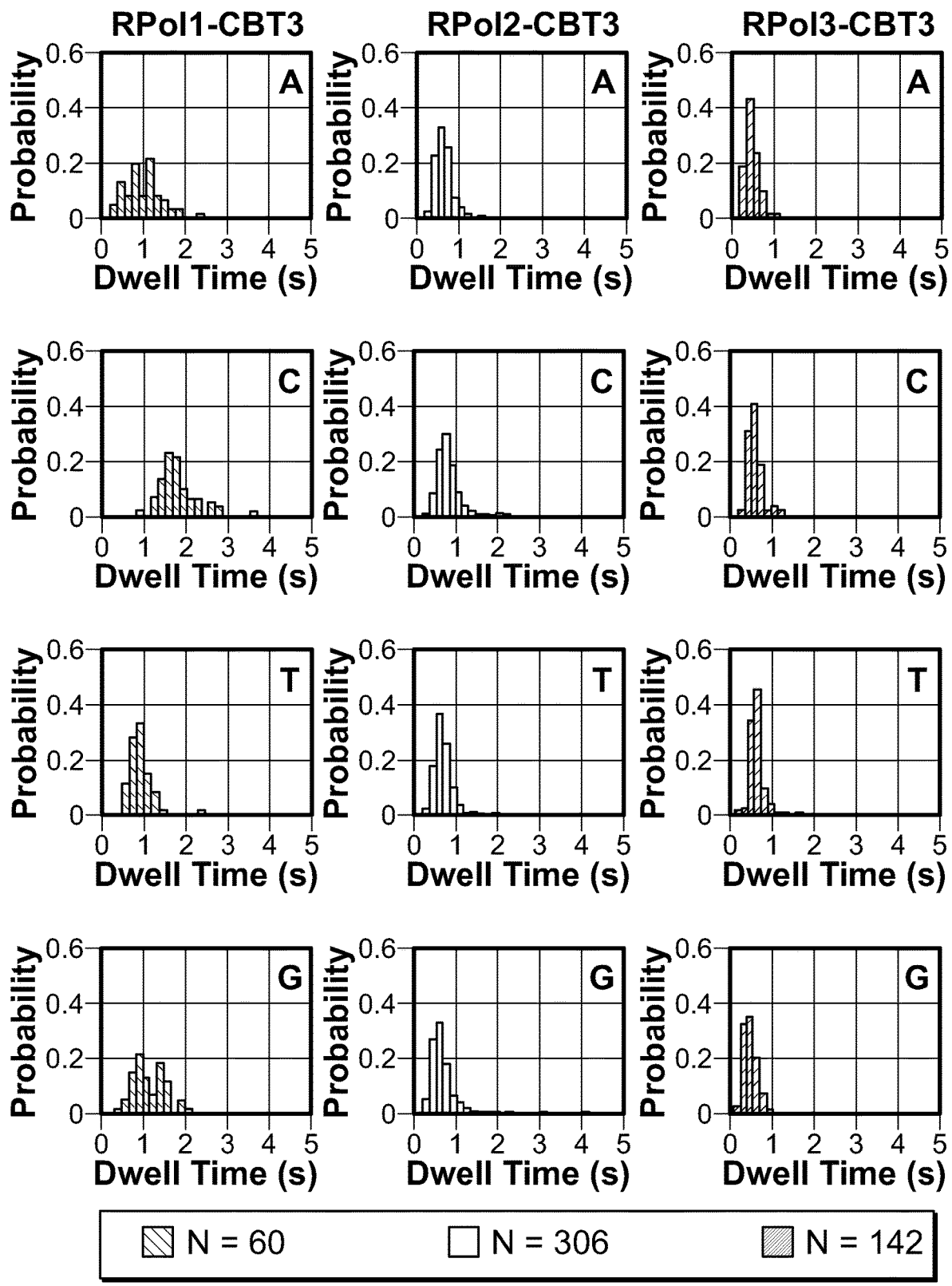

A variety of kinetic parameters related to tagged nucleotide incorporation and tag capture during a base call can be derived from the electrical signal produced by single-molecule events. Here, dwell time was defined as the time duration for a distinct base call, which is a function of all kinetic steps after tagged nucleotide binding to the ternary complex and up to tag release, and the rate of a full catalytic cycle of tagged nucleotide incorporation as FCR (FIG. 4A). As an initial test, these kinetic parameters were calculated for each of the three polymerase variants loaded with a unique CBT from the already collected sequencing data shown in FIG. 3A-3C. When comparing the three different polymerase mutants each loaded with the same template, it was determined that the mean FCR was ~0.6 s−1 for RPol1, ~1.4 s−1 for RPol2 and ~2.0 s−1 for RPol3 for all of the four bases (A, C, T, and G) regardless of the sequence context of the loaded DNA template (FIG. 4B). Similarly, analysis of the mean dwell time of the tagged nucleotide captures were also independent of barcode content with computed values of ~1.3 s for RPol1, ~0.7 s for RPol2 and ~0.5 s for RPol3, respectively (FIGS. 5A, 5B, and 5C). These results demonstrated that the kinetic parameters were statistically different for each of the polymerases variants and that they are independent of barcode sequence context (FIG. 4B). For this reason, sequencing data for each of the three polymerase variants loaded with different templates was lumped into the same dataset for downstream analysis. This allows us to classify polymerase kinetics based on template identification.

Example 7—Principal Component Analysis

Figure 6A:
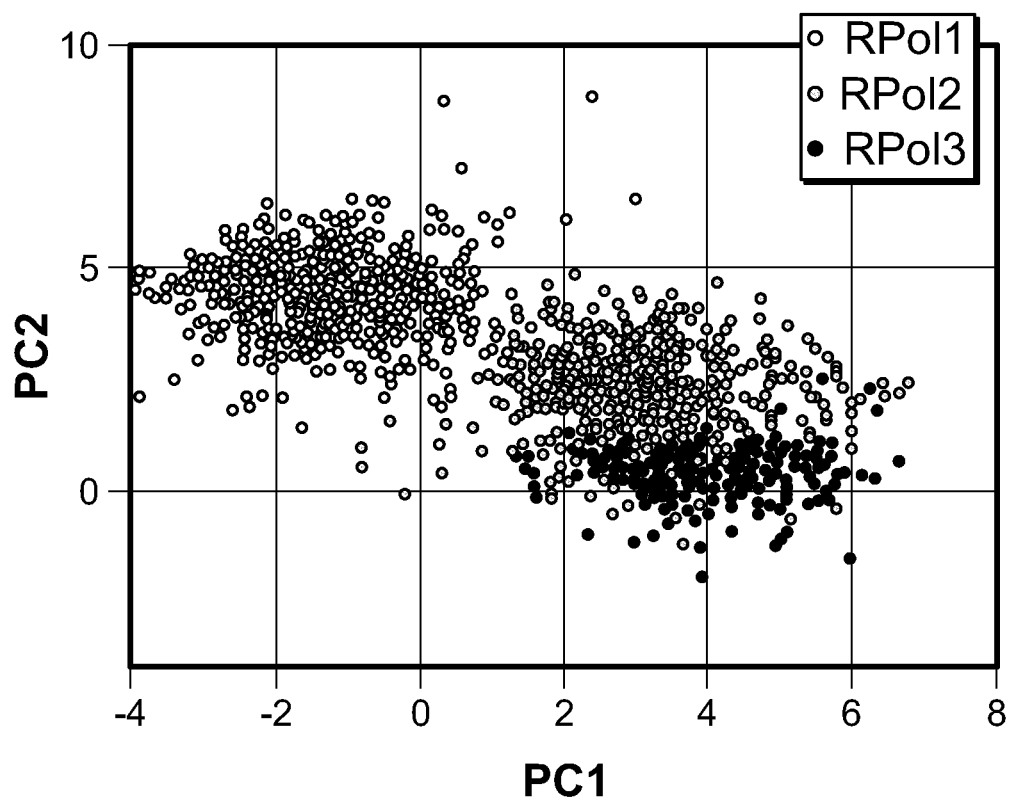
FIGS. 6A, 6B, and 6C illustrate principal component (PCA) analysis of polymerase variants. Each principal component is a linear combination of 20 kinetic parameters derived from single-molecule tagged nucleotide capture data. The PCA-based 2D projections onto the first three (FIGS. 6A, 6B, and 6C, respectively) principal components showed great separations for each of the three polymerase variants. Data points on the plots were converted into a z score by centering and scaling of all data points for each principal component.
Figure 6B:
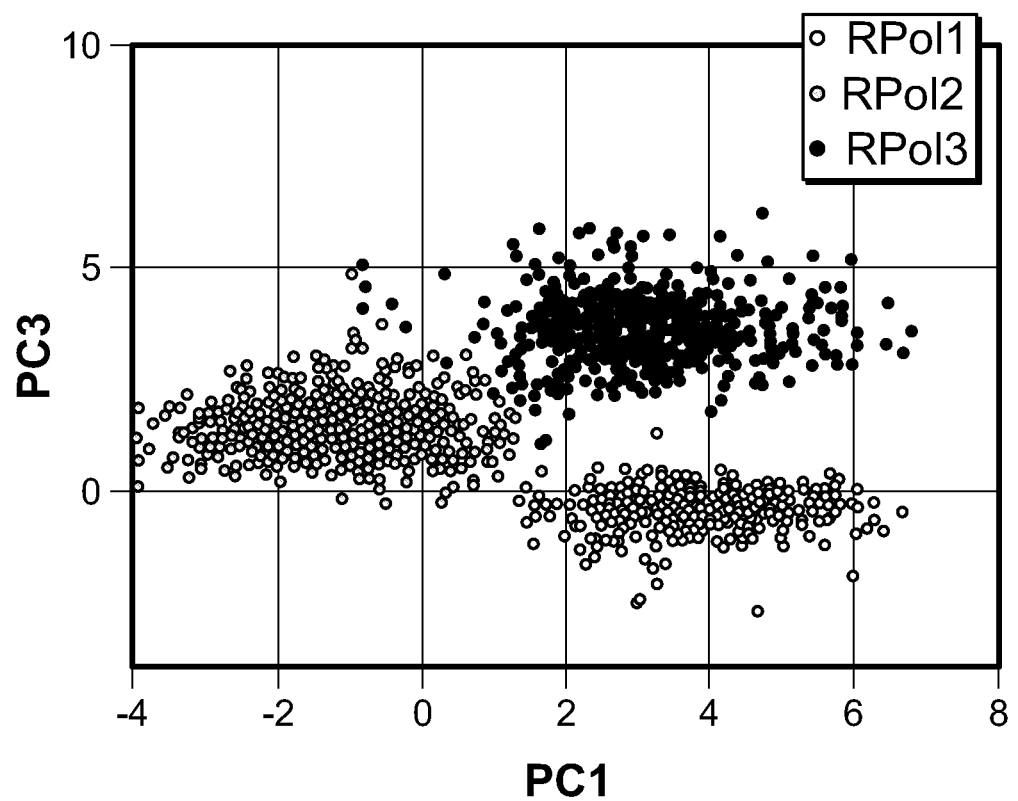
Figure 6C:
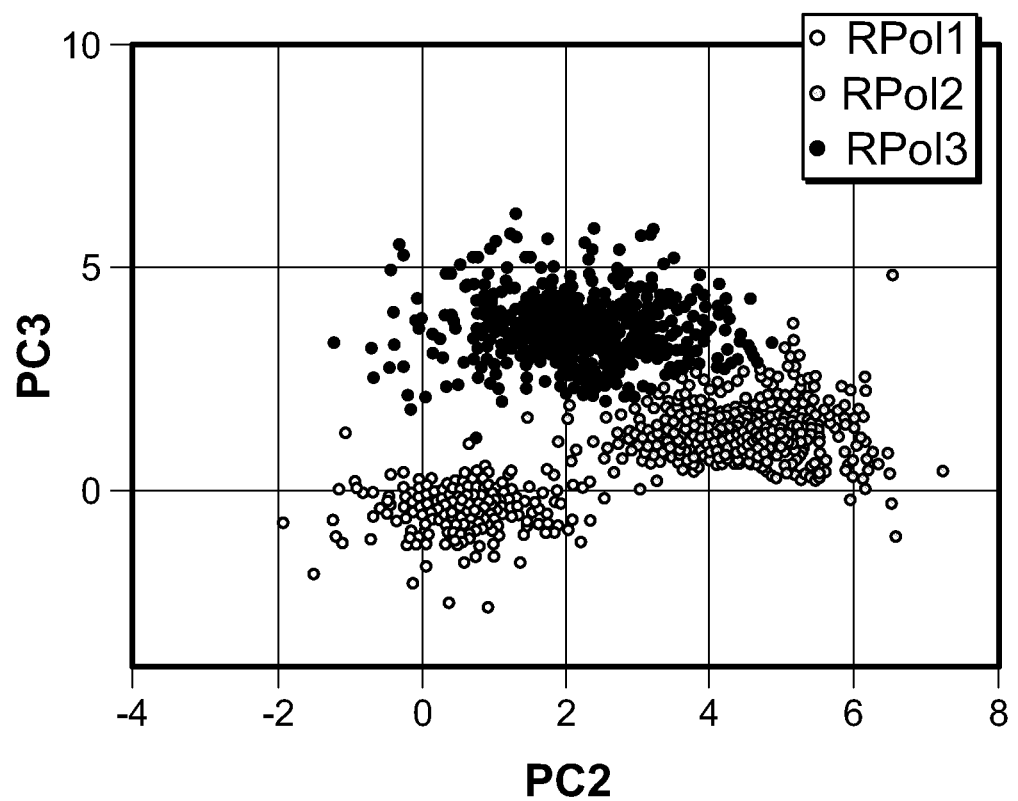

Since each polymerase variant had a unique set of kinetic parameters, this opened up the potential for directly distinguishing them among a variety of polymerase mutants using sequencing on the nanopore array. To evaluate this possibility, three additional kinetic parameters to be used in the principal component analysis (PCA) were defined, namely the tag release rate after nucleotide incorporation (TRR), tag capture rate (TCR) as the number of observed current blockade events during a base call per unit time, and tag capture dwell time (TCD) as the mean time duration for a distinct tag capture, i.e., a tag threading event during an AC capture period (FIG. 4A). Quality reads were filtered out by requiring their read length to be greater than one and less than ten full-barcode iterations. This threshold minimized the presence of inherently error-prone raw reads (generated during nanopore sequencing) in the downstream analysis. Then, PCA was used on the filtered sequencing data for each of the three polymerase variants based on 20 derived kinetic properties, i.e., five unique kinetic parameters for each of the four tagged nucleotides (see, for example, Table 1 below which shoes the PCA coefficients for Rpol1). The PCA-based 2D projections of the kinetic signatures for each polymerase onto the first three principal components showed distinct separation (FIGS. 6A, 6B, and 6C). Therefore, it was demonstrated that polymerase variants could be uniquely identified by using information from multiple kinetic parameters.

TABLE 1

Coefficients for the first three principal components for the 20 kinetic properties derived from the single molecule sequencing signal for RPol1. FCR: rate of a full catalytic cycle of tagged nucleotide incorporation, TRR: rate of tag release after nucleotide incorporation, tdwell: time duration for a distinct base call, TCD: mean time duration for a distinct tag capture, TCR: number of observed current blockade events during a base call per unit time. Capital letters in front of the kinetic parameter refer to each of the four tagged nucleotides. Each principal component is normalized such that all its coefficients sum up to one.

| Parameters | PC1 | PC2 | PC3 |
|---|---|---|---|
| A-FCR | −0.0206 | −0.9631 | −0.4112 |
| A-TRR | −0.0947 | −0.4064 | −1.0105 |
| A-tdwell | 0.1207 | 1.6877 | 1.2213 |
| A-TCD | 0.3154 | −1.3361 | −0.0786 |
| A-TCR | −0.0874 | 0.3182 | 0.0236 |
| C-FCR | −0.0419 | −3.2396 | 0.1876 |
| C-TRR | −0.0058 | −2.0477 | 0.2139 |
| C-tdwell | 0.1364 | 9.8689 | −0.6626 |
| C-TCD | 0.3054 | 0.3886 | −0.2051 |
| C-TCR | −0.0932 | 0.1037 | 0.0470 |
| G-FCR | −0.0148 | −1.8844 | −0.5146 |
| G-TRR | 0.0293 | −0.0477 | −0.1174 |
| G-tdwell | −0.0084 | 2.2122 | 0.6320 |
| G-TCD | 0.3606 | −2.5638 | −0.2139 |
| G-TCR | −0.1246 | 0.7211 | 0.0552 |
| T-FCR | −0.0399 | −2.0203 | −0.5606 |
| T-TRR | −0.0572 | 0.2610 | 0.0379 |
| T-tdwell | 0.0975 | 1.1657 | 0.3715 |
| T-TCD | 0.3277 | −1.6544 | −0.0719 |
| T-TCR | −0.1048 | 0.4362 | 0.0563 |

Standard principal component analysis was carried out using the pca function from the Statistics and Machine Learning Toolbox of MATLAB (2017a, MathWorks, Natick, MA). Input variables were scaled to have zero mean and unit variance and the resulting first, second and third principal component were determined from the entire dataset. To generate the principal component scatter plot (FIGS. 6A to 6C), all of the sequencing data for each polymerase variant was first projected onto these first three principal components. These values were then converted into a z score by centering and scaling of all data points for each principal component.

Example 8—Multiplex Polymerase Measurement

Examples 3 through 7 established the principle of barcoded-polymerase screening. In practice, one might want to these techniques in a directed evolution scheme to find a polymerase variant with the desired kinetic properties. As a proof of principle, the three nanopore-coupled polymerase variants were loaded with a unique ssDNA template using a random assignment (RPol1:CBT1, RPol2:CBT2 and RPol3:CBT3) in separate template binding reactions. Next, they were pooled in equimolar ratios and inserted into the CMOS chip for sequencing reactions. A computationally generated random 51-base sequence, and a second template, composed of a random 32-mer barcode region with the universal 19-base flanking priming site, was used as control templates. Utilizing our barcode classification algorithm, on average, we found higher BMPI scores above the threshold value of 0.8 when raw reads were compared to the (correct) templates loaded on the polymerases versus two random templates. Although, the mean BMPI values were ~0.70 for each RPol:CBT in this pooled experiment, high-confidence barcode identification was still possible as ~67% of the total raw reads were identified as any of the three barcodes, which were originally loaded onto the polymerase variants in the pooled, 3-plex sequencing experiment.

To explore the potential of high-throughput multiplexing, 96 synthetic unique barcoded ssDNA templates with same circular topologies as described for the "singleplex" experiments were designed. The 32-base barcoded regions were computationally constructed such that when any one of the templates was locally aligned to all other templates in the full set, the calculated sequence identity was always <85% to make them act as unique identifiers. The structures were not MFE-optimized as we have shown that the barcode classifier is independent of secondary structure differences. To further test these template designs for high-accuracy barcode identification, we implemented an in-silico algorithm which sampled 1,000 random quality reads from the "singleplex" sequencing experiments, which were subsequently classified by either comparing them to the experiment-specific (correct) template or to a randomly chosen template from our list of 96 sequences (incorrect template). When the randomly selected quality reads were compared to the correct template, the mean BMPI value was 0.85. In contrast, when the same reads were compared to randomly-selected templates from our list, there average BMPI value shifted below ~0.55. This in silico test demonstrated the feasibility of a uniquely identifiable polymerase-barcode assignment scheme.

Next, to evaluate these barcoded templates experimentally, nanopore-coupled RPol2 were loaded with these 96 unique CBTs, which were subsequently inserted into a lipid bilayer for sequencing experiments. Then, the classifier was used to analyze the RPol2:CBT1-96 sequencing data for estimating the accuracy with which one could identify each of the loaded CBTs in a single experiment. Each set of quality read obtained was compared to all of the 96 CBTs and a BMPI score was recorded. The maximum scoring BMPI value, which was above the 0.80 threshold, identified the most likely barcode candidate for each comparison. Reads with maximum BMPI value less than 0.80 were discarded from downstream analysis. All such classified barcodes were counted and displayed on a histogram. Using this classification scheme, a total of 94 barcodes out of 96 possible barcodes (98%) were uniquely identified by evaluating 1,067 quality raw reads. On average, the individual barcodes were observed at least 20 times during measurements. These observations were randomly distributed as expected by the stochastic nature of porin-polymerase-template assembly, and the complex insertion into the lipid bilayer before measurement 18. It was thus demonstrated that polymerase-bound barcoded DNA templates could be identified in a 96-plex fashion.

Figure 7A:
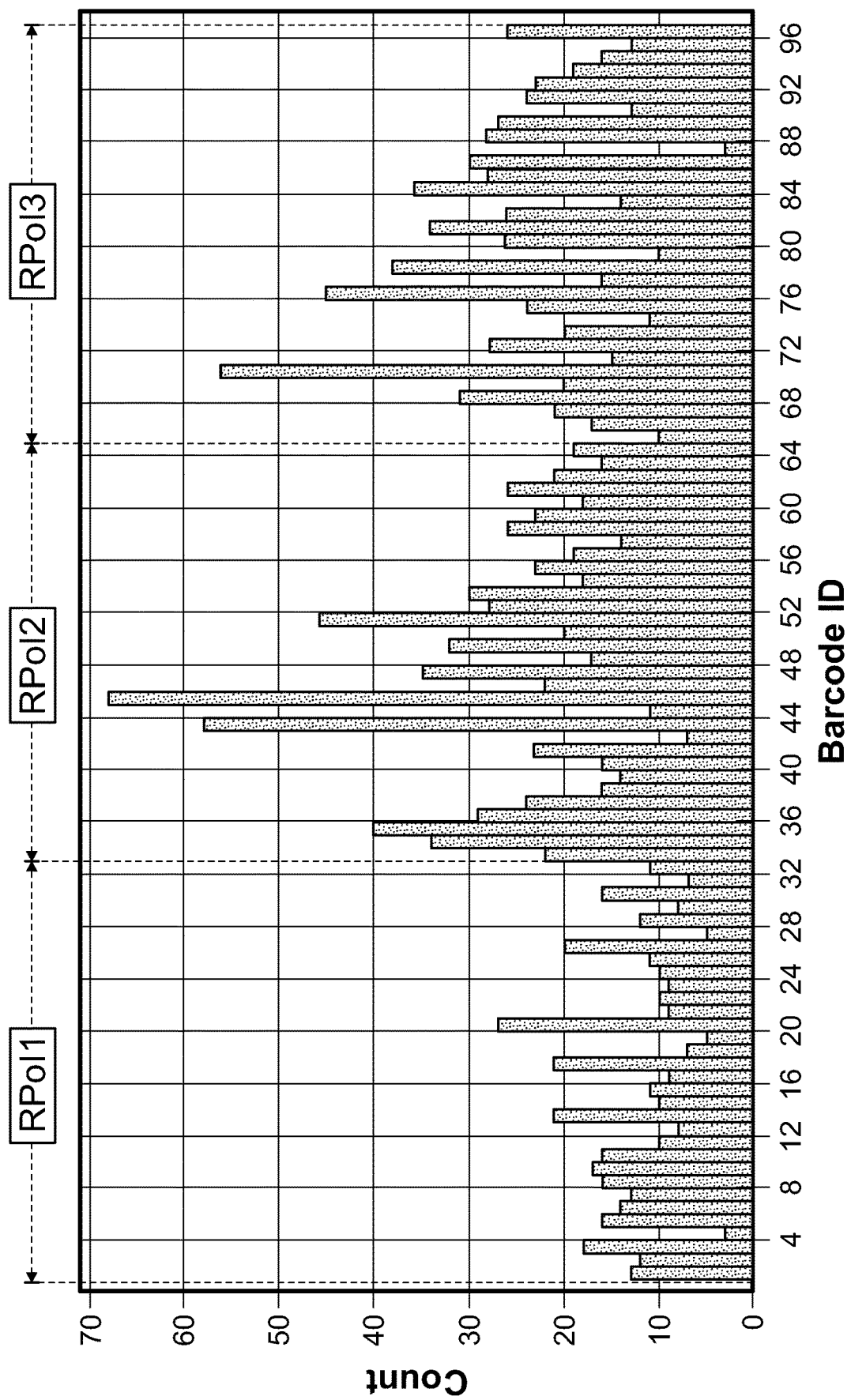
FIGS. 7A and 7B illustrate the distribution of experimentally observed barcodes for the three different polymerase variants (RPol 1, RPol2 and RPol3) in a multiplexed on-chip experiment. Circular barcoded templates (CBT) 1-32 were complexed with polymerase variant 1 (RPol1), CBT33-64 with RPol2, and CBT65-96 with RPol3.
Figure 7B:
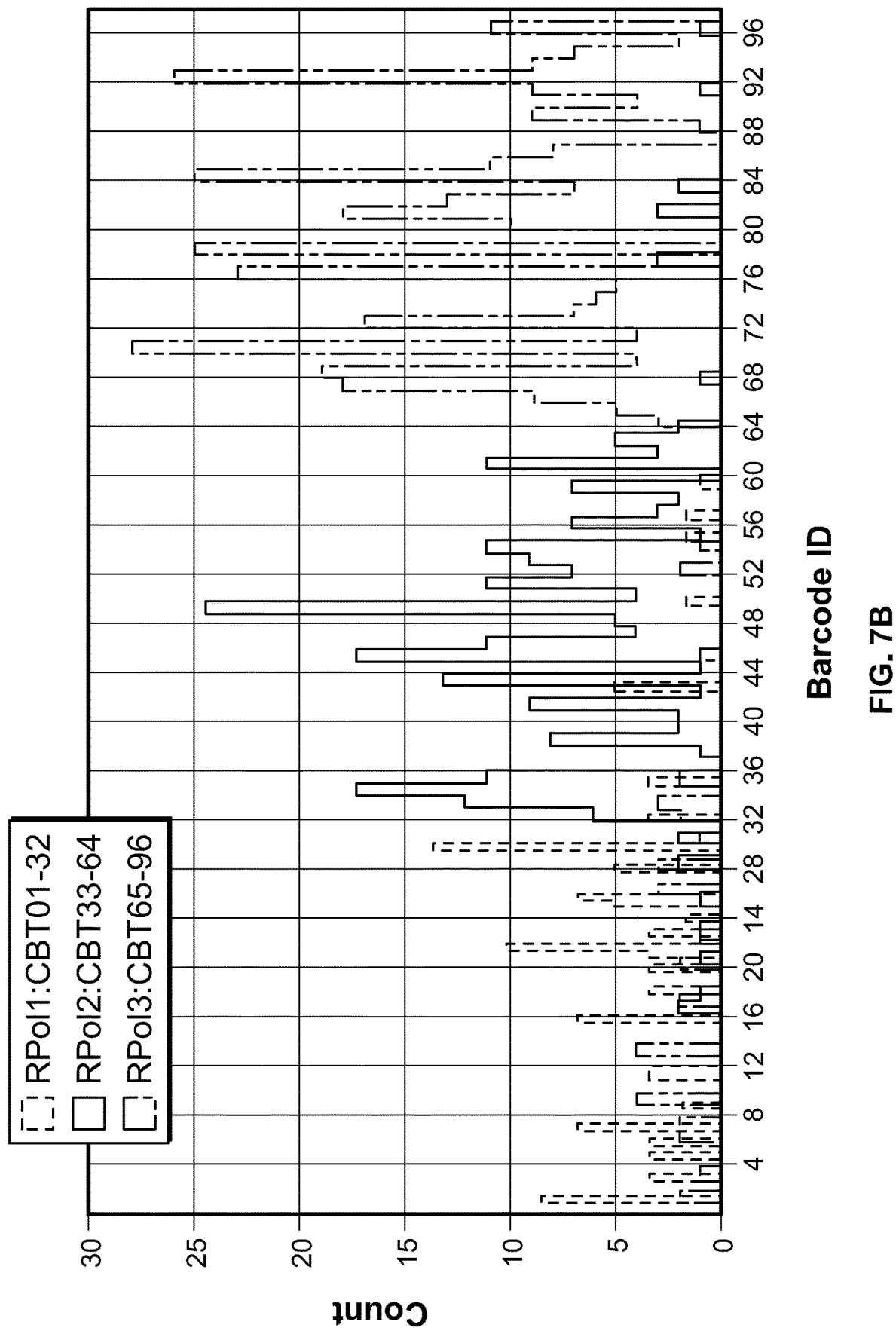
Figure 8A:
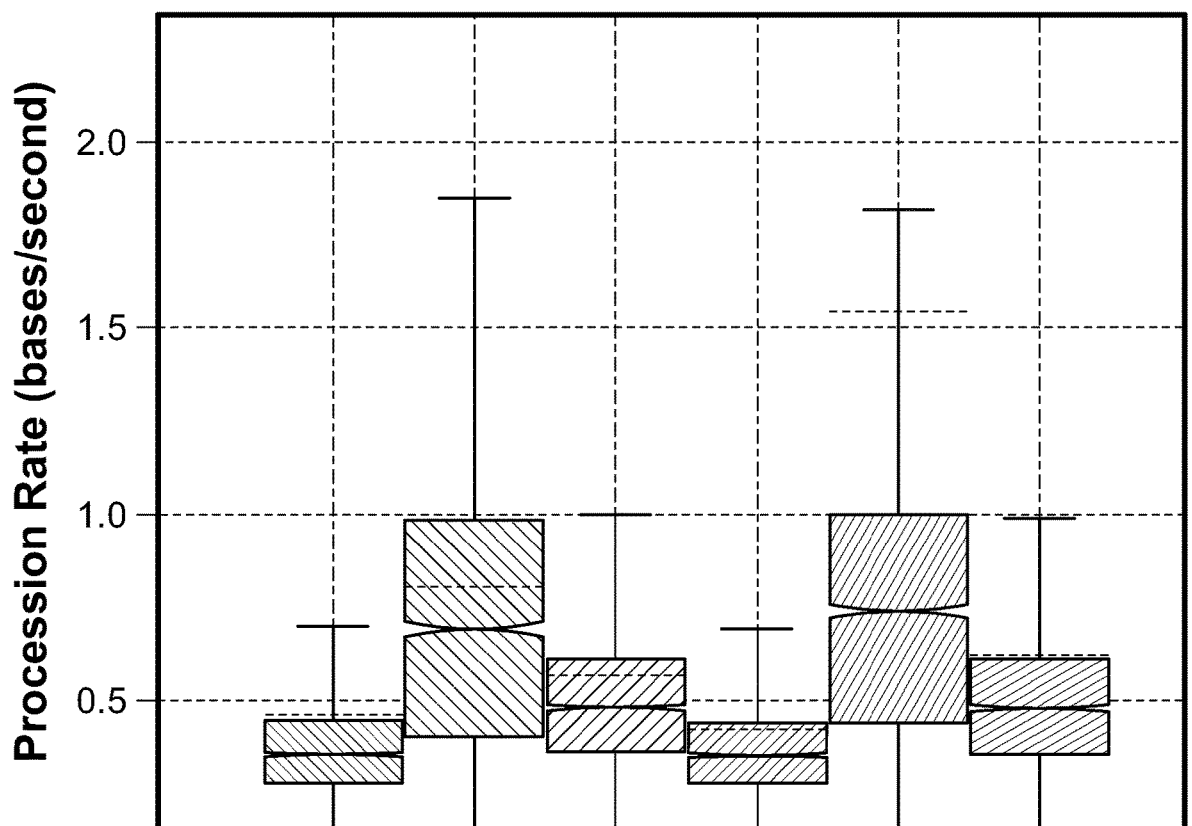
FIG. 8A illustrates that different procession rates may be observed for each polymerase variant tested, and further illustrates that even when different templates are mixed together (intra-enrichment or post-enrichment), the templates do not exchange once associated with a polymerase.
Figure 8B:
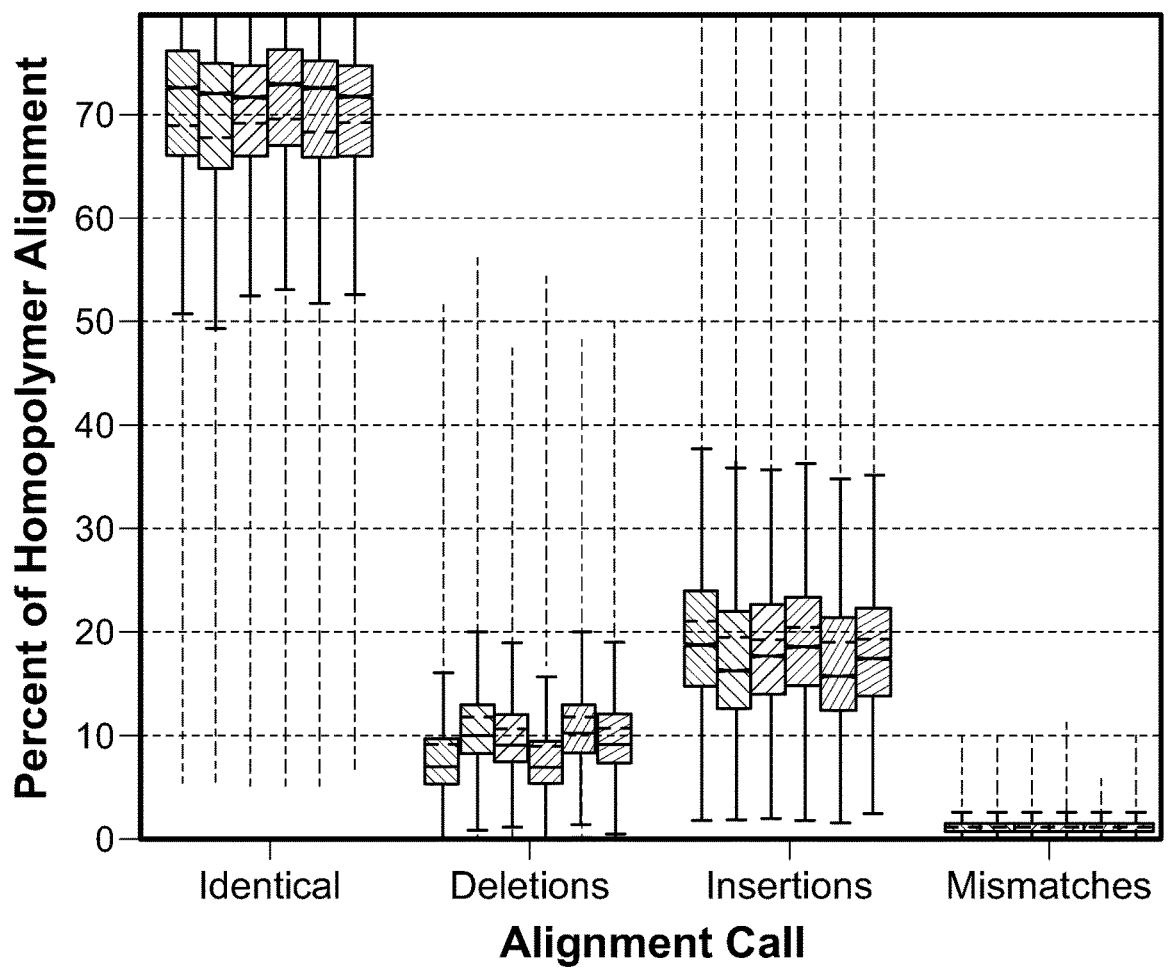
FIG. 8B illustrates that different homopolymer alignment profiles may be observed for each of the polymerase variants tested in a single experiment, and further illustrates that even when different templates are mixed together (intra-enrichment or post-enrichment), the templates do not exchange once associated with a polymerase.
Figure 8C:
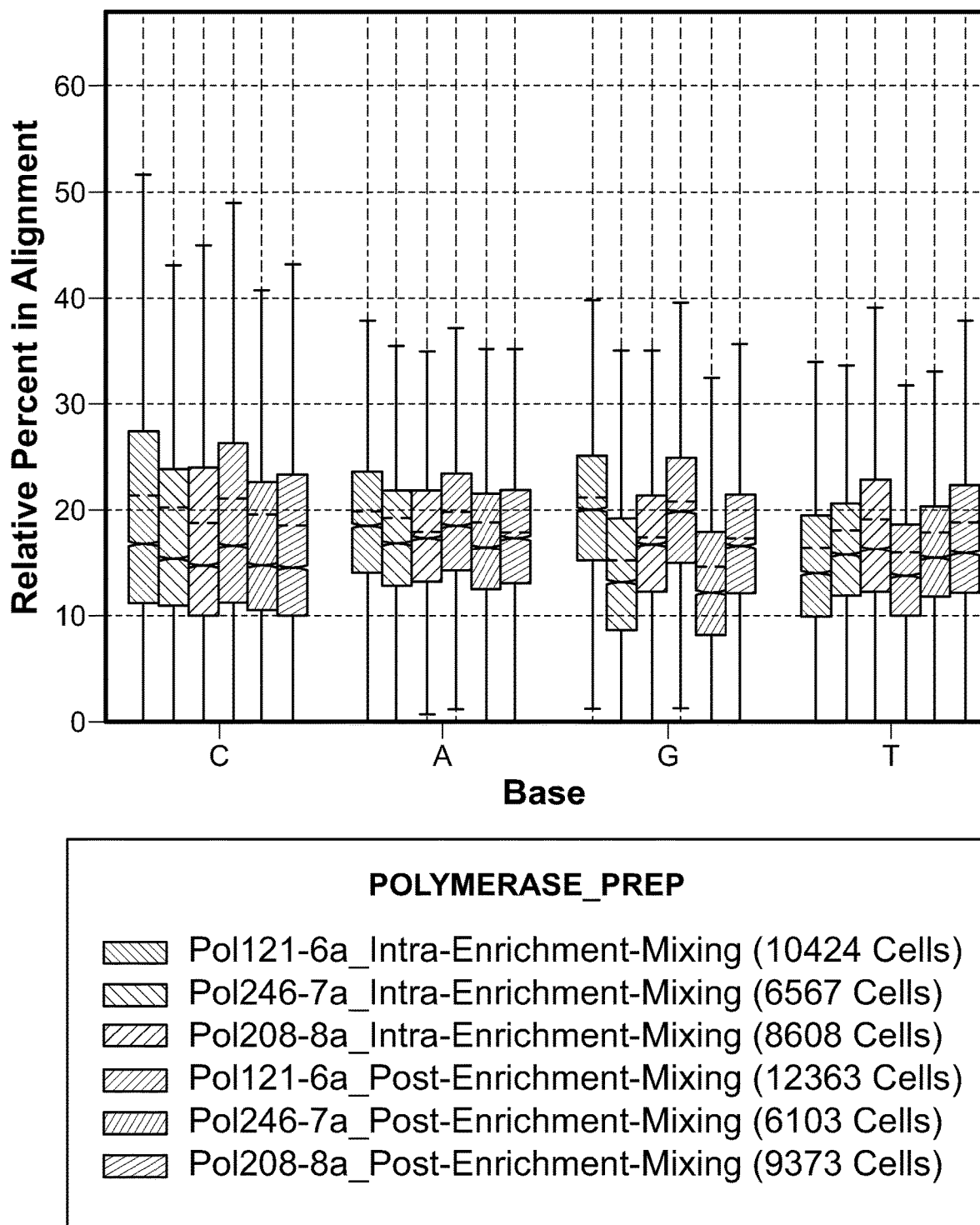
FIG. 8C illustrates that different insertion profiles by base may be observed for each of the polymerase variants tested in a single experiment, and further illustrates that even when different templates are mixed together (intra-enrichment or post-enrichment), the templates do not exchange once associated with a polymerase.
Figure 8D:
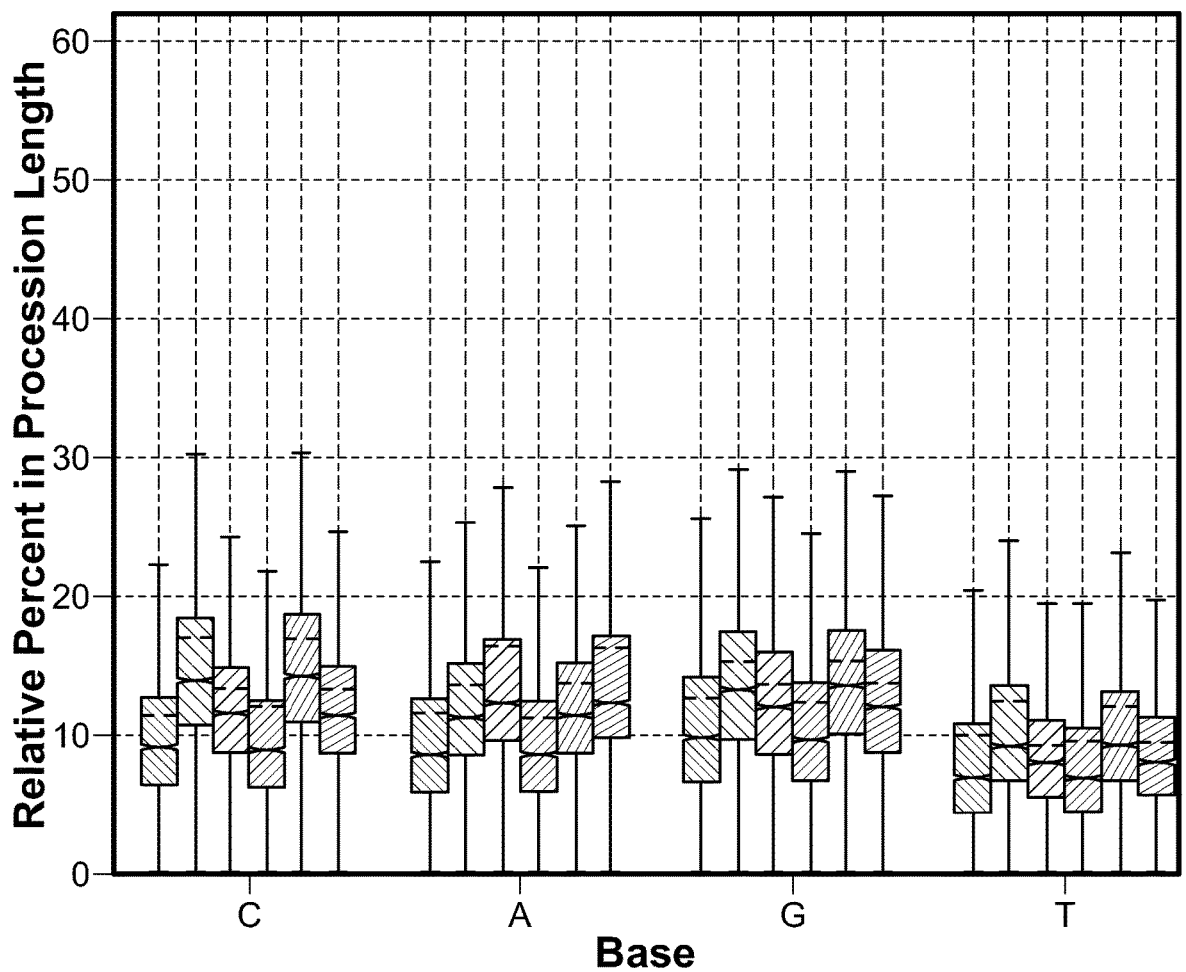
FIG. 8D illustrates that different deletion rates by base may be observed for each of the polymerase variants tested in a single experiment, and further illustrates that even when different templates are mixed together (intra-enrichment or post-enrichment), the templates do not exchange once associated with a polymerase.

After confirming the capability for the large-scale barcode identification, the method described herein was further evaluated to show multiplexed kinetic profiling of multiple polymerases in the same experiment. To test this each of the three nanopore-coupled polymerase variants were loaded with the first set of 32 templates (RPol1:CBT1-32), the second set from 33 through 64 (RPol2: CBT33-64) and the third set from 65 through 96 templates (RPol3:CBT65-96) from our library of 96 unique CBTs in separate template binding reactions. Subsequently, they were then mixed in equimolar ratios and inserted into the CMOS chip for sequencing reactions. The same barcode classification strategy as for the 96-plex experiments was used and a randomly distributed frequency histogram was obtained as expected (FIG. 7A). By evaluating 1,958 quality raw reads, all of the 96 possible barcodes were identified based on the BMPI cutoff. On average, the individual barcodes were sampled at least 20 times and the observation frequency ranged from 2-68 during measurement. The uneven distribution of the barcode counts (CBT1-32: low, CBT33-64: high, CBT65-96: high) reflected the previously observed processivity differences of the three different polymerase variants. Three separate control experiments were also performed for each of the three prepared complexes individually to assess the barcode identification specificity in a pooled sequencing reaction. 20 barcodes (63%) were uniquely identified for RPol1:CBT1-32 (number of quality raw reads, n=67), and 29 barcodes (90%) for both RPol2:CBT33-64 (n=249) and RPol3:CBT65-96 (n=383) out of the 32 possible barcodes for each set using the same classification scheme as for the single-polymerase, 96-plex experiment (FIG. 7B). For RPol1, the individual barcodes were observed at an average frequency of 5, which reflects its slow processivity. Meanwhile, for RPol2 and RPol3 the barcodes were counted at least 10 times on average ranging from 1-28 distinct observations. Thus, it was been shown that barcodes, in their respective set, can be uniquely identified with an average false positive rate of only ~13%. Here, it was demonstrated that three polymerase variants loaded with multiple different barcoded templates can be identified in a 96-plex fashion.

Example 9—Multiplex Kinetics Measurement

Finally, to demonstrate the ultimate practical utility of our method, we sought to determine how well the barcode sequencing data mapped back to the already determined kinetic properties of a polymerase variant (see FIGS. 6A to 6C). First, PCA was used on the multiplex sequencing data shown in FIG. 7A based on 20 derived kinetic properties as in the above Examples, in which all identified barcodes in each of the barcode sets (CBT1-32, CBT33-64, and CBT65-96, respectively) were accumulated in one group. In most cases, the 2D projections of the kinetic properties for each of these barcode groups onto the first two principal components mapped back well, when overlaid with the original PCA clusters derived from the individual "singleplex" RPol-CBT experiments (FIGS. 6A to 6C). Here, the cluster overlay was the measure of the classifier accuracy, which described how well it could distinguish polymerase variant kinetics based on the barcode sequencing information only. Sequencing data corresponding to the second barcode set (CBT33-64) could not be mapped back well, which could be due to the high false positive rate of barcode identification in that set. On the other hand, sequencing data corresponding to individual barcodes, could be mapped back with high-accuracy which highlights the potential of identifying a single polymerase variant in a multiplex experiment. Here, it has been shown that polymerase variants with a desired set of kinetic properties can be uniquely identified by applying the nanopore-based barcode sequencing techniques described herein. This points towards a future utility of identifying polymerase variants in a directed evolution scheme with desired kinetic properties, which can be iteratively refined with multiple design (key residue changes to affect kinetic properties), build (site directed mutagenesis) and test (barcode sequencing of polymerase mutant pool) cycles.

In Nanopore-SBS, polymerase kinetics were measured during template DNA sequencing and no further sample preparation is required. The results confirmed that we could load polymerases with circular templates and sequence these templates. By enabling repeated interrogation of the same barcoded template, we demonstrated high-sensitivity barcode identification using an alignment-based classification algorithm. These DNA templates also enabled us to distinguish kinetic parameters of polymerases, produced by site-directed mutagenesis, that have been loaded with unique barcoded templates. Finally, we showed high multiplexing potential in thousands of individually addressable pores of a CMOS chip. The unique kinetic signatures of each polymerase variants, obtained from the barcode sequencing information, permitted the discrimination of them in the same sample. Therefore, this nanopore-based platform could serve the basis for a multiplexed screening tool for DNA polymerases and can be further extended to a broad spectrum of applications in single-molecule enzyme activity or protein-protein interaction studies by correlating the desired molecular event to the observed ion current changes though a nanopore.

In Nanopore-SBS, polymerase kinetics are measured during template DNA sequencing and no further sample preparation is required. The results presented herein confirmed that polymerases could be loaded with circular templates and that those templates could be sequenced. By enabling repeated interrogation of the same barcoded template, we demonstrated high-sensitivity barcode identification using an alignment-based classification algorithm. These DNA templates also enabled us to distinguish kinetic parameters of polymerases, produced by site-directed mutagenesis, that have been loaded with unique barcoded templates. Finally, we showed high multiplexing potential in thousands of individually addressable pores of a CMOS chip. The unique kinetic signatures of each polymerase variants, obtained from the barcode sequencing information, permitted the discrimination of them in the same sample.

ADDITIONAL EMBODIMENTS

In another aspect of the present disclosure is a method of identifying a polymerase having a desired set of kinetic properties, the method comprising: (a) providing a device comprising (i) a nanopore array having a membrane that comprises membrane-embedded nanopores, wherein each nanopore is bound to a polymerase that is complexed with a circularized barcoded nucleic acid template, wherein at least two of the nanopores are bound to different polymerase variants each of which being complexed with a different circularized barcoded nucleic acid template, (ii) a reference electrode on the cis side of the membrane and an individually addressable electrode array on the trans side of the membrane, and (iii) an electrolyte solution in contact with both electrodes; (b) contacting the nanopore array with a set of nucleotides, wherein each nucleotide has a different tag that produces a different signal when the tag is captured during base incorporation; and (c) detecting the different signals over a period of time (i) to identify nucleic acid sequences corresponding to the barcode sequences of the circularized barcoded nucleic acid templates and (ii) to derive unique kinetic signatures, each corresponding to a single polymerase of the nanopore array, thereby identifying the polymerase having the desired set of kinetic properties. In some embodiments, step (c) is repeated multiple times, e.g. at least 10 times. In some embodiments, wherein the detecting step of (c) comprises measuring at least one of the following kinetic properties: rate of a full catalytic cycle of tagged nucleotide incorporation (FCR), rate of tag release after nucleotide incorporation (TRR), time duration for a distinct base call (tdwell), mean time duration for a distinct tag capture (TCD), and the number of observed current blockade events during a base call per unit time (TCR).

In some embodiments, the polymerase having the desired set of kinetic properties is identified by a method comprising: sequencing the circularized barcoded nucleic acid templates, producing a population of raw sequencing reads, and removing from the population sequencing reads having a length that is shorter than the length of a linearized barcoded nucleic acid template, wherein each raw sequencing read contains multiple barcode reads concatenated to each other; classifying the raw sequencing reads into barcode sequence reads by aligning the raw sequencing reads to a known barcode sequence, optionally using a concatenation multiplier (CM) calculated by the following formula: CM=sup (Lraw/Lbar), where Lraw is the length of raw read, Lbar is the length of the known barcode sequence; applying a progressive multiple sequence alignment algorithm to the barcode sequence reads, producing a barcode alignment, and producing a consensus barcode based on the barcode alignment; and aligning the consensus barcode with the barcodes of the different circularized barcoded nucleic acid template of step (a), producing a maximum alignment score, and identifying the polymerase having the desired set of kinetic properties based on the maximum alignment score, wherein a maximum alignment score of 0 indicates a total mismatch, and a maximum alignment score of 1 indicates a perfect match. In some embodiments, wherein the raw sequencing reads have a length of 100 to 100000; 100 to 10000; 100 to 1000 nucleotide bases; 400 to 600 nucleotide bases; or 500 nucleotide bases. In some embodiments, the consensus barcode has a length of at least 10 nucleotides.

In some embodiments, the circularized barcoded nucleic acid template is annealed to a primer. In some embodiments, the membrane is a lipid bilayer. In some embodiments, the polymerase is a DNA polymerase. In some embodiments, the different polymerases are variants of the same type of polymerase. In some embodiments, the different polymerases are different types of polymerases. In some embodiments, the nanopore array comprises at least 10 different polymerases. In some embodiments, the nanopore array comprises at least 50 different polymerases. In some embodiments, the nanopore array comprises 10 to 100,000 different polymerases. In some embodiments, the nucleic acid sequences of step (c)(i) are produced from the different signals using a probabilistic base-calling algorithm.

In some embodiments, the barcoded nucleic acid templates are produced by a method comprising: (a) providing a population of single-stranded nucleic acid templates, wherein each single-stranded nucleic acid template comprises a unique barcode sequence flanked by primer sequences; (b) eliminating one or more regions of the single-stranded nucleic acid templates that have a high-base-pairing probability; and (c) selecting a subpopulation of the single-stranded nucleic acid templates, wherein each unique barcode sequence of the subpopulation is not identical to any other unique barcode sequence of the subpopulation.

In another aspect of the present disclosure is a device comprising: (a) a nanopore array having a membrane that comprises membrane-embedded nanopores, wherein at least two nanopores are bound to a different polymerase, each different polymerase being complexed with a different circularized barcoded nucleic acid template, (b) a reference electrode on the cis side of the membrane, and an individually addressable electrode array on the trans side of the membrane, and (c) an electrolyte solution in contact with both electrodes. In some embodiments, the device further comprises a set of nucleotides, wherein each nucleotide has a different tag that produces a different signal when the tag is captured in a nanopore of the array during base incorporation. In some embodiments, the circularized barcoded nucleic acid template is annealed to a primer. In some embodiments, the membrane is a lipid bilayer. In some embodiments, the polymerase is a DNA polymerase. In some embodiments, the different polymerases are variants of the same type of polymerase. In some embodiments, the different polymerases are different types of polymerases. In some embodiments, the nanopore array comprises at least 10 different polymerases. In some embodiments, the nanopore array comprises at least 50 different polymerases. In some embodiments, the nanopore array comprises 10 to 100,000 different polymerases.

In another aspect of the present disclosure is kit comprising: a device comprising (i) a nanopore array having a membrane that comprises membrane-embedded nanopores, and (ii) a reference electrode on the cis side of the membrane and an individually addressable electrode array on the trans side of the membrane; and a set of different polymerases, each loaded or complexed with a different circularized barcoded nucleic acid template. In some embodiments, the kit further comprises a set of nucleotides, wherein each nucleotide has a different tag that produces a different signal when the tag is captured in a nanopore of the array. In some embodiments, the kit further comprises an electrolyte solution. In some embodiments, the set of different polymerases comprises at least 10 different polymerases.

In another aspect of the present disclosure is a method for generating barcoded nucleic acid templates, the method comprising: (a) providing a population of single-stranded nucleic acid templates, wherein each single-stranded nucleic acid template comprises a unique barcode sequence flanked by primer sequences; (b) eliminating at least one region of the single-stranded nucleic acid templates that has a high-base-pairing probability, optionally wherein a high-base-pairing probability is a minimum free energy (MFE) value above −10 kcal/mol calculated by MATLAB script 'rnafold' and (c) selecting a subpopulation of the single-stranded nucleic acid templates, wherein each unique barcode sequence of the subpopulation is not identical to any other unique barcode sequence of the subpopulation. In some embodiments, step (b) comprises determining the MFE associated with unique barcodes sequences of the subpopulation, selecting a threshold value based on the MFE, and eliminating the one or more regions based on the threshold value.

In some embodiments, the unique barcode sequence has a length of 20 to 50 nucleotides, or 30 to 40 nucleotides. In some embodiments, the primer sequences are at least 95% identical to each other, or are 100% identical to each other. In some embodiments, the length of the primer sequences is 10 to 30 nucleotides, or 20 to 25 nucleotides. In some embodiments, the single-stranded nucleic acid templates of the population and/or subpopulation have a length of 40 to 200 nucleotides, 40 to 100, or 45 to 55 nucleotides. In some embodiments, the subpopulation comprises at least 100, at least 1000, at least 10000, or at least 100,000 single-stranded nucleic acid templates that comprise a unique barcode sequence. In some embodiments, the method further comprises circularizing the single-stranded nucleic acid templates of the subpopulation.

In some embodiments is a method of screening a plurality of different enzyme variants using nanopore-based sequencing comprising: obtaining a biochip including a plurality of different nanopore sequencing complexes, wherein each different nanopore sequencing complex of the plurality of different nanopore sequencing complexes includes a polynucleotide having a unique molecular barcode, and wherein at least two of the different nanopore sequencing complexes include different enzyme variants; generating a sequencing data set for each different nanopore sequencing complex loaded onto the chip; classifying each of the generated sequencing data sets as associated with one different enzyme variant of the plurality of different enzyme variants based on identifications of the unique molecular barcodes included in the polynucleotides of the different nanopore sequencing complexes; and deriving a plurality of parameters for each one of the enzyme variants of the plurality of different enzyme variants, wherein the plurality of parameters for each one of the different enzyme variants are derived based on the classified sequence data sets associated with the respective one of the different enzyme variants. In embodiments where circularized templates are utilized, each of the generated sequencing data sets are classified as associated with a particular enzyme by (a) removing sequencing reads from the generated sequencing data sets having a length that is shorter than the length of a linearized barcoded nucleic acid template, wherein each raw sequencing read contains multiple barcode reads concatenated to each other; (b) classifying the raw sequencing reads in the sequencing data sets into barcode sequence reads by aligning the raw sequencing reads to a known (control) barcode sequence, optionally using a concatenation multiplier (CM) calculated by the following formula: CM=sup(Lraw/Lbar), where Lraw is the length of raw read, Lbar is the length of the known barcode sequence; applying a progressive multiple sequence alignment algorithm to the barcode sequence reads, producing a barcode alignment, and producing a consensus barcode based on the barcode alignment; and aligning the consensus barcode with the barcodes of the different templates of the nanopore sequencing complexes for which the sequencing data sets were generated; wherein a maximum alignment score of 0 indicates a total mismatch, and a maximum alignment score of 1 indicates a perfect match.

In some embodiments, and to test if we could identify circular templates using the polymerase-nanopore system, three synthetic single-stranded DNA (ssDNA) molecules consisting of a unique 32-base barcode region flanked by a common 19-base primer region were designed. They were circularized using either CircLigase or T4 ligase utilizing the primer region as a splint, then primed with the same universal primer to generate the circular barcoded templates (CBT). All CBTs met two design specifications, (1) all sequence identities were <85% when the templates were locally aligned to each other to make them act as unique identifiers, and (2) the structures were optimized to eliminate regions of high-base pairing probability after circularization.

In some embodiments, to demonstrate the suitability of barcode identification, a Smith-Waterman alignment-based barcode classification algorithm was implemented which computes a probability score, henceforth defined as barcode match probability index (BMPI), that describes the relative measure of how uniquely a barcode can be identified compared to the other possible barcodes in the measurement set. First, quality reads were filtered out by requiring their read length to be greater than one (51 base) and less than ten full barcode iterations and their consensus sequence length to be greater than 10 base.

In some embodiments, voltage signal events were converted to raw reads using a commercial probabilistic base-calling algorithm (version 2.9.2, Roche Sequencing Solutions, Santa Clara, CA). Raw reads, with read lengths greater than one full barcode iteration (51 base), were then fed as input to a Smith-Waterman (SW) alignment-based barcode classification algorithm, which assigns a BMPI value to that read. More specifically, the first step was to classify the different regions in the raw circular reads into barcode reads. This was achieved by locally aligning the raw read sequence to the known concatenated barcode sequence, where the concatenation multiplier (CM) is calculated by the following formula:

$$CM = \sup(L\_raw / L\_bar)$$

where Lraw is the length of raw read; Lbarcode is the length of barcode and CM is an integer. Once all barcode iteration boundaries were identified, we utilized the multialign function from the Bioinformatics Toolbox of MATLAB (2017a, MathWorks, Natick, MA) to perform a progressive multiple alignment of the repeated barcode sequences. Next, we generated the consensus sequence of these multiple aligned reads using seqconsensus, which was subsequently locally aligned to all potential barcodes in the experimental set, if the consensus sequence length was at least 10 base. Finally, the maximum scoring (SW) alignment identified the most likely barcode candidate, which was evaluated based on the particular input sequence. This score was defined as the BMPI and is used to measure the barcode identification probability with possible range of [0,1], where 0 means total mismatch and 1 denotes a total match. For all alignments, homopolymer sequences in the template, and repeated base calls of the same nucleotide in the raw sequencing reads were considered a single base.

Additional Embodiment 1. A method of screening a plurality of different enzyme variants using nanopore-based sequencing comprising:
  a. obtaining a biochip including a plurality of different nanopore sequencing complexes, wherein each different nanopore sequencing complex of the plurality of different nanopore sequencing complexes includes a polynucleotide having a unique molecular barcode, and wherein at least two of the different nanopore sequencing complexes have different enzyme variants;

b. generating a sequencing data set for each different nanopore sequencing complex loaded onto the chip;
c. classifying each of the generated sequencing data sets as associated with one different enzyme variant of the plurality of different enzyme variants based on identifications of the unique molecular barcodes included in the polynucleotides of the different nanopore sequencing complexes; and
d. deriving a plurality of parameters for each one of the enzyme variants of the plurality of different enzyme variants, wherein the plurality of parameters for each one of the different enzyme variants are derived based on the classified sequence data sets associated with the respective one of the different enzyme variants.

Additional Embodiment 2. The method of additional embodiment 1, wherein the identifications of the unique molecular barcodes included in the different nanopore sequencing complexes comprises (i) filtering quality reads to meet a minimum threshold base length; (ii) deriving a probability score using an automated alignment-based algorithm; and (iii) evaluating whether a computed probability score at least meets a pre-determined threshold probability score value.

Additional Embodiment 3. The method of additional embodiment 2, wherein the pre-determined threshold probability score value is 0.80.

Additional Embodiment 4. The method of additional embodiment 3, wherein the automated alignment-based classification algorithm derives the probability score by (i) identifying all barcode iteration boundaries in a raw read; (ii) splitting the iteration boundaries into individual barcode reads; (iii) aligning the individual barcode reads using an automated multiple sequence alignment algorithm to generate a consensus barcode from the alignment; (iv) locally aligning the generated consensus barcode to all possible barcodes utilized in the screening; and (v) identifying a most likely barcode candidate based on the sequence identify.

Additional Embodiment 5. The method of additional embodiment 1, wherein a single sequence data set classified as associated with the one different enzyme variant is utilized to derive the plurality of parameters for that one different enzyme variant.

Additional Embodiment 6. The method of additional embodiment 1, wherein at least two sequence data sets classified as associated with the one different enzyme variant are utilized to derive the plurality of parameters for that one different enzyme variant.

Additional Embodiment 7. The method of additional embodiment 1, wherein the plurality of parameters for each one of the different enzyme variants are selected from the group consisting of dwell time, a rate of a full catalytic cycle of tagged nucleotide incorporation, a tag release relate after nucleotide incorporation, a tag capture rate, and a tag capture dwell time.

Additional Embodiment 8. The method of additional embodiment 7, wherein the plurality of parameters are derived for each different nucleotide type.

Additional Embodiment 9. The method of additional embodiment 8, further comprising performing a principal component analysis on the derived plurality of parameters for the each one of the different enzyme variants of the plurality of different enzyme variants.

Additional Embodiment 10. The method of additional embodiment 8, further comprising evaluating whether a processivity rate for at least one nucleotide is altered for a first different enzyme variant of the plurality of different enzyme variants as compared with a second different enzyme variant of the plurality of different enzyme variants.

Additional Embodiment 11. The method of additional embodiment 10, wherein the evaluation comprises comparing at least one parameter of the plurality of parameters of the first different enzyme variant with the same at least one parameter of the second different enzyme variant.

Additional Embodiment 12. The method of additional embodiment 1, wherein the enzymes are polymerases or reverse transcriptases.

Additional Embodiment 13. The method of additional embodiment 1, wherein the enzymes are polymerases.

Additional Embodiment 14. The method of additional embodiment 13, wherein at least three of the different nanopore sequencing complexes comprise three different polymerase variants.

Additional Embodiment 15. The method of additional embodiment 14, wherein one of the at least three different polymerase variants is a control and wherein the other different polymerase variants each include at least one different mutation in comparison to the control.

Additional Embodiment 16. The method of additional embodiment 1, wherein the unique molecular barcode comprises a nucleic acid sequence having between 10 and 50 bases.

Additional Embodiment 17. The method of additional embodiment 16, wherein each of the unique molecular barcodes have less than 85% sequence identity to each other.

Additional Embodiment 18. The method of additional embodiment 1, wherein the unique molecular barcode comprises a nucleic acid sequence having any of SEQ ID NOS: 1 to 3.

Additional Embodiment 19. The method of additional embodiment 1, wherein the polynucleotide comprises a unique molecular bar code and a Common Reading Region.

Additional Embodiment 20. A method of screening at least two enzyme variants using nanopore-base sequencing comprising:
obtaining a biochip including a plurality of individually addressable nanopores, and wherein the obtained biochip comprises at least first and second different nanopore sequencing complexes, the first nanopore sequencing complex comprising a first enzyme variant and a first polynucleotide, and the second nanopore sequencing complex comprising a second enzyme variant and a second polynucleotide, wherein the first and second polynucleotides each include a different molecular barcode, and wherein the first and second enzyme variants are different;
generating sequencing data sets for at least each of the first and second nanopore sequencing complexes;
classifying each of the generated sequencing data sets as associated with at least either the first enzyme variant or the second enzyme variant, wherein the sequence data sets are each classified as associated with the at least either the first enzyme variant or the second enzyme variant based on identifications of at least the unique molecular barcodes included with the first and second polynucleotides; and
deriving a plurality of kinetics parameters for each of the first and second enzyme variants based on the classified data sets associated with the first enzyme variant or the second enzyme variant.

Additional Embodiment 21. The method of additional embodiment 20, further comprising loading a third nanopore sequencing complex on the biochip, the third nanopore sequencing complex comprising a third enzyme variant and a third polynucleotide, wherein the third enzyme variant differs from the first and second enzyme variants, and wherein the third polynucleotide comprises a different molecular barcode than the first and second polynucleotide variants.

Additional Embodiment 22. The method of additional embodiment 20, wherein the first and second enzyme variants are polymerase variants.

Additional Embodiment 23. The method of additional embodiment 22, wherein the nanopore-based sequencing comprises detecting byproducts of nucleotide incorporation events.

Additional Embodiment 24. The method of additional embodiment 23, wherein the byproducts are detected with an electrode disposed adjacent to each individually addressable nanopore.

Additional Embodiment 25. A biochip comprising a plurality of different nanopore sequencing complexes, each different nanopore sequencing complex comprising a different polynucleotide template, wherein the different polynucleotide templates each include a unique molecular barcode, and wherein at least two of the different nanopore sequencing complexes of the plurality of different nanopore sequencing complexes comprise different polynucleotide binding proteins, and wherein the different polynucleotide binding proteins are variants of each other.

Additional Embodiment 26. The biochip of additional embodiment 25, wherein the polynucleotide templates each include a Common Reading Region.

Additional Embodiment 27. The biochip of additional embodiment 25, wherein the biochip is loaded with at least three different nanopore sequencing complexes including at least three different polynucleotide binding protein variants.

Additional Embodiment 28. The biochip of additional embodiment 25, wherein the polynucleotide binding protein variants are polymerase variants.

Additional Embodiment 29. The biochip of additional embodiment 25, wherein the polynucleotide binding protein variants are DNA polymerase variants.

Additional Embodiment 30. The biochip of additional embodiment 25, wherein the polynucleotide binding protein variants are RNA polymerase variants.

Additional Embodiment 31. The biochip of additional embodiment 25, wherein the polynucleotide binding protein variants are reverse transcriptase variants.

Additional Embodiment 32. The biochip of additional embodiment 25, wherein the polynucleotide binding protein variants are helicase variants.

Additional Embodiment 33. The biochip of additional embodiment 25, wherein the polynucleotide binding protein variants are exonuclease variants.

Additional Embodiment 34. The biochip of additional embodiment 25, wherein each of the plurality of nanopores within the biochip are individually addressable.

Additional Embodiment 35. The biochip of additional embodiment 25, wherein each individually addressable nanopore is adapted to detect a tag that is released from a tagged nucleotide upon polymerization of the tagged nucleotide by a polymerase variant.

Additional Embodiment 36. The biochip of additional embodiment 25, wherein each nanopore is individually coupled to sensing circuitry.

Additional Embodiment 37. A system comprising the biochip of additional embodiment 25 and one or more processors coupled to the biochip, wherein the one or more processors are programmed to aid in classifying the detected nucleic acid sequences of each of the different polynucleotide templates as associated with one of the different polynucleotide binding protein variants.

Additional Embodiment 38. The system of additional embodiment 37, wherein the one or more processors are further programmed to derive one or more parameters for each of the different polynucleotide binding protein variants.

Additional Embodiment 39. A method for generating barcoded nucleic acid templates, the method comprising: (a) eliminating at least one region from each single-stranded nucleic acid template of a population of single-stranded nucleic acid templates, wherein the region for elimination has a high-base pairing probability, and wherein each of the single-stranded nucleic acid templates comprises a unique barcode sequence flanked by a primer sequence; and (b) selecting a subpopulation of the single-stranded nucleic acid templates from the population of single-stranded nucleic acid templates, wherein each single-stranded nucleic acid template within the subpopulation comprises a different unique barcode sequence.

Additional Embodiment 40. The method of additional embodiment 39, further comprising determining the minimum free energy (MFE) associated with the unique barcode sequences of the subpopulation, selecting a threshold value based on the MFE, and eliminating the one or more regions based on the threshold value.

Additional Embodiment 41. The method of additional embodiment 40, wherein the region for elimination having the high-base pairing probability is a nucleotide sequence having a MFE value above −10 kcal/mol.

Additional Embodiment 42. The method of additional embodiment 41, wherein the MFE value is calculated using a MATLAB script 'rnafold.'

Additional Embodiment 43. The method of additional embodiment 39, wherein the unique barcode sequences have a length ranging from between 20 nucleotides to 50 nucleotides.

Additional Embodiment 44. The method of additional embodiment 39, wherein the primer sequences are at least 95% identical to each other.

Additional Embodiment 45. The method of additional embodiment 39, wherein a length of the primer sequences ranges from between about 10 nucleotides to about 30 nucleotides.

Additional Embodiment 46. The method of additional embodiment 39, wherein the subpopulation comprises at least 100 single-stranded nucleic acid templates.

Additional Embodiment 47. The method of additional embodiment 39, further comprising circularizing the single-stranded nucleic acid templates of the subpopulation.

Additional Embodiment 48. A method of screening a plurality of different nanopore variants using nanopore-based sequencing comprising:
  a. obtaining a biochip including a plurality of different nanopore sequencing complexes, wherein each different nanopore sequencing complex of the plurality of different nanopore sequencing complexes includes a polynucleotide having a unique molecular barcode, and wherein at least two of the different nanopore sequencing complexes have different nanopore variants;
  b. generating a sequencing data set for each different nanopore sequencing complex loaded onto the chip;
  c. classifying each of the generated sequencing data sets as associated with one different nanopore variant of the plurality of different nanopore variants based on identifications of the unique molecular barcodes included in the polynucleotides of the different nanopore sequencing complexes; and d. deriving a plurality of parameters for each one of the nanopore variants of the plurality of different nanopore variants, wherein the plurality of parameters for each one of the different nanopore variants are derived based on the classified sequence data sets associated with the respective one of the different nanopore variants.

Additional Embodiment 49. The method of additional embodiment 48, wherein at least two different nanopore variants are screened.

Additional Embodiment 50. The method of additional embodiment 48, wherein at least two of the different nanopore sequencing complexes comprise different enzyme variants.

Additional Embodiment 51. The method of additional embodiment 48, wherein the biochip comprises at least four different nanopore sequencing complexes, and wherein the at least four different nanopore sequencing complexes comprise different combinations of at least two different nanopore variants and at least two different enzyme variants.

Additional Embodiment 52. In the method of additional embodiment 51, wherein the at least two different enzyme variants are polymerase variants.

Additional Embodiment 53. The method of additional embodiment 48, wherein the unique molecular barcode comprises a nucleic acid sequence having between 10 and 150 bases.

Additional Embodiment 54. The method of additional embodiment 53, wherein the unique molecular barcode comprises a nucleic acid sequence having between 10 and 100 bases.

Additional Embodiment 55. The method of additional embodiment 53, the unique molecular barcode comprises a nucleic acid sequence having between 10 and 50 bases.

Additional Embodiment 56. The method of additional embodiment 53, wherein each of the unique molecular barcodes have less than 85% sequence identity to each other.

Additional Embodiment 57. The method of additional embodiment 48, wherein the unique molecular barcode comprises a nucleic acid sequence having any of SEQ ID NOS: 1 to 3.

Additional Embodiment 58. The method of additional embodiment 48, wherein the polynucleotide comprises a unique molecular bar code and a Common Reading Region.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A method of screening a plurality of different enzyme variants using nanopore-based sequencing comprising:
   obtaining a biochip including a plurality of different nanopore sequencing complexes, wherein each different nanopore sequencing complex of the plurality of different nanopore sequencing complexes includes a polynucleotide having a unique molecular barcode, and wherein at least two of the plurality of different nanopore sequencing complexes have different enzyme variants, wherein the plurality of different enzyme variants are polymerase variants or reverse transcriptase variants;
   generating a sequencing data set for each different nanopore sequencing complex loaded onto the biochip;
   classifying each of the generated sequencing data sets as associated with one different enzyme variant of the plurality of different enzyme variants based on identifications of the unique molecular barcodes included in the polynucleotides of the different nanopore sequencing complexes; and
   deriving a plurality of parameters for each one of the enzyme variants of the plurality of different enzyme variants, wherein the plurality of parameters for each one of the different enzyme variants are derived based on the classified sequence data sets associated with the respective one of the different enzyme variants.

2. The method of claim 1, wherein the identifications of the unique molecular barcodes included in the different nanopore sequencing complexes comprises (i) filtering quality reads to meet a minimum threshold base length; (ii) deriving a probability score using an automated alignment-based algorithm; and (iii) evaluating whether a computed probability score at least meets a pre-determined threshold probability score value.

3. The method of claim 2, wherein the pre-determined threshold probability score value is 0.80.

4. The method of claim 3, wherein the automated alignment-based classification algorithm derives the probability score by (i) identifying all barcode iteration boundaries in a raw read; (ii) splitting the iteration boundaries into individual barcode reads; (iii) aligning the individual barcode reads using an automated multiple sequence alignment algorithm to generate a consensus barcode from the alignment; (iv) locally aligning the generated consensus barcode to all possible barcodes utilized in the screening; and (v) identifying a most likely barcode candidate based on the sequence identify.

5. The method of claim 1, wherein a single sequence data set classified as associated with the one different enzyme variant is utilized to derive the plurality of parameters for that one different enzyme variant.

6. The method of claim 1, wherein at least two sequence data sets classified as associated with the one different enzyme variant are utilized to derive the plurality of parameters for that one different enzyme variant.

7. The method of claim 1, wherein the plurality of parameters for each one of the different enzyme variants are selected from the group consisting of dwell time, a rate of a full catalytic cycle of tagged nucleotide incorporation, a tag release relate after nucleotide incorporation, a tag capture rate, and a tag capture dwell time.

8. The method of claim 7, wherein the plurality of parameters are derived for each different nucleotide type.

9. The method of claim 8, further comprising performing a principal component analysis on the derived plurality of parameters for the each one of the different enzyme variants of the plurality of different enzyme variants.

10. The method of claim 8, further comprising evaluating whether a processivity rate for at least one nucleotide is altered for a first different enzyme variant of the plurality of different enzyme variants as compared with a second different enzyme variant of the plurality of different enzyme variants.

11. The method of claim 10, wherein the evaluation comprises comparing at least one parameter of the plurality of parameters of the first different enzyme variant with the same at least one parameter of the second different enzyme variant.

12. The method of claim 1, wherein the plurality of different enzyme variants are polymerase variants.

13. A method of screening at least two enzyme variants using nanopore-base sequencing comprising:
   obtaining a biochip including a plurality of individually addressable nanopore sequencing complexes, and wherein the obtained biochip comprises at least first and second different nanopore sequencing complexes, the first nanopore sequencing complex comprising a first enzyme variant and a first polynucleotide, and the second nanopore sequencing complex comprising a second enzyme variant and a second polynucleotide, wherein the first and second polynucleotides each include a different molecular barcode, and wherein the first and second enzyme variants are different;
   generating sequencing data sets for at least each of the first and second nanopore sequencing complexes, wherein the generated sequencing data sets for the at least the first and second nanopore sequencing complexes are derived from signals detected by a sensing circuit associated with the at least the first and second nanopore sequencing complexes;
   classifying each of the generated sequencing data sets as associated with at least either the first enzyme variant or the second enzyme variant, wherein the sequence data sets are each classified as associated with the at least either the first enzyme variant or the second enzyme variant based on identifications of at least the unique molecular barcodes included with the first and second polynucleotides; and
   deriving a plurality of kinetics parameters for each of the first and second enzyme variants based on the classified data sets associated with the first enzyme variant or the second enzyme variant,
   wherein the at least two enzyme variants are polymerase variants or reverse transcriptase variants.

14. A method of characterizing a plurality of different nanopore variants using nanopore-based sequencing comprising:
   a. obtaining a biochip including a plurality of different nanopore sequencing complexes wherein each different nanopore sequencing complex of the plurality of different nanopore sequencing complexes are individually addressable, wherein each different nanopore sequencing complex is associated with a different polynucleotide, wherein each different polynucleotide includes a unique molecular barcode and the same common region, and wherein at least two of the different nanopore sequencing complexes of the plurality of different nanopore sequencing complexes have different nanopore variants;
   b. generating a sequencing data set for each of the plurality of different nanopore sequencing complexes by sequencing each of the different polynucleotides associated with each of the plurality of different nanopore sequencing complexes, wherein each of the generated sequencing data sets is derived from signals detected by a sensing circuit associated with each of the individually addressable nanopore sequencing complexes;

c. associating each of the generated sequencing data sets with one of the different nanopore variants based on identifications of the different unique molecular barcodes included in each of the different polynucleotides associated with each of the different nanopore sequencing complexes; and d. characterizing each of the different nanopore variants based on one or more metrics derived from the generated sequencing data sets associated with each of the different nanopore variants, wherein the one or more metrics are based on the sequencing of the same common portion of each of the different polynucleotides associated with each of the plurality of different nanopore sequencing complexes.

* * * * *

SEQUENCE LISTING

```
<160> NUMBER OF SEQ ID NOS: 3

<210> SEQ ID NO 1
<211> LENGTH: 58
<212> TYPE: DNA
<213> ORGANISM: Artificial Sequence
<220> FEATURE:
<223> OTHER INFORMATION: Molecular barcode sequence

<400> SEQUENCE: 1
cagtcagtat ttcccaaacc ctttaaaagg gtttgggaaa aaaaacggag gaggagga        58

<210> SEQ ID NO 2
<211> LENGTH: 58
<212> TYPE: DNA
<213> ORGANISM: Artificial Sequence
<220> FEATURE:
<223> OTHER INFORMATION: Molecular barcode sequence

<400> SEQUENCE: 2
cagtcagtaa aaccctttcc ctttaaaagg gaaagggttt aaaaacggag gaggagga        58

<210> SEQ ID NO 3
<211> LENGTH: 58
<212> TYPE: DNA
<213> ORGANISM: Artificial Sequence
<220> FEATURE:
<223> OTHER INFORMATION: Molecular barcode sequence

<400> SEQUENCE: 3
cagtcagtat ttccctttcc ctttaaaagg gaaagggaaa aaaaacggag gaggagga        58
```